(12) United States Patent
Blaesi et al.

(10) Patent No.: US 11,865,216 B2
(45) Date of Patent: *Jan. 9, 2024

(54) EXPANDABLE STRUCTURED DOSAGE FORM FOR IMMEDIATE DRUG DELIVERY

(71) Applicant: Aron H. Blaesi, Cambridge, MA (US)

(72) Inventors: Aron H. Blaesi, Cambridge, MA (US); Nannaji Saka, Cambridge, MA (US)

(73) Assignee: Aron H. Blaesi, Cambridge, MA (US)

( * ) Notice: Subject to any disclaimer, the term of this patent is extended or adjusted under 35 U.S.C. 154(b) by 798 days.

This patent is subject to a terminal disclaimer.

(21) Appl. No.: 16/860,911

(22) Filed: Apr. 28, 2020

(65) Prior Publication Data

US 2020/0268680 A1 Aug. 27, 2020

Related U.S. Application Data

(63) Continuation of application No. PCT/US2019/019004, filed on Feb. 21, 2019.
(Continued)

(51) Int. Cl.
*A61K 9/70* (2006.01)

(52) U.S. Cl.
CPC ............. *A61K 9/70* (2013.01); *A61K 9/7007* (2013.01)

(58) Field of Classification Search
CPC .... A61K 31/192; A61K 9/146; A61K 9/5015; A61K 9/5026; A61K 9/70; A61K 9/7007; A61K 31/167; A61K 47/38; A61K 35/28; A61K 38/14; A61K 38/212; A61K 39/395; A61K 47/32; A61K 47/34; A61K 9/0065; A61K 9/0092; A61K 9/06; A61K 9/107; A61K 9/2054; A61K 9/2095; A61K 47/10; A61K 9/2031; A61K 9/2072; A61K 47/02; A61K 47/42; A61K 9/2077; A61K 9/209; A61K 31/616; A61K 9/122; A61K 9/1641; A61K 9/2027; A61K 9/4808; A61K 9/4866; A61K 38/10; A61K 9/0019; A61K 38/08; A61K 2035/128; A61K 9/1647; A61K 9/0024; A61K 9/1635; A61K 38/47; A61K 38/49; A61K 38/1875; A61K 38/39; A61K 38/1825; A61K 38/1841; A61K 38/1858; A61K 45/06; A61K 9/1682; A61K 2300/00; A61K 35/32; A61K 47/14; A61K 9/5192; A61K 38/16; A61K 47/22; A61K 9/0031; A61K 9/0034; A61K 9/0043; A61K 9/006; A61K 9/1075; A61K 9/1274; A61K 9/145; A61K 9/1617; A61K 9/5123; A61K 38/00; A61K 8/64; A61K 31/195; A61K 33/30; A61K 35/39; A61K 48/00; A61K 8/11; A61K 8/27; A61K 8/34; A61K 8/8129; A61K 9/14; A61K 9/16; A61K 9/1694; A61K 2800/54; A61K 31/197; A61K 31/216; A61K 31/4418; A61K 31/4422; A61K 31/4745; A61K 35/14; A61K 35/30; A61K 38/17; A61K 38/1703; A61K 38/18; A61K 38/1808; A61K 38/1866; A61K 38/20; A61K 38/363; A61K 38/4833; A61K 47/12; A61K 47/36; A61K 47/645; A61K 49/00; A61K 8/02; A61K 8/0208; A61K 8/027; A61K 8/65; A61K 9/1652; A61K 9/50; A61K 9/5031; A61K 9/5073; A61K 9/7023; A61K 2035/126; A61K 2039/505; A61K 2039/6018; A61K 2039/6093; A61K 2800/31; A61K 2800/805; A61K 2800/86; A61K 31/00; A61K 31/185; A61K 31/198; A61K 31/21; A61K 31/27; A61K 31/277; A61K 31/337; A61K 31/397; A61K 31/4035; A61K 31/407; A61K 31/417; A61K 31/4184; A61K 31/435; A61K 31/438; A61K 31/44; A61K 31/4439; A61K 31/451; A61K 31/47; A61K 31/495; A61K 31/4965; A61K 31/5377; A61K 31/702; A61K 31/7028; A61K 31/715; A61K 31/722; A61K 35/12; A61K 35/745; A61K 35/747; A61K 36/315; A61K 36/704; A61K 36/708; A61K 38/13; A61K 38/1709; A61K 38/1729; A61K 38/185; A61K 38/42; A61K 38/43; A61K 38/44; A61K 38/4813; A61K 38/482; A61K 38/4873; A61K 38/488;
(Continued)

(56) References Cited

U.S. PATENT DOCUMENTS

| | | | |
|---|---|---|---|
| 5,330,763 A * | 7/1994 | Gole | A61K 8/44 424/441 |
| 11,129,798 B2 * | 9/2021 | Blaesi | A61K 47/10 |

(Continued)

FOREIGN PATENT DOCUMENTS

WO    WO2017/075096 A1 *    5/2017    .............. A61K 9/00

*Primary Examiner* — Audrea B Coniglio
*Assistant Examiner* — Audrea Buckley

(57) ABSTRACT

In this specification, a pharmaceutical dosage form comprising a three-dimensional structural framework of thin, solid elements surrounded by interconnected void space is disclosed. The elements comprise at least a drug, a water-absorptive, polymeric excipient, and a hydrophilic surface composition. Upon immersion in a dissolution fluid the three-dimensional structural framework is wetted uniformly, transitions from solid to viscous due to the diffusion of dissolution fluid into the thin elements, expands in all dimensions, and disintegrates and releases drug. The disclosed dosage form enables greater drug delivery rates and better control of the drug concentration in blood for improving the efficacy and safety of drug therapies.

37 Claims, 32 Drawing Sheets

Related U.S. Application Data

(60) Provisional application No. 62/733,624, filed on Sep. 19, 2018, provisional application No. 62/633,602, filed on Feb. 21, 2018.

(58) Field of Classification Search
CPC ...... A61K 47/06; A61K 47/183; A61K 47/26; A61K 47/44; A61K 47/60; A61K 47/61; A61K 47/6903; A61K 47/6921; A61K 47/6927; A61K 51/1258; A61K 8/40; A61K 8/9789; A61K 9/0004; A61K 9/0053; A61K 9/0097; A61K 9/10; A61K 9/19; A61K 9/20; A61K 9/2009; A61K 9/2081; A61K 9/4816; A61K 9/5063; A61K 9/51; A61K 9/5169
See application file for complete search history.

(56) References Cited

U.S. PATENT DOCUMENTS

| | | | |
|---|---|---|---|
| 11,478,427 B2* | 10/2022 | Blaesi | A61K 47/42 |
| 2016/0184230 A1* | 6/2016 | Blaesi | A61K 9/1641 |
| | | | 264/53 |

* cited by examiner

EXPANDABLE STRUCTURED DOSAGE FORM FOR IMMEDIATE DRUG DELIVERY

CROSS-REFERENCE TO RELATED INVENTIONS

This application is a continuation of, and incorporates herein by reference in its entirety, the International Application No. PCT/US2019/19004 filed on Feb. 21, 2019, and titled "Expanding structured dosage form", which claims priority to and the benefit of the U.S. Provisional Application No. 62/633,602 filed on Feb. 21, 2018, and the U.S. Provisional Application No. 62/733,624 filed on Sep. 19, 2018. All foregoing applications are hereby incorporated by reference in their entirety.

This application is related to, and incorporates herein by reference in their entirety, the U.S. application Ser. No. 15/482,776 filed on Apr. 9, 2017 and titled "Fibrous dosage form", the U.S. application Ser. No. 15/964,058 filed on Apr. 26, 2018 and titled "Method and apparatus for the manufacture of fibrous dosage forms", and the U.S. application Ser. No. 15/964,063 filed on Apr. 26, 2018 and titled "Dosage form comprising two-dimensional structural elements".

BACKGROUND OF THE INVENTION

At present, the most prevalent pharmaceutical dosage forms, the oral-delivery tablets and capsules, are porous solids of compacted drug and excipient particles. Upon ingestion, the gastrointestinal fluid percolates the open pores of the dosage form, and promotes its fragmentation and drug particle dissolution. The dissolved drug molecules are then absorbed by the blood stream, and distributed to the disease-specific target sites in the human body.

Despite great commercial success, an inherent limitation of compacted powders for drug delivery applications is the non-deterministic and non-interconnected porosity. As a result, the rate and the extent of fluid percolation into the dosage form cannot be precisely controlled. Therefore, the range and control of the drug delivery rate into the blood stream are limited.

To overcome such limitations, therefore, in the commonly known U.S. patent application Ser. No. 15/482,776 the present inventors (Blaesi and Saka) have introduced fibrous dosage forms. As shown schematically in FIG. 1, these dosage forms comprise solid frameworks 100, 102, 104 of a drug-excipient composite (or a solid solution) surrounded by contiguous void space 130, 132, 134 (or free space). Upon immersion in a dissolution fluid 140, 142, 144, the fluid 140, 142, 144 may percolate into the interconnected free spaces 130, 132, 134, and the solid framework 100, 102, 104 (e.g., the water-soluble excipient) and the dissolution fluid 140, 142, 144 may interdiffuse. Two non-limiting cases then present themselves.

In the first, shown schematically in FIG. 1a, the framework 100 dissolves, the dissolved molecules diffuse into the free spaces 130, and are convected through the free spaces 130 into the free-flowing dissolution fluid 140. Drug is released as the framework 100 dissolves. This case is generally observed for frameworks 100 comprising water-soluble, low molecular-weight excipients forming dilute, low-viscosity solutions with water, or dosage forms with very small volume fraction of fibers.

In the second case, represented by FIGS. 1b and 1c, at least one water-soluble excipient has a greater molecular weight, and/or the volume fraction of fibers is greater. As a result, upon immersion in a dissolution fluid the structural framework 102, 104 transitions from solid to a viscous medium 152, 154 (e.g., a viscous dispersion, a viscous solution, or a viscous mass with a viscosity greater or far greater than the viscosity of the dissolution fluid). Drug may be released by either deformation and dissolution of the viscous medium 152, as shown schematically in FIG. 1b, or by diffusion of drug molecules through the viscous medium 154 as illustrated in FIG. 1c.

The type of solid-to-viscous transition greatly affects the rate at which drug is delivered into the blood stream, and thus is a critical design parameter for enhancing the efficacy and reducing side effects of drug therapies.

Design Considerations

Four non-limiting types of solid-to-viscous transitions are described briefly in the following paragraphs. The descriptions and any supporting illustrations will enable one of ordinary skill in the art to more readily understand the invention presented throughout this disclosure. They are not meant to be limiting in any way.

In the first type, represented by FIG. 2a, the solid dosage form 200 consists of a three dimensional structural framework 202 of drug particles 210 and a water-soluble and water-absorptive polymeric excipient 220. The framework 202 is surrounded by interconnected free space 230. The volume occupied by the excipient 220 in the framework 202 is much smaller than the volume of the free space 230.

Upon immersion in a dissolution fluid 240, the fluid 240 percolates rapidly into the interconnected free space 230. The excipient 220 and the dissolution fluid 240 then inter-diffuse to form a viscous medium 250 consisting of fluidized (or dissolved) excipient molecules 222, drug molecules 212, and drug particles 210. The concentration of excipient molecules 222 in the viscous medium 250 is very small. Thus the viscosity of the viscous medium 250 is small, too. As a result, the medium 250 deforms and dissolves rapidly in the dissolution fluid 240.

Moreover, as shown schematically in FIG. 2b, upon ingestion the dosage form disintegrates rapidly in the stomach fluid and releases drug particles (and drug molecules). The drug particles then dissolve and concurrently pass into the small intestine. The dissolved drug molecules are finally absorbed by the blood stream.

This type of dosage form is adequate for immediate delivery of drugs with large solubility and diffusivity in the gastrointestinal tract. However, because the mass of water-soluble excipient in the dosage form is very small, the physicochemical properties of the drug (e.g., the drug solubility in gastrointestinal fluid, the permeability of drug across the gastrointestinal wall, etc.) and the drug release rate by the dosage form cannot be tailored by the excipient. This limits the range of the drug delivery rate into the blood stream, and control of drug concentration in the blood stream.

In the second type, therefore, as illustrated by FIG. 3a the solid dosage form 300 again consists of a three dimensional structural framework 302 of drug and water-soluble and water-absorptive polymeric excipient surrounded by interconnected free space 330. Unlike in the previous case, however, the volume of polymeric excipient 320 in the dosage form 300 now is far greater than the volume of the free spaces 330. As a result, upon immersion in a dissolution fluid the dosage form 300 transitions to a viscous medium 350 of large excipient concentration and viscosity. Thus the viscous medium 350 now is a thick, highly viscous mass that is essentially undeformable by the dissolution fluid 340; it erodes slowly from the outside. As a result, while the content of water-soluble, polymeric excipient in the dosage form is greater than in the first case, the drug release rate by the dosage form is slower. The range and control of the drug delivery rate into the blood stream are again limited, and the efficacy and safety of the drug therapy may be compromised as detailed below.

By way of example but not by way of limitation, as shown schematically in FIG. 3b, upon ingestion the slowly-eroding dosage form or viscous mass may pass from the stomach into the small intestine and travel downward along the gastrointestinal tract, thereby releasing drug. If the drug release rate is too slow, part of the ingested drug may not be released or absorbed within the gastrointestinal transit time, $t_{tr}$, and thus may be excreted. As a result, because the gastrointestinal transit time is generally variable, the mass of drug absorbed may be variable, too. Variability in the absorbed drug mass (e.g., variability in bioavailability) may compromise both the efficacy and safety of drug therapies. Thus, variability should be eliminated.

The trade-off between fast dosage form disintegration (or dissolution) and large content of water-soluble, polymeric excipient may be overcome, however, if the dosage form expands while transitioning to a viscous medium. Thus, in the third type, illustrated by FIG. 4a, the volume of polymeric excipient 420 in the three dimensional structural framework 402 is again greater than the volume of free space 430. Unlike in the previous case, however, upon immersion in a dissolution fluid 440 the dosage form structure 402, 450 is ever expanding. As a result, the excipient concentration in the dosage form structure 402 or viscous medium 450 ever decreases and eventually is of the order of or smaller than the disentanglement concentration. Therefore, the viscosity of the "terminal" viscous medium 450 will be very small; the "terminal" medium 450 deforms and dissolves rapidly in the dissolution fluid 440.

Upon ingestion, as shown schematically in FIG. 4b, the dosage form may disintegrate and dissolve in the upper part of the gastrointestinal tract. The dissolved drug molecules may then be absorbed by the blood stream. Variabilities in the drug delivery rate due to slow or inconsistent dosage form disintegration may be eliminated.

Furthermore, simultaneous to the fast and consistent dosage form disintegration and drug release rate, the expanding dosage form may release large quantities of water-soluble, functional excipients in a short time. Such functional excipients may, for example, enhance the delivery rate of released drug molecules by enhancing the drug concentration or drug solubility in gastrointestinal fluid, or by enhancing the drug absorption rate into the blood stream, and so on. Thus, the expanding dosage form enables a greater and more consistent drug delivery rate into the blood stream for improving the efficacy and safety of a myriad of drug therapies.

In the fourth type, as shown schematically in FIG. 5a the structure 502, 550 again expands as polymeric excipient 520 and dissolution fluid 540 interdiffuse. Eventually, however, the pores (e.g., the free spaces or the free space) 530 close out, expansion of the viscous dosage form or medium 550 ceases, and an expanded, viscous mass 550 is formed. The viscous mass 550 is a concentrated polymer solution or dispersion. It is essentially undeformable and erodes or dissolves slowly into the dissolution fluid, thereby releasing drug. This type of dosage form is not optimal for immediate drug release. However, it could potentially be applied as a gastro-retentive dosage form, thus enabling improved control of the concentration of many drugs in blood, FIG. 5b.

SUMMARY OF THE INVENTION

The above considerations suggest that a solid dosage form which transitions to a viscous medium upon ingestion and expands thereby enables improved control of drug concentration in the blood stream and improved therapeutic outcomes. In one aspect, therefore, the disclosed pharmaceutical dosage form comprises a drug-containing solid having an outer surface and an internal three dimensional structural framework of one or more thin structural elements, said framework contiguous with and terminating at said outer surface; said thin structural elements comprising at least an active pharmaceutical ingredient, at least an absorptive polymeric excipient, and at least a hydrophilic surface composition; said thin structural elements further having segments spaced apart from adjoining segments, thereby defining free spaces, wherein a plurality of adjacent free spaces combine across the drug-containing solid to define one or more interconnected free spaces forming an open pore network; whereby upon immersion in a physiological fluid said open pore network enables uniform wetting of the structural framework, and the drug-containing solid transitions to a viscous medium, thereby expanding in all dimensions.

In some embodiments, upon immersion in a physiological fluid the drug-containing solid dissolves or disintegrates in said physiological fluid.

In some embodiments, the drug-containing solid dissolves or disintegrates during or after transitioning to a viscous medium.

In some embodiments, the drug-containing solid expands due to the penetration of physiological or body fluid into the thin elements of the three dimensional structural framework.

In some embodiments, the drug-containing solid expands due to the penetration of physiological or body fluid into an absorptive polymeric excipient.

In some embodiments, at least one dimension of the drug-containing solid expands to at least 1.12 times its initial length while transitioning to a viscous medium.

In some embodiments, the drug-containing solid expands to at least 1.4 times its initial volume while transitioning to a viscous medium.

In some embodiments, at least one dimension of the drug-containing solid expands to at least 1.12 times its initial length within no more than 20 minutes of immersing in a physiological or body fluid.

In some embodiments, the drug-containing solid expands to at least 1.4 times its initial volume within no more than 20 minutes of immersing in a physiological or body fluid.

In some embodiments, the drug-containing solid expands to a volume greater than 1.5 times its initial volume within 4 minutes of immersing in a physiological or body fluid (e.g., within 4 minutes after contact with physiological or body fluid).

In some embodiments, the drug-containing solid expands isotropically while transitioning to a viscous medium.

In some embodiments, geometric similarity of the three dimensional structural framework of elements is preserved as it expands and transitions to a fluidic or viscous medium.

In some embodiments, at least one structural element expands isotropically while transitioning to a fluidic or viscous medium.

In some embodiments, the drug-containing solid transitions to a viscous medium having a viscosity in the range of 0.01 to 10,000 Pa·s.

In some embodiments, eighty percent of the drug content in the drug-containing solid is released in less than 45 minutes after immersion in a physiological or body fluid.

In some embodiments, the one or more elements expand substantially anisotropically, so that the drug-containing solid transitions to viscous mass, said viscous mass having a viscosity at least three orders of magnitude greater than the viscosity of the dissolution fluid.

In some embodiments, eighty percent of the drug content in the drug-containing solid is released in a time between 30 minutes and 72 hours (e.g., between 30 minutes and 48 hours or between 30 minutes and 24 hours).

In some embodiments, the one or more elements comprise an average thickness no greater than 2.5 mm (e.g., no greater than 1 mm or in the ranges 1 µm-1 mm 5 µm-1 mm or 10 µm-1 mm).

In some embodiments, the effective free spacing between the segments across the one or more free spaces on average is greater than 1 µm (e.g., greater than 5 µm, or greater than 10 µm, or in the ranges 1 µm-2 mm 10 µm-2 mm or 20 µm-2 mm).

In some embodiments, the position of at least one element or at least one segment in the three dimensional structural framework of one or more elements is precisely controlled.

In some embodiments, the volume fraction of elements or segments with precisely controlled position in the three dimensional structural framework of one or more elements is greater than 0.3.

In some embodiments, the three dimensional structural framework of one or more elements comprises an ordered structure.

In some embodiments, the effective free spacing and element thickness are precisely controlled.

In some embodiments, the three dimensional structural framework of one or more thin structural elements comprises a plurality of stacked layers of elements or segments.

In some embodiments, the elements comprise segments bonded to other segments at point contacts, the number of point contacts in the three dimensional structural framework being precisely controlled.

In some embodiments, one or more segments are diffusion-bonded to one or more other segments.

In some embodiments, at least one element is a fiber.

In some embodiments, plies of fibers, or fiber segments, are stacked in a cross-ply arrangement to form a three dimensional structural framework.

In some embodiments, the three dimensional structural framework of one or more thin structural elements comprises a plurarity of criss-crossed stacked layers of fibrous structural elements.

In some embodiments, the spacing between adjoining fibers or adjoining fiber segments in a layer or ply is uniform or equidistant.

In some embodiments, at least one element is a sheet.

In some embodiments, at least one element is a bead.

In some embodiments, the surface of at least one element or the surface of at least one segment comprises a coating.

In some embodiments, the coating comprises a highly hydrophilic surface composition for enhancing the rate of wetting of the structural framework or the rate of fluid percolation into the open pore network.

In some embodiments, the at least one highly hydrophilic coating composition is selected from the group comprising polyethylene glycol, polyvinyl alcohol, polyvinyl alcohol-polyethylene glycol copolymer, polyvinyl pyrrolidone, silicon dioxide, talc, magnesium stearate, mannitol, xylitol, maltitol, erythritol, sucrose, glucose, isomalt, maltodextrin, or lactitol.

In some embodiments, the free spacing between segments and the composition of the surface of the one or more elements are so that the percolation time of physiological/body fluid into one or more interconnected free spaces of the drug-containing solid is no greater than 200 seconds under physiological conditions.

In some embodiments, rate of penetration of the physiological/body fluid into an element or an absorptive excipient under physiological conditions is greater than the average thickness of said element divided by 3600 seconds.

In some embodiments, an effective diffusivity of physiological/body fluid in an element or an absorptive excipient is greater than $1 \times 10^{-12}$ m$^2$/s under physiological conditions.

In some embodiments, at least one absorptive polymeric excipient is selected from the group comprising hydroxypropyl methylcellulose, hydroxyethyl cellulose, polyvinyl alcohol, polyvinylpyrrolidone, hydroxypropyl methylcellulose acetate succinate, sodium alginate, hydroxypropyl cellulose, methyl cellulose, hydroxypropyl methyl ether cellulose, starch, chitosan, pectin, polymethacrylates (e.g., poly (methacrylic acid, ethyl acrylate) 1:1, or butylmethacrylat-(2-dimethylaminoethyl)methacrylat-methylmathacrylat-copolymer), polyacrylic acid, or vinylpyrrolidone-vinyl acetate copolymer.

In some embodiments, at least one absorptive polymeric excipient comprises a plurality of individual chains that disentangle upon immersion in a physiological fluid.

In some embodiments, the molecular weight of at least one absorptive polymeric excipient is greater than 2 kg/mol (e.g., greater than 5 kg/mol, or greater than 10 kg/mol, or greater than 20 kg/mol, or greater than 50 kg/mol).

In some embodiments, the molecular weight of at least one absorptive polymeric excipient is between 2 kg/mol and 500 kg/mol (e.g., in the ranges 5-500 kg/mol, 10-500 kg/mol, 2-200 kg/mol, 5-200 kg/mol, 2-50 kg/mol, or 2-100 kg/mol).

In some embodiments, the weight fraction of absorptive polymeric excipient in the three dimensional structural framework of one or more elements is greater than 0.1 (e.g. greater than 0.15, or greater than 0.2, or greater than 0.25).

In some embodiments, the absorptive polymeric excipient is predominantly in an amorphous phase.

In some embodiments, drug molecules or drug particles are embedded in a matrix comprising absorptive polymeric excipient.

In some embodiments, drug and excipient in the structural elements form a solid solution.

In some embodiments, at least one active pharmaceutical ingredient comprises a solubility no greater than 5 g/l (e.g., no greater than 2 g/l, or no greater than 1 g/l, or no greater than 0.5 g/l, or no greater than 0.2 g/l, or no greater than 0.1 g/l) in a physiological or body fluid under physiological conditions.

In some embodiments, at least one active pharmaceutical ingredient comprises a pH-dependent solubility in a physiological or body fluid.

In some embodiments, at least one active pharmaceutical ingredient comprises a solubility that is at least five times (e.g. at least ten times) greater in acidic solution than in basic solution.

In some embodiments, at least one active pharmaceutical ingredient is a basic compound.

In some embodiments, the tensile strength of the three dimensional structural framework of one or more elements is between 0.01 MPa and 100 MPa (this includes, but is not limited to tensile strength of at least one element is greater than 0.02 MPa, or greater than 0.05 MPa, or greater than 0.1 MPa, or greater than 0.2 MPa, or greater than 0.5 MPa, or greater than 1 MPa, or greater than 1.5 MPa, or greater than 2 MPa, or greater than 3 MPa, or greater than 5 MPa).

In some embodiments, less than five walls must be ruptured to obtain an interconnected cluster of free space from the outer surface of the drug-containing solid to any point in the internal structure.

In some embodiments, at least one free space is enclosed by walls to form a closed cell, and wherein less than five walls must be ruptured to obtain an interconnected cluster of free space from the outer surface of the drug-containing solid to any point in the internal structure.

In some embodiments, average length, average width, and average thickness of the drug-containing solid or three dimensional structural framework of elements are greater than 0.5 mm (e.g., greater than 1 mm or greater than 1.5 mm or greater than 2 mm or in the ranges 1 mm-30 mm 1.5 mm-30 mm or 2 mm-30 mm).

In another aspect, the disclosed pharmaceutical dosage form comprises a drug-containing solid having an outer surface and an internal three dimensional structural framework of one or more thin structural elements with average element thickness in the range of 1 μm to 1 mm, said framework contiguous with and terminating at said outer surface; said thin structural elements comprising at least an active pharmaceutical ingredient, at least 15 weight percent of one or more absorptive polymeric excipients having a molecular weight in the range between 2 kg/mol and 500 kg/mol, and at least a hydrophilic surface composition; said thin structural elements further having segments spaced apart from adjoining segments, thereby defining free spaces, wherein a plurality of adjacent free spaces combine across the drug-containing solid to define one or more interconnected free spaces forming an open pore network; wherein upon immersion in a physiological fluid said open pore network enables uniform wetting of the structural framework, and the physiological fluid penetrates into the thin fibers, so that the drug-containing solid expands isotropically in all dimensions and within no more than 20 minutes of immersion transitions to a viscous medium having a viscosity in the range of 0.01 to 10,000 Pa·s and a length at least 1.15 times the initial length of the drug-containing solid; and whereby said viscous medium disintegrates in said physiological fluid during or after transitioning to a viscous medium, thereby releasing drug.

Moreover, in another aspect the pharmaceutical dosage form comprises a drug-containing solid having an outer surface and an internal three dimensional structural framework comprising a plurality of criss-crossed stacked layers of fibrous structural elements with average fiber thickness in the range of 1 μm to 1 mm said framework contiguous with and terminating at said outer surface; said fibrous structural elements comprising at least an active pharmaceutical ingredient, at least 15 weight percent of one or more absorptive polymeric excipients having a molecular weight in the range between 2 kg/mol and 500 kg/mol, and at least a hydrophilic surface composition; said fibrous structural elements further having segments spaced apart from like segments of adjoining fibrous elements, thereby defining free spaces, wherein a plurality of adjacent free spaces of successive layers combine to define one or more interconnected free spaces forming an open pore network; wherein upon immersion in a physiological fluid said open pore network enables uniform wetting of the structural framework, and the physiological fluid penetrates into the thin fibers, so that the drug-containing solid expands isotropically in all dimensions and within no more than 20 minutes of immersion transitions to a viscous medium having a viscosity in the range of 0.01 to 10,000 Pa·s and a length at least 1.15 times the initial length of the drug-containing solid; and whereby said viscous medium disintegrates in said physiological fluid during or after transitioning to a viscous medium, thereby releasing drug.

A non-limiting method of manufacturing the disclosed dosage form comprises the steps of injecting at least one active ingredient and at least one absorptive polymeric excipient into an extrusion channel having a cross section extending along its length inside a housing; injecting a solvent to solvate at least one injected granular solid so that the one or more injected granular solids form a plasticized matrix; conveying the plasticized matrix towards an exit port of the extrusion channel by applying mechanical work on the plasticized matrix; extruding the plasticized matrix through an exit port to form at least one plasticized fiber; and structuring at least one plasticized fiber to a three dimensional structural framework of one or more drug-containing fibers; wherein upon immersion in a physiological fluid the three dimensional structural framework is uniformly wetted and transitions to a viscous medium, thereby expanding in all dimensions.

Another non-limiting method of manufacturing the disclosed dosage form comprises the steps of injecting one or more active ingredients and one or more excipients into an extrusion channel having a cross section extending along its length inside a housing, wherein at least one excipient melts upon heating; heating the injected one or more active ingredients and one or more excipients to form a plasticized matrix; conveying the plasticized matrix towards an exit port of the extrusion channel by applying mechanical work on the plasticized matrix; extruding the plasticized matrix through an exit port to form at least one plasticized fiber; and structuring at least one plasticized fiber to a three dimensional structural network of one or more drug-containing fibers.

In some embodiments, the structuring of at least one plasticized fiber to a three dimensional structural network of one or more drug-containing fibers is performed by 3D-patterning said at least one plasticized fiber on a substrate.

In some embodiments, the three dimensional structural framework of one or more drug-containing fibers comprises a plurality of criss-crossed stacked layers of fibrous structural elements.

Moreover, a non-limiting apparatus to manufacture the disclosed dosage form comprises an internally hollow housing having an internal surface encapsulating and defining an extrusion channel having a first end and a second end and a cross section extending axially along its length from said first end to said second end and terminating into an exit port at the second end; said housing having at least a first feeding port between the first end and second end for injecting at least one solid constituent into the extrusion channel, and at least a second feeding port between the first feeding port and the exit port for injecting at least one solvent into the extrusion channel to form a plasticized matrix by solvating at least one injected solid constituent; at least one conveying element for extruding the plasticized matrix in the extrusion channel through an exit port to form at least one plasticized fiber; and a fiber structuring unit to structure one or more plasticized fibers to a three dimensional structural network of one or more drug-containing fibers; wherein upon immersion in a physiological fluid the three dimensional structural framework is uniformly wetted and transitions to a viscous medium, thereby expanding in all dimensions.

Another non-limiting apparatus to manufacture the disclosed dosage form comprises an internally hollow housing having an internal surface encapsulating and defining an extrusion channel having a first end and a second end and a cross section extending axially along its length from said first end to said second end and terminating into an exit port at the second end; said housing having at least a first feeding port between the first end and second end for injecting at least one solid constituent into the extrusion channel; at least one heating element for fluidizing at least one injected solid constituent so that the injected one or more solid constituents form a plasticized matrix in the extrusion channel; at least one conveying element for extruding the plasticized matrix in the extrusion channel through an exit port to form at least one plasticized fiber; and a fiber structuring unit to structure one or more plasticized fibers to a three dimensional structural network of one or more drug-containing fibers; wherein upon immersion in a physiological fluid the three dimensional structural framework is uniformly wetted and transitions to a viscous medium, thereby expanding in all dimensions.

In some embodiments, the fiber structuring unit comprises a translating or rotating stage.

In some embodiments, the stage comprises at least a perforation through which gas flows for solidifying the deposited structure.

In some embodiments the deposited structure is solidified by applying a gas flow through it.

In some embodiments, the one or more plasticized fibers are structured to a three dimensional structural network of one or more drug-containing fibers by 3D-patterning said one or more plasticized fibers on a substrate defined by or attached to a translating or rotating stage.

In some embodiments, the three dimensional structural framework of one or more drug-containing fibers comprises a plurality of criss-crossed stacked layers of fibrous structural elements.

Embodiments described with respect to one aspect of the invention can be applied with respect to another aspect. By way of example but not by way of limitation, certain embodiments of the claims described with respect to the first aspect can include features of the claims described with respect to the second, third, fourth, fifth, sixth, or seventh aspect, and vice versa. Similarly, features described with respect to one embodiment of the invention can be applied with respect to another embodiment.

This invention may be better understood by reference to the accompanying drawings, attention being called to the fact that the drawings are primarily for illustration, and should not be regarded as limiting.

BRIEF DESCRIPTION OF THE DRAWINGS

The objects, embodiments, features, and advantages of the present invention are more fully understood when considered in conjunction with the following accompanying drawings.

DEFINITIONS

Figure 1:
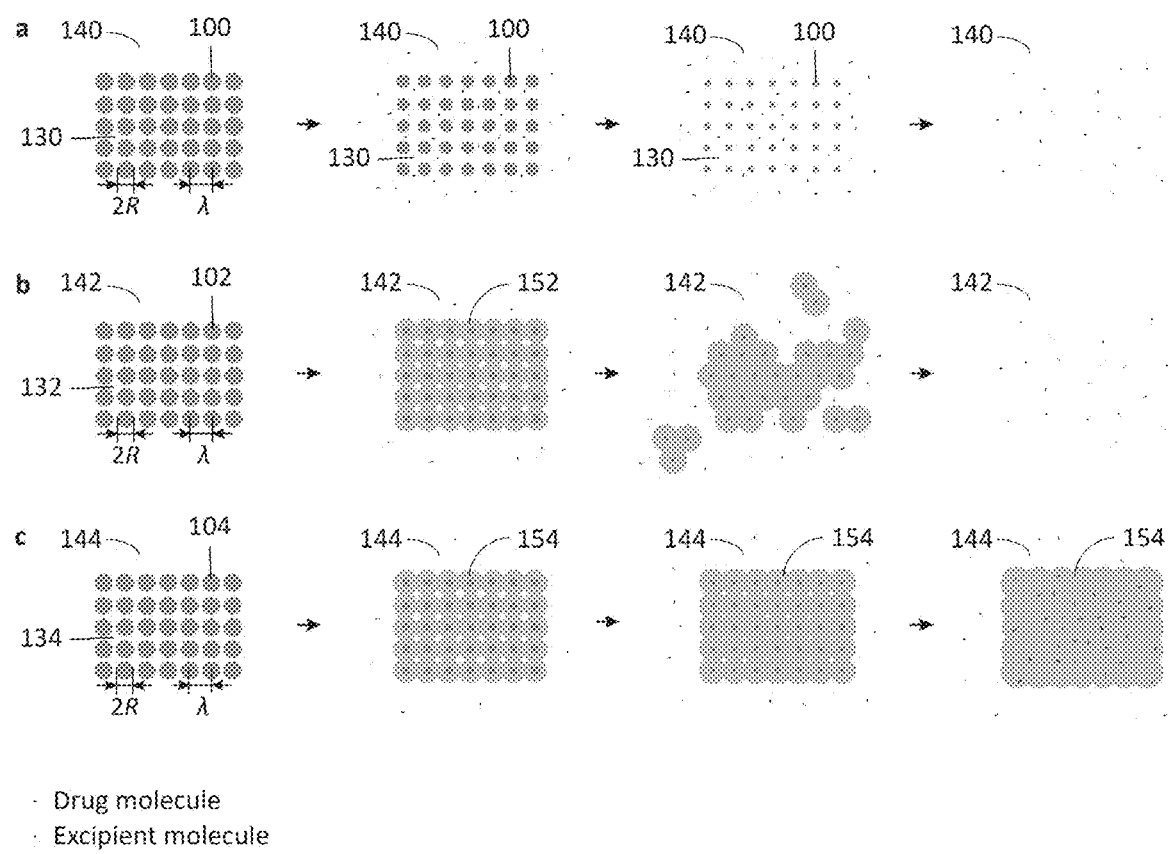
FIG. 1 illustrates non-limiting schematics of (a) a fibrous dosage form where the structure erodes during dissolution, (b) a fibrous dosage form that forms a viscous medium that deforms and dissolves rapidly, and (c) a fibrous dosage form that forms a highly viscous medium or mass that dissolves slowly.
Figure 2:
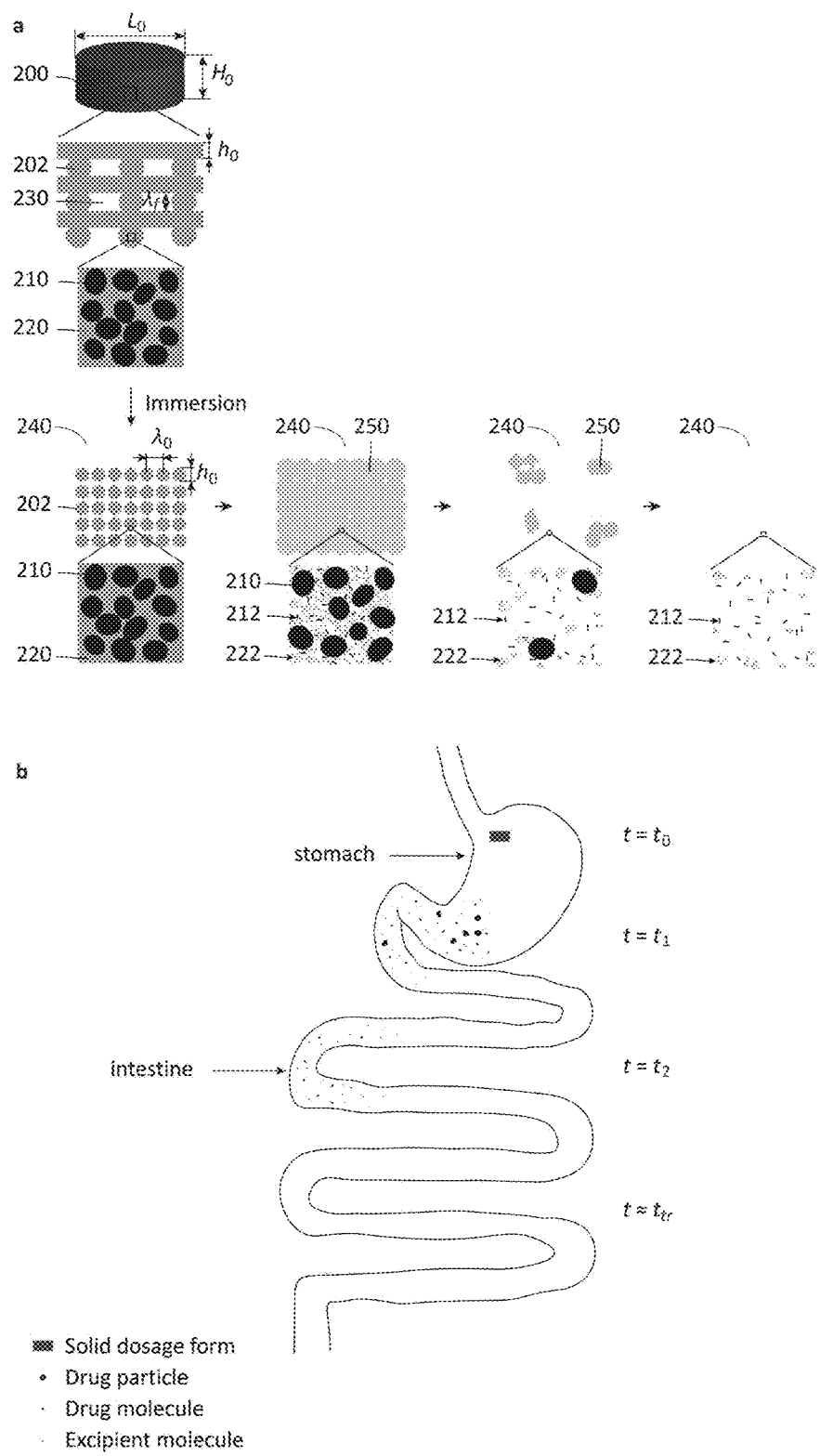
FIG. 2 illustrates non-limiting schematics of (a) a solid dosage form comprising a three dimensional structural framework of drug and excipient and its conversion (e.g., transition) to a viscous medium upon immersion in a dissolution fluid, and (b) the dosage form disintegration, drug release, and drug absorption processes after ingestion.
Figure 3:
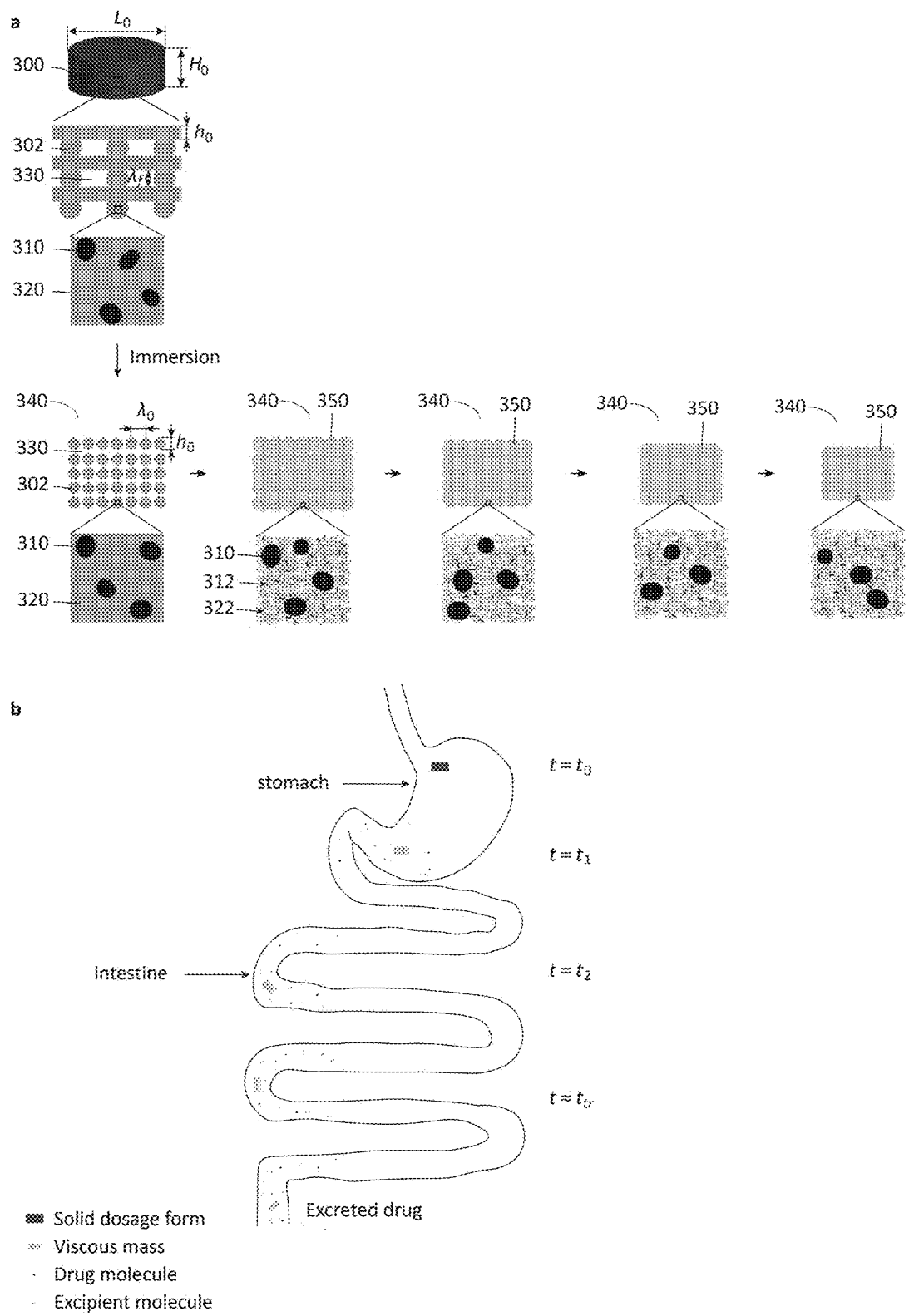
FIG. 3 presents other non-limiting schematics of (a) a solid dosage form comprising a three dimensional structural framework of drug and excipient and its transition to a viscous medium upon immersion in a dissolution fluid, and (b) the dosage form disintegration, drug release, and drug absorption processes after ingestion.
Figure 4:
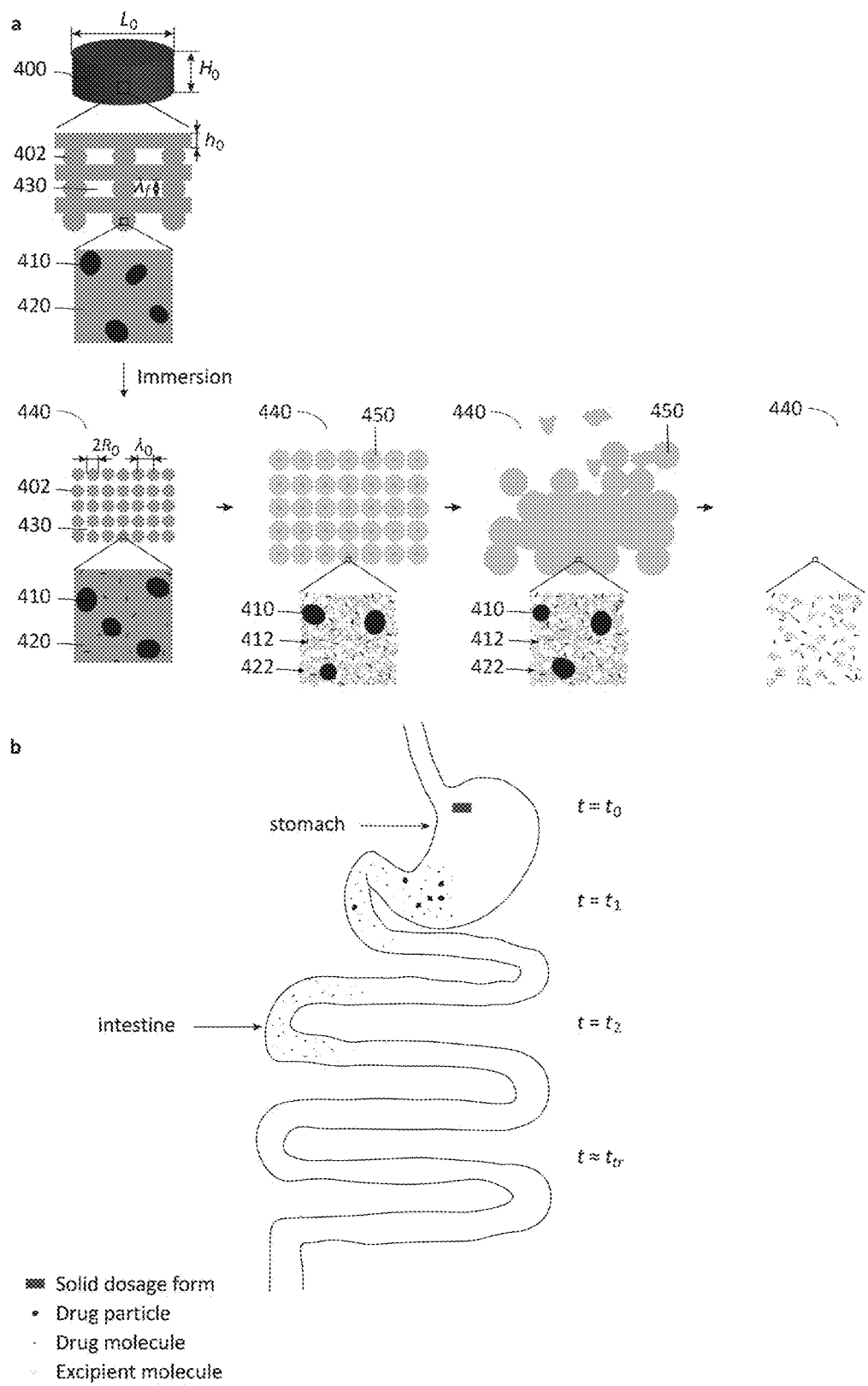
FIG. 4 illustrates non-limiting schematics of (a) a solid dosage form comprising a three dimensional structural framework that expands as it transitions to a viscous medium upon immersion in a dissolution fluid, and (b) the dosage form disintegration, drug release, and drug absorption processes after ingestion.
Figure 5:
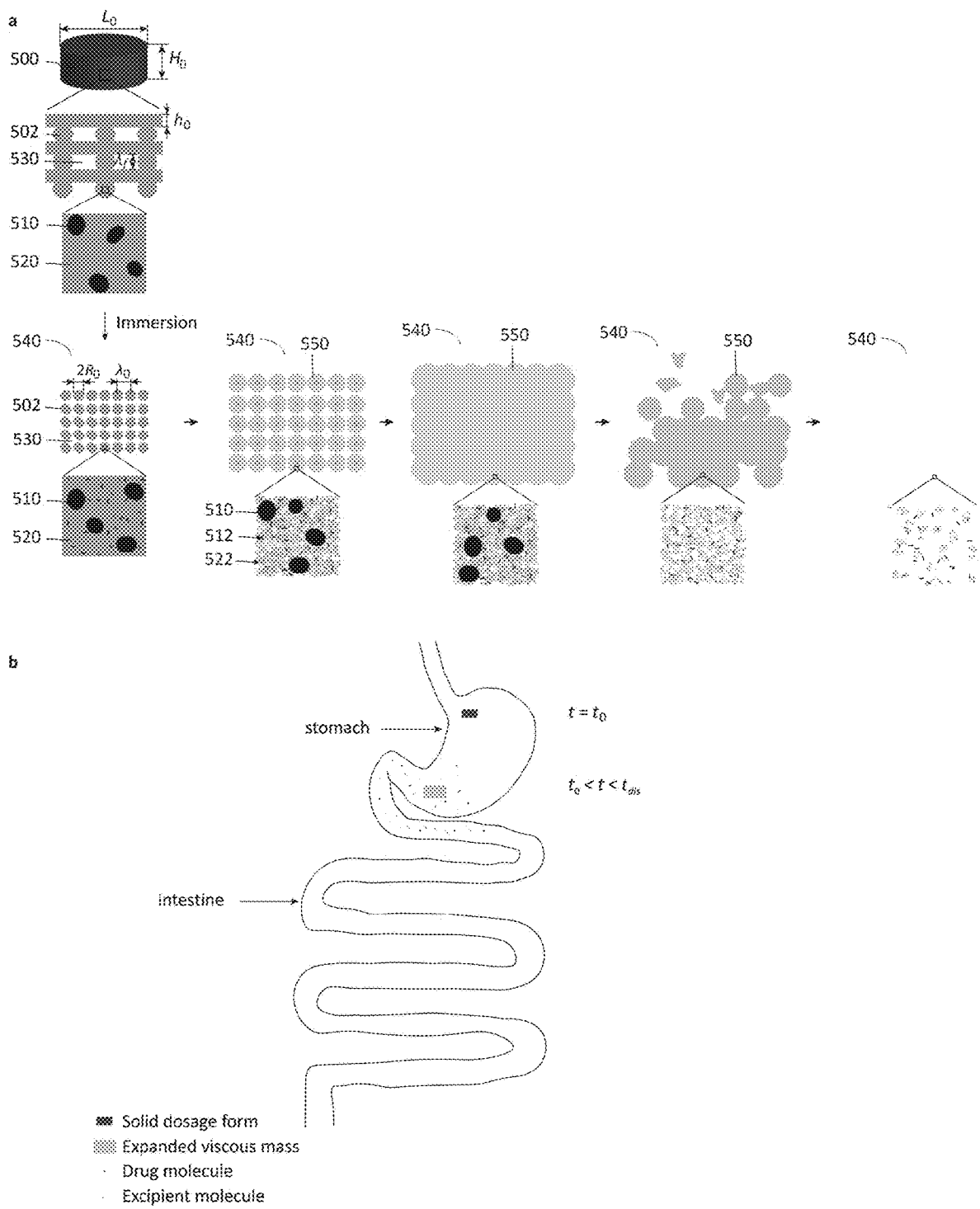
FIG. 5 shows other non-limiting schematics of (a) a solid dosage form comprising a three dimensional structural framework that expands as it transitions to a viscous medium in a dissolution fluid, and (b) the dosage form disintegration, drug release, and drug absorption processes after ingestion.

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Moreover, in the disclosure herein, the terms "one or more active ingredients", "at least one active ingredient", "active ingredient", "active pharmaceutical ingredient", and "drug" are used interchangeably. As used herein, an "active ingredient" or "active agent" refers to an agent whose presence or level correlates with elevated level or activity of a target, as compared with that observed absent the agent (or with the agent at a different level). In some embodiments, an active ingredient is one whose presence or level correlates with a target level or activity that is comparable to or greater than a particular reference level or activity (e.g., that observed under appropriate reference conditions, such as presence of a known active agent, e.g., a positive control).

Furthermore, in the context of some embodiments herein, a three dimensional structural framework of one or more thin structural elements comprises a drug-containing structural framework (e.g., a network, skeleton, assembly, assemblage, or arrangement) of one or more thin structural elements that extends over a length, width, and thickness greater than 100 µm. This includes, but is not limited to drug-containing structural frameworks that extend over a length, width, and thickness greater than 200 µm, or greater than 300 µm, or greater than 500 µm, or greater than 700 µm, or greater than 1 mm or greater than 1.25 mm or greater than 1.5 mm, or greater than 2 mm.

In other embodiments, a three dimensional structural framework of one or more thin structural elements comprises a drug-containing structural framework (e.g., a network, skeleton, assembly, assemblage, or arrangement) of one or more thin structural elements that extends over a length, width, and thickness greater than the average thickness of at least one element (or at least one segment) in said structural framework. This includes, but is not limited to structural frameworks that extend over a length, width, and thickness greater than 1.5, or greater than 2, or greater than 2.5, or greater than 3, or greater than 3.5, or greater than 4, or greater than 5 times the average thickness of at least one element (or at least one segment) in the structural framework. It may be noted that the terms "three dimensional structural framework of drug-containing elements", "three dimensional structural framework of elements", "three dimensional structural framework of one or more thin structural elements", "three dimensional structural framework of one or more elements", "three dimensional structural framework", and "three dimensional framework of elements" are used interchangeably herein.

Moreover, in preferred embodiments a three dimensional structural framework of one or more thin structural elements comprises a plurality of stacked layers of thin structural elements (or segments). This includes, but is not limited to at least two stacked layers of thin structural elements (or segments), or at least three stacked layers of thin structural elements (or segments), or at least four stacked layers of thin structural elements (or segments), or at least five stacked layers of thin structural elements (or segments).

As used herein, the terms "element", "elements", "one or more elements", "one or more thin elements", "one or more thin structural elements", "structural elements", "one or more drug-containing elements", and "drug-containing elements", are used interchangeably. They are understood as the solid, drug-containing structural elements (or building blocks) that make up the three dimensional structural framework (e.g., the dosage form structure or the structure of a drug-containing solid). Thin structural elements comprise two-dimensional elements (2-dimensional structural elements), one-dimensional elements (1-dimensional structural elements), or zero-dimensional elements (0-dimensional structural elements).

As used herein, a two-dimensional structural element or "sheet" is referred to as having a length and width much greater than the thickness. More specifically, in the present disclosure the length and width of a two-dimensional structural element are greater than 2 times the thickness. This includes, but is not limited to a length and width greater than 3 times, or greater than 4 times, or greater than 5 times, or greater than 6 times, or greater than 8 times, or greater than 10 times, or greater than 12 times the thickness. Moreover, in some embodiments that are included but not limiting herein, the length and width of a sheet are greater than 0.3 mm or greater than 0.5 mm or greater than 1 mm or greater than 2.5 mm.

A one-dimensional structural element or "fiber" is referred to herein as having a length much greater than the width and thickness. More specifically, in the present disclosure, the length of a one-dimensional structural element or fiber is greater than 2 times the width and thickness (e.g., the length is greater than 2 times the width and the length is greater than 2 times the thickness). This includes, but is not limited to a length greater than 3 times, or greater than 4 times, or greater than 5 times, or greater than 6 times, or greater than 8 times, or greater than 10 times, or greater than 12 times the width and thickness. Moreover, in some embodiments that are included but not limiting herein, the length of a fiber is greater than 0.3 mm or greater than 0.5 mm, or greater than 1 mm or greater than 2.5 mm.

A zero-dimensional structural element or "bead" is referred to herein as having a length and width of the order of the thickness. In the present disclosure, the length and width of a zero-dimensional structural element or bead are no greater than 2 times the thickness. This includes, but is not limited to a length and width no greater than 3 times, or no greater than 4 times the thickness. Furthermore, the thickness of a zero-dimensional element or bead is less than 2.5 mm.

Non-limiting shapes of elements include "sheets", "rods", "cylinders", "fibers", "particles", "beads", "polyhedra", "spheroids", "ellipsoids", clusters or combinations thereof, and so on. In preferred embodiments the elements are bonded or connected to each other to form a continuous solid structure or three dimensional structural framework.

Moreover, as used herein, the term "segment" or "segments" refers to a fraction of an element along the length and/or width of said element. By way of example but not by way of limitation, a "segment" of a fiber may comprise a fraction of said fiber along the length of said fiber.

In the context of the invention herein, drug release from a solid element (or a solid dosage form, or a solid matrix, or a drug-containing solid) refers to the conversion of drug (e.g., one or more drug particles, or drug molecules, or clusters thereof, etc.) that is/are embedded in or attached to the solid element (or the solid dosage form, or the solid matrix, or the drug-containing solid) to drug in a dissolution medium.

As used herein, the terms "dissolution medium", "physiological fluid", "body fluid", "dissolution fluid", "medium", "fluid", and "penetrant" are used interchangeably. They are understood as any fluid produced by or contained in a human body under physiological conditions, or any fluid that resembles a fluid produced by or contained in a human body under physiological conditions. Examples include, but are not limited to: water, saliva, stomach fluid, gastrointestinal fluid, saline, etc. at a temperature of 37° C. and a pH value adjusted to the relevant physiological condition.

Moreover, in the invention herein an excipient is referred to as "polymeric" if its molecular weight is greater than 1,000 g/mol. This includes, but is not limited to a molecular weight greater than 1,500 g/mol, or greater than 2,000 g/mol, or greater than 3,000 g/mol, or greater than 4,000 g/mol, or greater than 5,000 g/mol. A polymeric excipient is referred to as "absorptive of a dissolution fluid" if it transitions from solid to a fluidic or viscous medium upon contact with a physiological or dissolution fluid.

A viscous medium is referred to a viscous solution, viscous dispersion, or viscous mass having a shear viscosity much smaller than the "viscosity" of a solid, but much greater than the shear viscosity of the dissolution fluid. Thus, in some embodiments the shear viscosity of a viscous medium is much less than that of a solid but greater than 2, or greater than 4, or greater than 5, or greater than 6, or greater than 7, or greater than 8, or greater than 10, or greater than 12, or greater than 15 times the viscosity of the dissolution fluid.

In other embodiments a viscous medium is defined by a shear viscosity in the range 0.005-100,000 Pa·s. This includes, but is not limited to a shear viscosity in the range 0.01-100,000 Pa·s, or 0.01-10,000 Pa·s. In the invention herein, the "shear viscosity" is typically referred to as average shear viscosity in the shear rate range 1-100 1/s under physiological conditions.

Moreover, in a viscous medium the concentration of water-soluble (or water-absorptive) polymeric excipient is typically greater than the disentanglement concentration, $c_e^*$, but generally smaller than the solid/semi-dilute demarcation, $c_e^{**}$. Thus, a viscous medium is typically a semi-dilute solution or dispersion comprising at least entangled, water-soluble or water-absorptive polymer molecules that are dissolved in or fluidized (e.g., made fluidic or viscous) by a physiological fluid.

A hydrophilic surface composition is referred to herein as a solid surface (e.g., a solid surface composition or a composition of the surface of an element or elements) that is wettable by an aqueous physiological or body fluid under physiological conditions. A solid surface is "wettable by a fluid" if the contact angle of a droplet of said fluid on said solid surface in air is no more than 90 degrees. This includes, but is not limited to a contact angle of a droplet of said fluid on said solid surface in air no more than 80 degrees, or no more than 70 degrees, or no more than 60 degrees, or no more than 50 degrees, or no more than 40 degrees, or no more than 30 degrees. It may be noted that in some embodiments the contact angle may not be stationary. In this case, a solid surface may be understood "wettable by a fluid" if the contact angle of a droplet of said fluid on said solid surface in air is no more than 90 degrees at least 20-360 seconds after the droplet has been deposited on said surface. A non-limiting illustration of a droplet on a surface is presented in U.S. application Ser. No. 15/482,776 titled "Fibrous dosage form".

Scope of the Invention

It is contemplated that a particular feature described either individually or as part of an embodiment in this disclosure can be combined with other individually described features, or parts of other embodiments, even if the other features and embodiments make no mention of the particular feature. Thus, the invention herein extends to such specific combinations not already described. Furthermore, the drawings and embodiments of the invention herein have been presented as examples, and not as limitations. Thus, it is to be understood that the invention herein is not limited to these precise embodiments. Other embodiments apparent to those of ordinary skill in the art are within the scope of what is claimed.

By way of example but not by way of limitation, it is contemplated that compositions, systems, devices, methods, and processes of the claimed invention encompass variations and adaptations developed using information from the embodiments described herein. Adaptation and/or modification of the compositions, systems, devices, methods, and processes described herein may be performed by those of ordinary skill in the relevant art.

Furthermore, where compositions, articles, and devices are described as having, including, or comprising specific components, or where processes and methods are described as having, including, or comprising specific steps, it is contemplated that, additionally, there are compositions, articles, and devices of the present invention that consist essentially of, or consist of, the recited components, and that there are processes and methods according to the present invention that consist essentially of, or consist of, the recited processing steps.

Similarly, where compositions, articles, and devices are described as having, including, or comprising specific compounds and/or materials, it is contemplated that, additionally, there are compositions, articles, and devices of the present invention that consist essentially of, or consist of, the recited compounds and/or materials.

It should be understood that the order of steps or order for performing certain action is immaterial so long as the invention remains operable. Moreover, two or more steps or actions may be conducted simultaneously.

The mention herein of any publication is not an admission that the publication serves as prior art with respect to any of the claims presented herein. Headers are provided for organizational purposes and are not meant to be limiting.

DETAILED DESCRIPTION OF THE INVENTION

Figure 6:
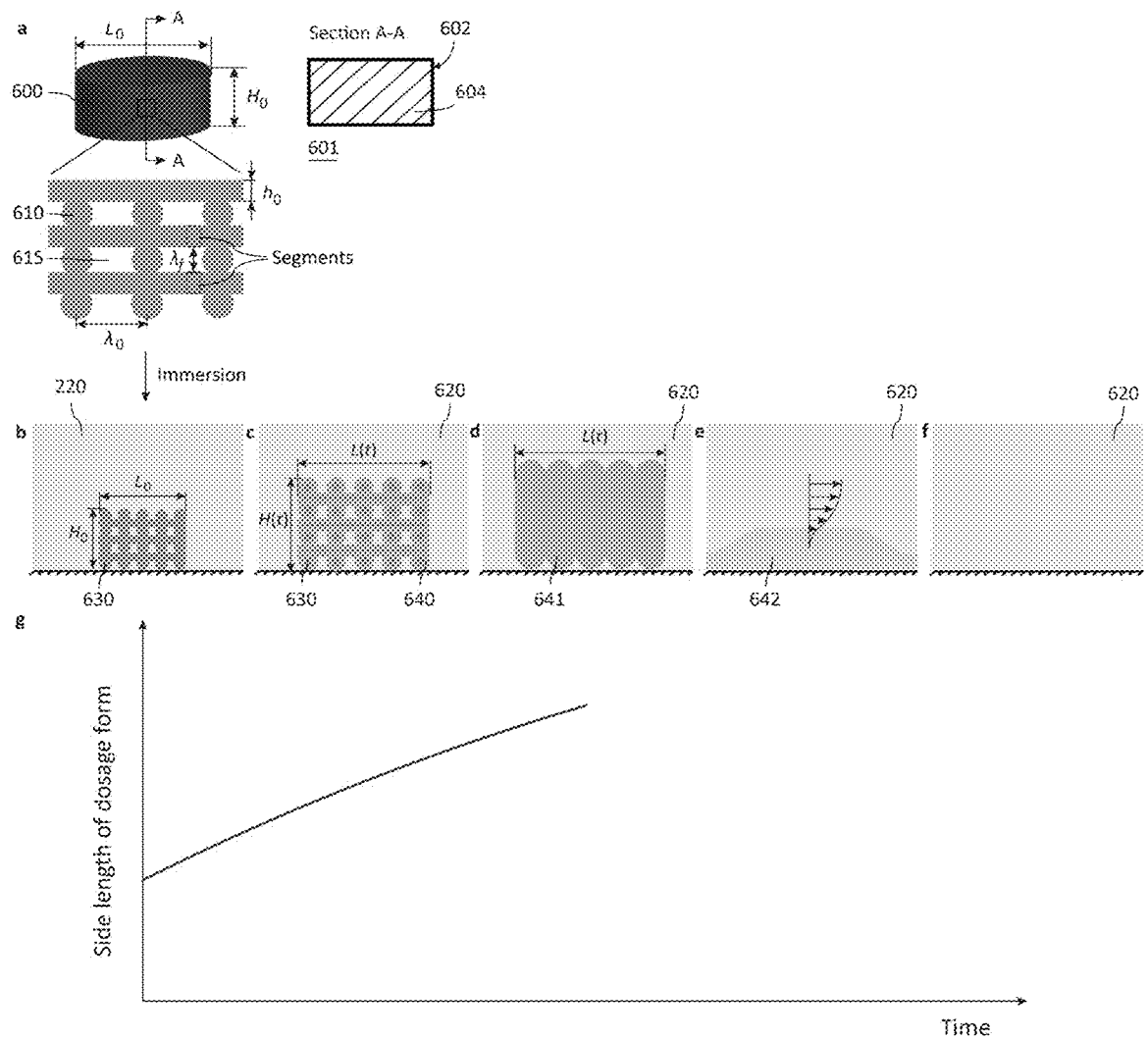
FIG. 6 presents a non-limiting example of a pharmaceutical dosage form according to the invention herein and the expansion, disintegration, and drug release processes upon immersion in a dissolution fluid: (a) dry dosage form and its microstructure, (b) dosage form and its microstructure immediately after immersion in a dissolution fluid, (c) dosage form and its microstructure while transitioning to a viscous medium, (d) dosage form and its microstructure after transitioning to a viscous medium, (e) deforming viscous medium in the dissolution fluid, (f) dissolution fluid after dosage form dissolution, and (g) sketch of the side length, L, of the dosage form versus time after immersion in a dissolution fluid.

FIG. 6a presents a non-limiting example of a pharmaceutical dosage form according to the invention herein. The dosage form 600 comprises a drug-containing solid 601 having an outer surface 602 and an internal structure 604 contiguous with and terminating at said outer surface 602. The internal structure 604 comprises a three dimensional structural framework of one or more thin, structural elements (e.g., fibers, sheets, etc.) 610. In the invention herein, a structural element is understood "thin" if its thickness (e.g., its smallest dimension) is much smaller than the length, or width, or thickness of the dosage form. This includes, but is not limited to a thickness smaller than one half, or smaller than one third, or smaller than one fourth, or smaller than one fifth of the length, or width, or thickness of the dosage form. Thin, structural elements are also referred to herein as "elements".

The elements 610 comprise at least an active ingredient, at least a polymeric excipient that is absorptive of a physiological fluid (e.g., an absorptive polymeric excipient), and at least a hydrophilic surface composition. The elements 610 further comprise segments separated and spaced apart from adjoining segments, thereby defining free spaces 615. A pluralitiy of adjacent free spaces 615 combine across the drug-containing solid 601 to define one or more interconnected free spaces 615 forming an open pore network in the drug-containing solid 601.

In the invention herein, the terms "interconnected free spaces" or "open pore network" in the drug-containing solid are also referred to as "interconnected pore network", "network of open channels", or "open channels of free space" in the drug-containing solid. In some embodiments, interconnected free space or interconnected free spaces is/are accessible from the outer surface of the drug-containing solid. That is, no walls (e.g., walls comprising the three dimensional structural framework of elements) must be ruptured to obtain an interconnected free space (e.g., an open channel of free space) from the outer surface of the drug-containing solid to a point (or to any point) in the interconnected free space within the internal structure. Moreover, it may be noted that if all free spaces (e.g., the entire free space in the drug-containing solid) is interconnected, the free space is also referred to herein as "contiguous". Dosage forms with contiguous free space comprise a preferred embodiment of this invention.

As shown in FIG. 6b, upon immersion in a dissolution fluid said open pore network permits percolation of physiological fluid 620 into the drug-containing solid 601, and enables uniform wetting of the structural framework by said fluid. In the invention herein, a surface (e.g., a surface of the three dimensional structural framework) is "wetted by a fluid" if said fluid contacts (e.g., is in contact with) said surface. A surface is "uniformly wetted" by a fluid if at least 30-60 percent of the area of said surface is in contact (e.g., in direct contact) with said fluid. In preferred embodiments, upon immersion of the drug-containing solid in a physiological fluid at least 70 percent of the surface of the three dimensional structural framework is wetted by (e.g., contacted by) said fluid.

The drug-containing solid with uniformly wetted three-dimensional structural framework (e.g., the wet elements 610 or wet drug-containing solid 601) then transitions from solid 630 to a viscous medium 640, 641, 642, thereby expanding in all dimensions as shown schematically in the non-limiting FIGS. 6c-6e.

It may be noted that the drug-containing solid may be a "solid", a combination of a "solid" and a "viscous medium", a "viscous medium", a combination of a "solid" and a dilute solution or dispersion, or a combination of a "viscous medium" and a dilute solution or dispersion while transitioning to a viscous medium. Moreover, the terms "expanding in all dimensions", "expand in all dimensions", or "expansion in all dimension" are understood as an increase in a length of a sample (e.g., the length, and/or width, and/or thickness, etc. of said sample) and an increase in volume of said sample. Thus, pure shear deformation is not considered "expansion in all dimensions" herein.

In some embodiments, upon immersion in a dissolution fluid the drug-containing solid dissolves or disintegrates in said physiological fluid. Moreover, in some embodiments the drug-containing solid dissolves or disintegrates in a physiological or body fluid during or after transitioning to a viscous medium.

In some embodiments, the drug-containing solid expands by the penetration (e.g., the diffusion or inflow) of physiological or body fluid into the three dimensional structural framework of elements. Furthermore, in some embodiments the drug-containing solid expands by the penetration (e.g., the diffusion or inflow) of physiological or body fluid into an absorptive polymeric excipient. Moreover, in some embodiments the drug-containing solid expands by the penetration (e.g., the diffusion or inflow) of physiological or body fluid into at least one structural element.

The expansion of the drug-containing solid can be quite substantial, as shown schematically in FIG. 6g. Thus, in some embodiments, at least one dimension of the drug-containing solid (e.g., a side length of the drug-containing solid, the thickness of the drug-containing solid, etc.) expands to at least 1.12 times the initial value (e.g., the initial length) while transitioning to a viscous medium 641, 642. This includes, but is not limited to at least one dimension of the drug-containing solid expanding to at least 1.15 times, or at least 1.17 times, or at least 1.2 times, or at least 1.22 times, or at least 1.25 times, or at least 1.27 times, or at least 1.3 times, or at least 1.35 times, or at least 1.4 times, or at least 1.5 times, or at least 1.6 times, or at least 1.7 times the initial value while transitioning to a fluidic or viscous medium 641, 642.

Furthermore, in some embodiments the drug-containing solid expands to at least 1.4 times its initial volume while transitioning to a viscous medium. This includes, but is not limited to a drug-containing solid that expands to at least 1.5 times, or at least 1.6 times, or at least 1.7 times, or at least 1.8 times, or at least 1.9 times, or at least 2 times, or at least 2.2 times its initial volume.

The rate of expansion generally depends on the rate at which dissolution fluid 620 is absorbed by the structural framework (e.g., by the absorptive polymeric excipient), and the presence and stringency of constraints to expansion. The absorption rate of dissolution fluid by the framework is typically increased if the specific surface area (e.g., the surface area to volume ratio) of the framework is increased. Thus, if the elements 630, 640 are thin, the surface area to volume ratio is large, and the rate at which dissolution fluid is absorbed by the framework should be fast.

Constraints to expansion often originate from non-uniformities in the dissolution fluid concentration across the three dimensional structural framework. By way of example but not by way of limitation, a wet element or segment may absorb dissolution fluid, but expansion of said wet element or segment may be constrained if it is connected (e.g., attached) to a dry solid element or segment that does not expand. Thus, to minimize constraints to expansion, uniform wetting of elements in the structural framework is crucial. Uniform wetting is enabled, among others, by interconnected free spaces (e.g., by interconnected free spaces forming an open pore network into which dissolution fluid may percolate).

The dosage forms according to the invention herein comprise a structural framework of thin elements with hydrophilic surface composition surrounded by interconnected free spaces that form an open pore network. Thus the expansion rate can be substantial.

In some embodiments, accordingly, at least one dimension (e.g., a side length or the thickness) of the drug-containing solid expands to at least 1.12 times the initial value (e.g., the initial length) as it transitions to a fluidic or viscous medium within no more than 30 minutes of immersion in a physiological or body fluid under physiological conditions. This includes, but is not limited to at least one dimension of the drug-containing solid reaching a length at least 1.12 times the initial length within no more than 20 minutes, or within no more than 15 minutes, or within no more than 10 minutes, or within no more than 5 minutes of immersion in a physiological or body fluid under physiological conditions. This also includes, but is not limited to at least one dimension of the drug-containing solid expanding to a length at least 1.15 times the initial length, or at least 1.2 times the initial length, or at least 1.25 times the initial length, or at least 1.3 times the initial length, or at least 1.4 times the initial length, or at least 1.5 times the initial length, or at least 1.6 times the initial length within no more than 20 minutes after immersion in a physiological or body fluid under physiological conditions.

Furthermore, in some embodiments the drug-containing solid expands to at least 1.4 times its initial volume within no more than 20 minutes of immersing in a physiological or body fluid under physiological conditions. This includes, but is not limited to a drug-containing solid that expands to at least 1.5 times, or at least 1.6 times, or at least 1.7 times, or at least 1.8 times, or at least 1.9 times, or at least 2 times, or at least 2.2 times its initial volume within no more than 20-30 minutes of immersing in a physiological or body fluid under physiological conditions.

During and after transitioning to a fluidic or viscous medium the three dimensional structural framework of elements and/or the viscous medium 640, 641, 642 may further release drug into the dissolution fluid. Common drug release processes include, but are not limited to erosion into the dissolution fluid 620 (FIGS. 6c-6f), diffusion of drug through the viscous medium, and so on.

It may be noted, furthermore, that a drug-containing solid or a viscous medium may expand and be diluted to such extent that it essentially forms a dilute solution or a dilute dispersion. A dilute solution or a dilute dispersion is referred to herein as a solution or dispersion of a physiologial fluid and dissolved, disentangled polymeric excipient molecules (e.g., dissolved polymeric excipient molecules at a concentration smaller than the disentanglement concentration). Such dilute solutions or dilute dispersions are generally deformable by and miscible with a physiological fluid. It should be noted, however, that any deformation due to the application of external forces, including but not limiting to shear stresses by the dissolution fluid, buoyancy, gravity, etc. does not comprise "expansion" herein. Moreover, a dilute solution or a dilute dispersion is not considered a "viscous medium" herein.

Finally, additional non-limiting examples of three dimensional structural frameworks with interconnected free spaces illustrating how the elements (e.g., fibers sheets, beads, etc.) may be structured, arranged, or assembled are disclosed in the co-pending U.S. application Ser. No. 15/482,776 titled "Fibrous dosage form", U.S. application Ser. No. 15/964,058 titled "Method and apparatus for the manufacture of fibrous dosage forms", and U.S. application Ser. No. 15/964,063 titled "Dosage form comprising two-dimensional structural elements". More examples of how the elements may be structured or arranged in the three dimensional structural network or framework of one or more elements would be obvious to a person of ordinary skill in the art. All of them are within the spirit and scope of this invention.

Modeling Dosage Form Disintegration, Expansion, and Drug Release

The following examples present ways by which the drug release and disintegration behavior of the disclosed dosage forms may be modeled. The models will enable one of ordinary skill in the art to more readily understand the details and advantages of the invention. The models are for illustrative purposes and are not meant to be limiting in any way.
a) Dosage Form Structure The non-limiting models presented refer to pharmaceutical dosage forms shown schematically in FIGS. 7a and 8a. The dosage forms 700, 800 comprise a drug-containing solid 701, 801 having an outer surface 702, 802 and an internal three dimensional structural framework 704, 804 comprising a plurality of criss-crossed stacked layers of fibrous structural elements 710, 810, said framework 704, 804 contiguous with and terminating at said outer surface 702, 802. The fibrous structural elements 710, 810 comprise at least a drug 780, 880, at least an absorptive polymeric excipient 790, 890, and a hydrophilic surface composition. The fibrous structural elements 710, 810 further have segments spaced apart from like segments of adjoining fibrous elements 710, 810, thereby defining free spaces, wherein a plurality of adjacent free spaces of successive layers combine to define one or more interconnected free spaces 715, 815 forming an open pore network in the drug-containing solid 701, 801. The radius of the fibrous structural elements 710, 810 or fiber segments and the inter-fiber spacing in a layer of fibrous structural elements are uniform.

b) Dosage Form Compositions

Two non-limiting dosage forms with different composition and drug release mechanism are considered. In the first 700, represented by FIG. 7 and referred to herein as "dosage form A", the fibers 710 consist of 10 wt % drug (ibuprofen), 60 wt % hydroxypropyl methyl cellulose (HPMC) with a molecular weight of 10 kg/mol (also referred to herein as "HPMC 10k"), and 30 wt % polyoxyl stearate. The surface of the fibers 710 is coated with a thin, hydrophilic layer of polyvinyl pyrrolidone (PVP) and silicon dioxide ($SiO_2$).

Figure 8:
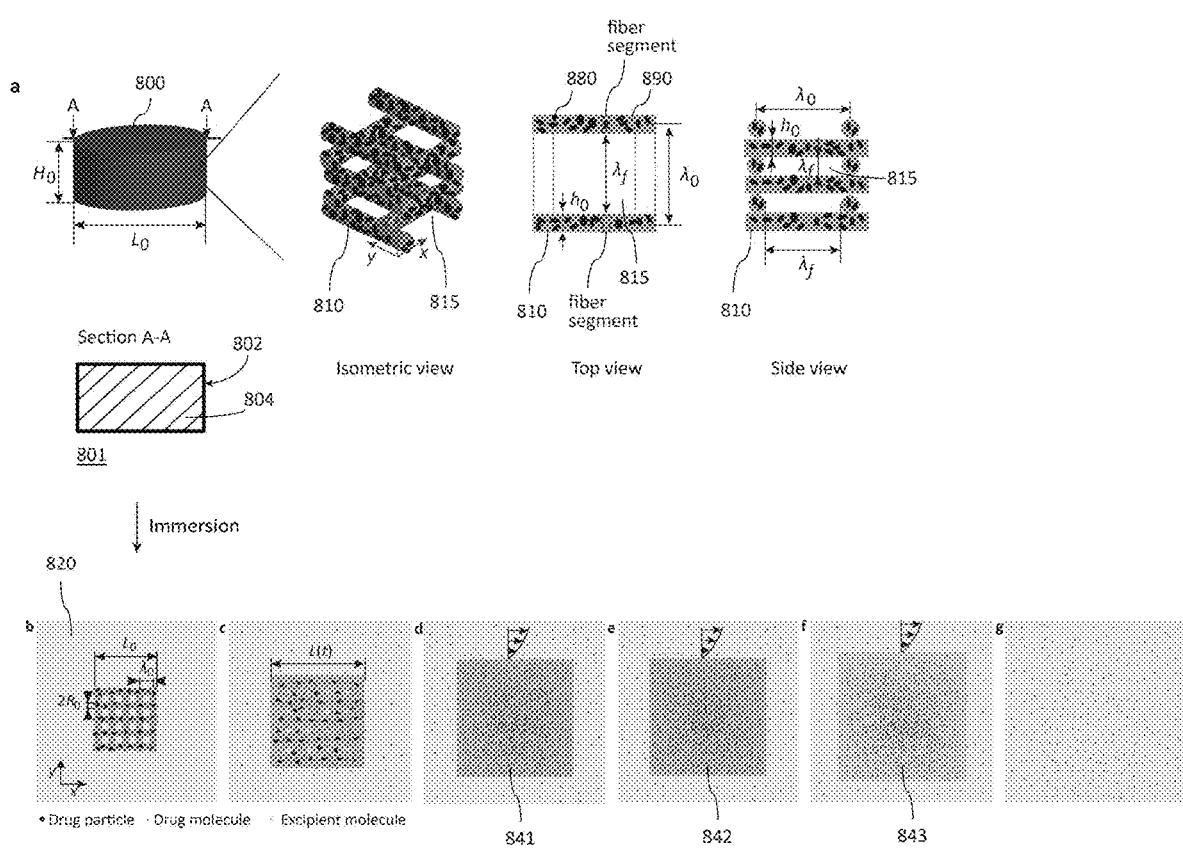
FIG. 8 presents a further non-limiting pharmaceutical dosage form according to the invention herein and the expansion, disintegration, and drug release processes after immersion in a dissolution fluid.

In the second dosage form 800, represented by FIG. 8 and referred to herein as "dosage form B", the fibers 810 consist of 20 wt % drug (acetaminophen) and 80 wt % of a high-molecular-weight polymeric excipient (HPMC with a molecular weight of 120 kg/mol, also referred to herein as "HPMC 120k"). Moreover, the surface of the fibers 810 is coated with a thin, hydrophilic layer of polyvinyl pyrrolidone (PVP) and silicon dioxide ($SiO_2$).

c) Overview of the Drug Release Mechanisms

Upon immersion of dosage form A in an aqueous dissolution fluid 720, the fluid 720 percolates rapidly into the interior of the structure because the void space 715 (e.g. the free space) is contiguous and the fiber surface hydrophilic (FIG. 7b). Moreover, as shown schematically in FIG. 7c, the fluid 720 (e.g., water, saliva, gastrointestinal fluid, etc.) then diffuses into the fibers 710. The thin fibers 710 and the structure transition from solid 730 to viscous 740 and expand rapidly as the fluid 720 diffuses in.

Moreover, as the fibers and the structure expand, dissolution fluid 720 continues to flow from the outside through the pores 716 into the structure (FIGS. 7c and 7d). Eventually, however, the fluid content in the dosage form will be so large and the viscosity of the expanded viscous medium 741, 742 so small that it deforms due to such forces as gravity, fluid shear, and so on (FIGS. 7d and 7e). Such deformation increases the surface area-to-volume ratio of the viscous medium 741, 742, and promotes its erosion and dissolution. The drug is released as the excipient surrounding the drug molecules or drug particles in the viscous medium 741, 742 dissolves or erodes. If the fibers 710 are thin, the diffusion length of the dissolution fluid 720 molecules is small, and the structure expands and dissolves rapidly.

For dosage form B, as shown schematically in FIGS. 8b and 8c the disintegration, expansion, and drug release processes 800 initially proceed as in the first case: percolation of dissolution fluid 820 to the interior, fiber-fluid interdiffusion, and expansion of the structure due to fluid absorption. However, because the fibers 810 expand faster radially than axially, they coalesce eventually and fluid flow into the interior ceases. The dosage form then forms a viscous mass 841 as shown in FIG. 8d, consisting of entangled high-molecular weight excipient molecules, drug, and dissolution fluid 820.

The viscous mass 841, 842, 843 erodes and dissolves very slowly (FIGS. 8d-8f). Thus the drug is released primarily by diffusion of drug molecules through the viscous mass 841, 842, 843. Because the viscous mass is several millimeters thick, however, the diffusion process is slow and the drug release time prolonged. After (and during) drug release the dissolution fluid continues to diffuse into the viscous mass 843 to make it more fluidic. Also, polymer molecules diffuse outwards from the viscous mass 843 into the dissolution fluid at the exterior. Thus the viscous mass 843 disappears or dissolves eventually (FIGS. 8f and 8g).

An in-depth analysis of any drug release mechanism or process is far beyond the scope of this disclosure. Herein, therefore, the individual process steps are decoupled and modeled with reasonable assumptions.

d) Percolation of dissolution fluid into the fibrous dosage forms

The first step of the dosage form disintegration and drug release processes herein is the percolation of dissolution fluid into the interior of the structure. Dissolution fluid percolation into the void space 715, 815 (e.g., the free space or free spaces) may be driven by capillary forces and be retarded by viscous forces. A rough estimate of the percolation time, $t_{perc}$, may be obtained if the free spaces 715, 815 are treated as a collection of capillary conduits exposed to the dissolution fluid at one end and to air at the other. For this case, the percolation time, $t_{perc}$, may be expressed by the Lucas-Washburn equation:

$$t_{perc} = \frac{2 l_{perc}^2 \mu_f}{\gamma r \cos\theta} \quad (1)$$

where $l_{perc}$ is the percolation length, r the radius of the capillary conduits, γ the tension of the air-dissolution fluid interface, and θ the contact angle.

For a non-limiting dosage form and dissolution fluid with parameters ($l_{perc}$=5 mm, $\mu_f$=0.001 Pa·s, γ=0.072 N/m, r=100 μm, θ≈30°), by Eq. (1) the percolation time, $t_{perc}$≈8 ms. In a fibrous structure 700, 800 the percolation time may not be quite as fast. Even so, if the fiber surface is hydrophilic and the free spacing, $\lambda_f$, greater than a few micrometers (e.g., if $\lambda_f$ is greater than about 5-10 μm), the interconnected free spaces 715, 815 should be percolated by the dissolution fluid 720, 820 almost immediately after immersion of the dosage form in said fluid.

It would be obvious to a person of ordinary skill in the art that the model presented (and any of the following models) are approximate and may not represent the underlying physical or chemical processes exactly. Furthermore, any model presented herein may be adapted to other situations, designs, or cases not specifically modeled herein. Thus, more examples and models of dissolution fluid percolation into the fibrous dosage forms obvious to a person of ordinary skill in the art are all within the scope of this disclosure.

e) Inter-Diffusion of Fibers and Dissolution Fluid

After dissolution fluid percolation through the dosage form structure (e.g., the open pore network defined by the interconnected free spaces), the hydrophilic coating on the fibers may dissolve. Then the dissolution fluid (e.g., water) and the excipient in the fibers may inter-diffuse.

Assuming that the water diffusivity in the fiber, $D_w$, is independent of the concentration, the differential equation for water diffusion in cylindrical coordinates is:

$$\frac{\partial c_w}{\partial t} = \frac{D_w}{r}\frac{\partial}{\partial r}\left(r\frac{\partial c_w}{\partial r}\right) \quad 0 \leq r \leq R(t) \tag{2a}$$

where $c_w(r,t)$ is the water concentration in the fiber and $R(t)$ the fiber radius at time t.

Figure 9:
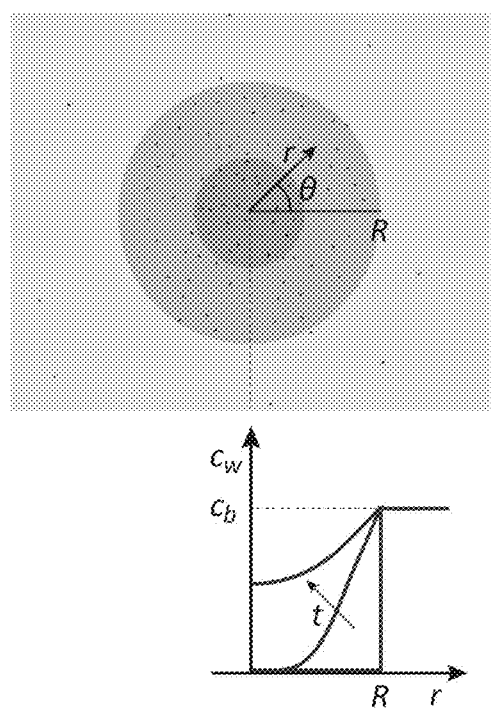
FIG. 9 shows non-limiting schematics of dissolution fluid diffusion into a fiber, and profiles of the fluid concentration in the fiber at different times.

Let the water concentration at the fiber-fluid interface be $c_b$. The initial and boundary conditions, as shown in FIG. 9, then are:

$$c_w = 0 \quad t=0, \; 0 \leq r < R_0 \tag{2b}$$

$$c_w = c_b \quad t \leq 0, \; r = R(t) \tag{2c}$$

where $R_0$ is the initial fiber radius.

It may be immediately noticed that this is a moving-boundary problem. An analytical solution of Eq. (2a) subject to the initial condition (2b) and the moving-boundary condition (2c) may not be available at present. However, under the highly approximate assumption that the concentration of diffusant is very small (i.e., the fiber radius is constant), the water concentration profile, as shown schematically in the non-limiting FIG. 9, is given by:

$$\frac{c_w}{c_b} = 1 - \frac{2}{R}\sum_{n=1}^{\infty}\frac{\exp(-D_w\alpha_n^2 t)J_0(r\alpha_n)}{\alpha_n J_1(R\alpha_n)} \tag{3}$$

where $J_0$ and $J_1$ are the Bessel functions of the first kind of order zero and one, respectively, and the $\alpha_n$'s are the roots of $$J_0(R\alpha_n) = 0 \tag{4}$$

Integrating Eq. (3) over the fiber volume gives the ratio of the water mass in the fiber per unit length at time t, $M_w(t)$, and that at infinite time, $M_{w,\infty}$. According to Crank, for small times (i.e., $t \ll R_0^2/D_w$):

$$\frac{M_w(t)}{M_{w,\infty}} \cong \frac{4}{\sqrt{\pi}}\left(\frac{D_w t}{R_0^2}\right)^{1/2} \tag{5}$$

From Eq. (5), the mass of water in the fiber reaches 63 percent of its "terminal" value in $$t_{dif} \cong 0.28\frac{R_0^2}{D_w} \tag{6}$$

For $R_0 \sim 100$ μm and $D_w \sim 3 \times 10^{-11}$ m$^2$/s, by Eq. (6) $t_{dif}$ is just 26 seconds. If the fiber radius, however, is increased to about 315 μm, $t_{dif}$ is an order of magnitude greater. Thus, the fibers should be thin (e.g., the fiber thickness should be of the order of a few to a few hundred micrometers) for fast interdiffusion of the fiber (e.g., the absorptive excipient) with the dissolution fluid.

For further information on diffusion models, see, e.g., J. Crank, The Mathematics of Diffusion, 2nd edn., Oxford University Press, 1975. More examples of models of dissolution fluid diffusion into the fibers would be obvious to a person of ordinary skill in the art. All of them are within the scope of this invention.

f) Expansion of the Fibrous Dosage Forms

As a substantial amount of dissolution fluid diffuses or penetrates into the fibers (or an absorptive polymeric excipient), the mass and volume of the fibers increase (e.g., the fibers swell or expand). The fibrous dosage form may swell or expand, too, as the individual fibers expand. An exact derivation of the dosage form expansion rate, however, is far beyond the scope of this disclosure. Rough estimations based on the expansion of a single fiber are made below.

f1) Single Fibers

Assuming no volume change upon mixing (e.g., upon penetration of dissolution fluid into a fiber or an absorptive polymeric excipient), the normalized difference between the fiber volume at time t, $V(t)$, and the initial fiber volume, $V_0$, is coupled to the normalized mass of dissolution fluid that penetrated into the fiber:

$$\frac{V(t) - V_0}{V_\infty - V_0} = \frac{M_w(t)}{M_{w,\infty}} \tag{7}$$

where $V_\infty$ is the fiber volume at "infinite" time.

Moreover, for small expansions (i.e., if the boundary concentration of the dissolution fluid, $c_b \ll \rho_w$, the density of the dissolution fluid) the normalized volumetric expansion of the fiber at "infinite" or "long" time is $$\frac{V_\infty - V_0}{V_0} = \frac{c_b}{\rho_w} \tag{8}$$

Combining Eqs. (5) and (7) and multiplying with Eq. (8) gives the normalized volumetric expansion of the fiber:

$$\frac{V(t) - V_0}{V_0} = \frac{4}{\sqrt{\pi}}\frac{c_b}{\rho_w}\left(\frac{D_w t}{R_0^2}\right)^{1/2} \tag{9}$$

From Eq. (9) the normalized volumetric expansion of the fiber is roughly proportional to the square-root of time and the reciprocal of the initial fiber radius.

Furthermore, for small, isotropic expansions the normalized radial and axial expansions are about a third of the volumetric expansion. Thus, from Eq. (9), for small times $$\frac{\Delta R}{R_0} \cong \frac{\Delta L}{L_0} \cong \frac{4}{3\sqrt{\pi}}\frac{c_b}{\rho_w}\left(\frac{D_w t}{R_0^2}\right)^{1/2} \tag{10}$$

where $\Delta R$ and $\Delta L$, respectively, are the changes in fiber radius and fiber length, and $L_0$ is the initial fiber length.

Similarly, for small, entirely anisotropic expansions in radial direction, the radial expansion is about half the volumetric expansion. Thus, for small times:

$$\frac{\Delta R}{R_0} \cong \frac{4}{2\sqrt{\pi}}\frac{c_b}{\rho_w}\left(\frac{D_w t}{R_0^2}\right)^{1/2} \tag{11a}$$

and $$\frac{\Delta L}{L_0} \sim 0 \quad (11b)$$

From Eqs. (10) and (11a) the normalized expansion of the fiber is roughly proportional to the square-root of time and the reciprocal of the initial fiber radius. Moreover, for the parameter values $c_b \sim 930$ mg/ml, $\rho_w = 1000$ mg/ml, $D_w \sim 3 \times 10^{-11}$ m$^{2/s}$, and $R_0 \sim 100$ μm, by Eq. (9) $\Delta R/R_0 = \Delta L/L_0 = 0.3$ at one minute. Thus, thin fibers that interdiffuse rapidly with the dissolution fluid may expand to a radius or length that is more than 30 percent greater than the initial value within just a few minutes.

It should be noted again, however, that the accuracy of the above models is very limited. By way of example but not by way of limitation, Eqs. (3)-(11) assume that the boundary concentration, $c_b \ll \rho_w$, the water or dissolution fluid density. This assumption is generally not satisfied if the excipient and the dissolution fluid (e.g., water) are mutually soluble.

Any other models of single fiber expansion obvious to a person of ordinary skill in the art are all within the scope of this invention.

f2) Dosage Forms

Figure 10:
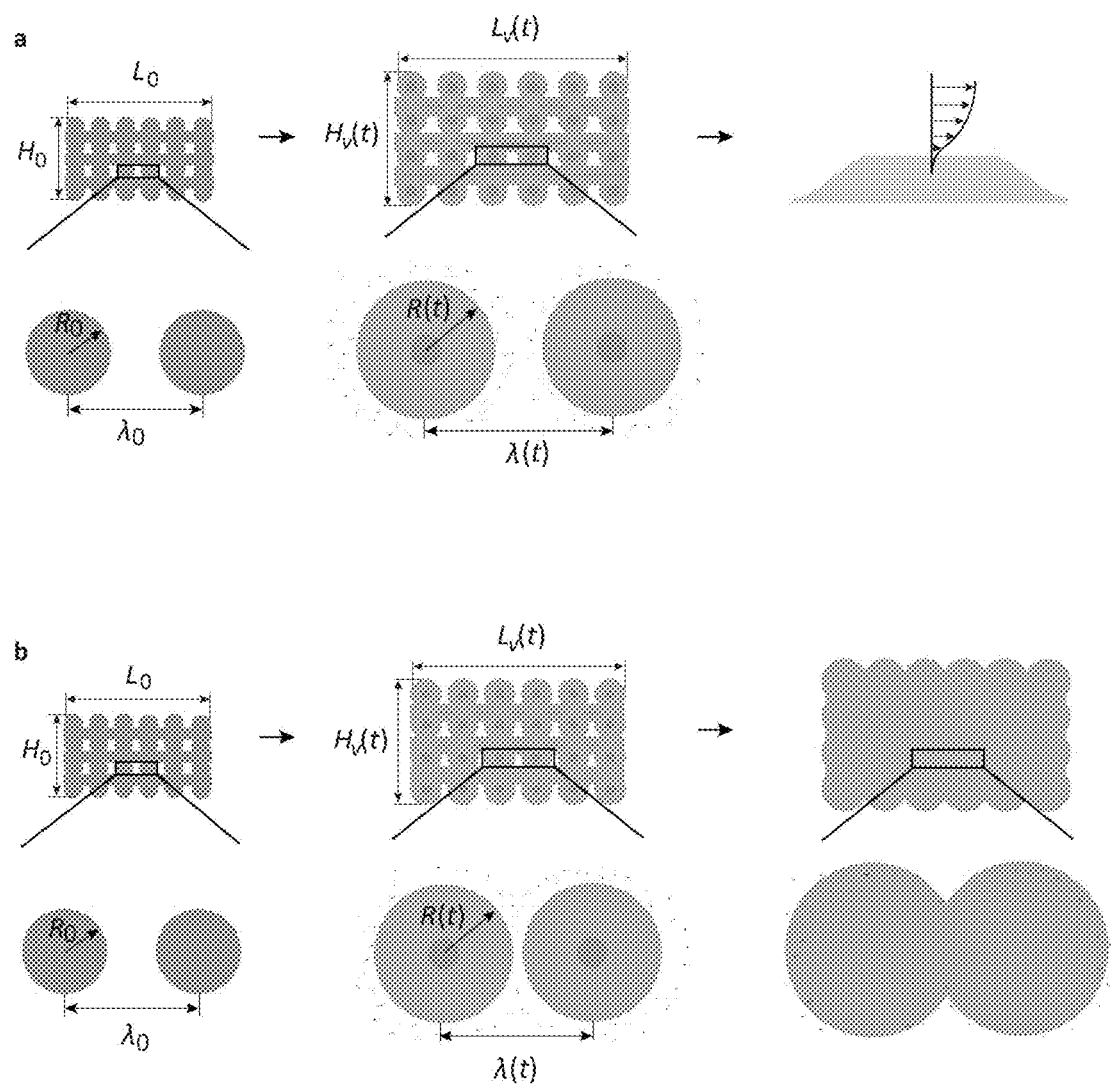
FIG. 10 depicts non-limiting schematics of expanding dosage form frameworks according to the invention herein with (a) isotropically expanding fibers and (b) anisotropically expanding fibers.

FIG. 10 schematically presents sections of fibers in the fibrous structures initially (before immersion in a dissolution fluid) and after immersion in a dissolution fluid.

For structures of isotropically expanding fibers, as shown in FIG. 10a, geometric similarity of the structure is preserved upon expansion. Thus, dissolution fluid continues to flow into the interior as the structure expands and is readily available around all expanding fibers. The length, $L_v$, and thickness, $H_v$, of the viscous, expanding dosage form then increase at the same rate as the radius or length of the single fiber. Thus, $$\frac{\Delta L_v}{L_0} \cong \frac{\Delta H_v}{H_0} \cong \frac{4}{3\sqrt{\pi}} \frac{c_b}{\rho_w} \left(\frac{D_w t}{R_0^2}\right)^{1/2} \quad (12)$$

Eventually, however, the water content in the fibers may be so large, and the viscosity of the fibers so small, that the structure may collapse or deform. The dosage form may then form a viscous medium, or even a dilute solution or a dilute dispersion, that ceases to expand and erodes or dissolves into the dissolution fluid.

For anisotropically expanding fibers in a cross-ply structure, as shown schematically in FIG. 10b, the normalized expansion of the inter-fiber distance may grow slower, but roughly in proportion to the normalized expansion of the fiber radius. The normalized longitudinal expansion, $\Delta L_v/L_0$, of the viscous, expanding dosage form may then be written as:

$$\frac{\Delta L_v}{L_0} \cong a \times \frac{\Delta R}{R_0} \cong a \times \frac{2}{\sqrt{\pi}} \frac{c_b}{\rho_w} \left(\frac{D_w t}{R_0^2}\right)^{1/2} \quad (13)$$

where α is a constant, typically between 0 and about ⅔. The longitudinal expansion rate of a dosage form with anisotropically expanding fibers is typically less than that of a dosage form with isotropically expanding fibers. Furthermore, if the fiber radius increases faster than the inter-fiber distance, the neighboring anisotropically expanding fibers may touch and coalesce eventually. This may cease (or reduce) the flow of dissolution fluid into the interior. The dosage form may form a viscous mass (or a viscous medium with entangled, concentrated polymer molecules) that ceases to expand (or expands at a much slower rate).

Further models of dosage form expansion during transition to a viscous medium would be obvious to a person of ordinary skill in the art. All of them are within the scope of this invention.

g) Formation of a Viscous Medium

As described above, the solid dosage form may transition to a viscous medium during expansion. A rough estimate of the viscosity of the medium is determined by the concentration, $c_{e,v}$, of the predominant polymeric excipient. By way of example but not by way of limitation, the predominant polymeric excipient can be the polymeric excipient with the greatest contribution to the viscosity of the viscous medium, or the polymeric excipient with the greatest molecular weight, or the polymeric excipient with the greatest concentration in the viscous medium, etc. In the non-limiting dosage forms A and B modeled herein, $c_{e,v}$ is typically the concentration of HPMC in the viscous medium. $c_{e,v}$ may be expressed as:

$$c_{e,v} = \frac{M_e}{V_v} \quad (14)$$

where $M_e$ is the mass of the predominant polymeric excipient (e.g., HPMC) in the dosage form and $V_v$ the volume of the viscous medium.

The mass of excipient is the product of the weight fraction of excipient in the solid dosage form, $w_e$, and the weight of the solid dosage form, $M_{sdf}$:

$$M_e = w_e M_{sdf} \quad (15a)$$

Furthermore, $M_{sdf}$ may be written in terms of the density, $\rho_s$, and volume fraction, $\varphi_s$, of the solid material in the dosage form as:

$$M_{sdf} = \rho_s \varphi_s V_{sdf} \quad (15b)$$

where $V_{sdf}$ is the volume of the solid dosage form. Combining Eqs. (15a) and (15b) gives:

$$M_e = w_e \rho_s \varphi_s V_{sdf} \quad (15b)$$

Similarly, the volume of the viscous medium may be expressed as:

$$V_v = V_{sdf}(1 + \Delta V_v/V_{sdf}) \quad (16a)$$

where $\Delta V_v = V_v - V_{sdf}$, the difference between the volume of the viscous medium and that of the solid dosage form. If the dosage form expanded isotropically, for small expansions $$V_v = V_{sdf}(1 + 3\Delta L_v/L_0) \quad (16b)$$

where $\Delta L_v/L_0$ may be obtained from either Eq. (12) or Eq. (13).

Combining Eqs. (15) and (16) with Eq. (14) the concentration of excipient in the viscous medium is:

$$c_{e,v} = \frac{w_e \varphi_s}{1 + 3\Delta L_v/L_0} \rho_s \quad (17)$$

Thus, the concentration of the predominant polymeric excipient in the viscous medium greatly depends on the extent by which the dosage form expands upon transitioning to a viscous medium. The concentration of the predominant polymeric excipient (e.g., an absorptive, polymeric excipient) in the viscous medium is smaller if the expansion of the viscous medium is greater.

For the non-limiting parameters of dosage form A, $w_e$~0.6, $\varphi_s$~0.5, $\Delta L_v/L_0$~0.5, and $\rho_s$~1200 mg/ml, by Eq. (17) $c_{e,v}$~144 mg/ml. This is only about twice the disentanglement concentration, $c_e^*$, derived in the non-limiting experimental example 11a. Thus the viscous medium is fairly dilute. Moreover, a viscous solution of water and 144 mg/ml HPMC 10k has a viscosity of about 598 mPa (see, e.g., experimental example 11a). This is only about two to three orders of magnitude greater than the viscosity of water.

For the non-limiting parameters of dosage form B, $w_e$~0.8, $\varphi_s$~0.4, $\Delta L_v/L_0$~1, and $\rho_s$~1200 mg/ml, by Eq. (17) $c_{e,v}$~96 mg/ml. This is about two orders of magnitude greater than the disentanglement concentration, $c_e^*$, derived in the non-limiting experimental example 11b. Thus the viscous medium is concentrated. Furthermore, a viscous solution of water and 96 mg/ml HPMC 120k has a viscosity of about $1.45 \times 10^3$ Pa·s (see, e.g., experimental example 11b). This is more than six orders of magnitude greater than that of water.

More examples and models of the viscous medium would be obvious to a person of ordinary skill in the art. All of them are within the scope of this disclosure.

h) Viscous Deformation of the Viscous Medium

Figure 11:
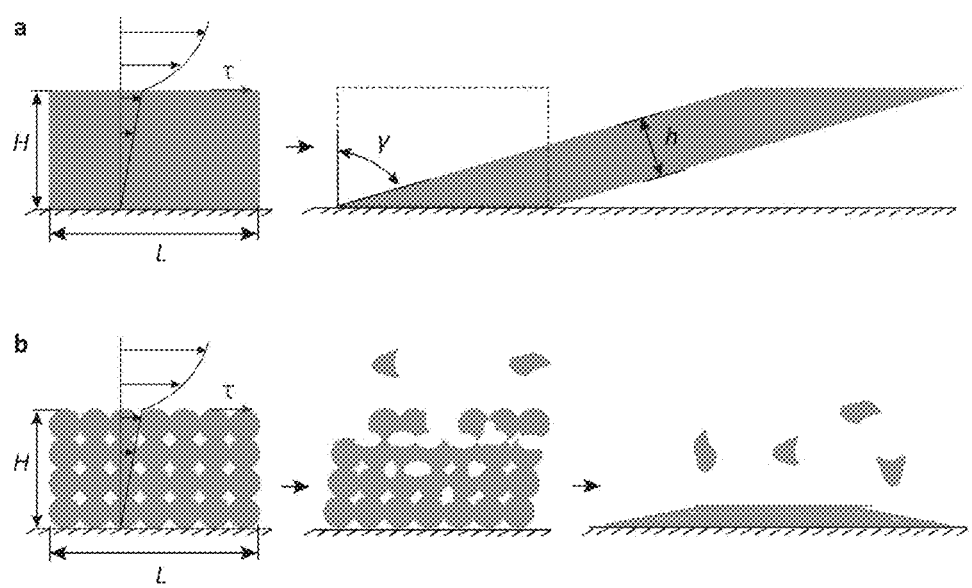
FIG. 11 presents non-limiting examples of the deformation process of viscous media: (a) uniform medium with uniform shear stress and strain, and (b) non-uniform medium with non-uniform stresses and strains.

The viscous medium is exposed to such forces as gravity or shear due to fluid flow. Thus it may deform with time. The derivation of accurate expressions for the shear stresses, strain rates, and strains in the medium is far beyond the scope of this disclosure. If the viscous medium, however, is fixed at the bottom and exposed to a unidirectional stream of a Newtonian fluid, as shown schematically in FIG. 11, the average wall shear stress, $\tau$, may be approximated by:

$$\tau = 0.664 v_\infty^{3/2} \sqrt{\frac{\rho_f \mu_f}{L_v}} \tag{18}$$

where $v_{28}$ is the far-field velocity of the fluid stream and $L_v$ the "length" of the viscous medium. Using the non-limiting parameters $v_{28}$=5 mm/s, $\rho_f$=1000 kg/m³, $\mu_f$=0.001 Pa·s, and $L_v$=10 mm, the shear stress acting on the surface of the viscous medium, $\tau$=2.3×10$^{-3}$ Pa.

Assuming that the viscous medium is Newtonian viscous, the shear strain rate is about:

$$\dot{\gamma} = \frac{\partial v}{\partial z} = \frac{\tau}{\mu_v} \tag{19}$$

where $\mu_v$ is the shear viscosity of the viscous medium.

Furthermore, if the viscous medium is homogeneous, viscous flow may thin it down to a sheet as shown in the non-limiting schematic of FIG. 11a. From geometry the time, $t_{def}$, to thin the medium down to a sheet of thickness h may be written as:

$$t_{def} = \frac{\arccos(h/L_v)}{\dot{\gamma}} \tag{20a}$$

Substituting Eq. (18) in Eq. (19b) gives:

$$t_{def} = \frac{\mu_v}{\tau} \times \arccos\left(\frac{h}{L_v}\right) \tag{20b}$$

For representative parameters of medium A ($\tau$=2.3×10$^{-3}$ Pa, $L_v$=10 mm h=200 μm, and $\mu_v$=598 mPas) by Eq. (19b) $t_{def}$=6.6 minutes. For representative parameters of medium B ($\tau$=2.3×10$^{-3}$ Pa, $L_v$=10 mm h=200 μm, and $\mu_v$=1.45×10$^3$ Pas) $t_{def}$=266 hours. Thus the viscous medium A deforms very rapidly, whereas the viscous medium B deforms very slowly. It should be noted, however, that the calculated $t_{def}$ for medium B may not be of any practical relevance. At such slow deformation rates dissolution fluid may diffuse into the viscous medium to make it less viscous and accelerate its deformation rate with time.

Another non-limiting example of a deforming viscous medium is shown in FIG. 11b. The viscous medium is heterogeneous comprising higher-viscosity regions at the original fiber locations and lower-viscosity regions between fibers. Thus the stresses, strain rates, and strains may be heterogeneous, too; low-viscosity areas may shear faster than the rest leading to void growth. Eventually, the voids may coalesce and the structure may break up. The rate at which the structure may break up increases greatly if the strain rate increases and the viscosity of the viscous medium decreases (e.g., if the concetration of the predominant polymeric excipient in the viscous medium decreases).

More examples and models of the deformation of the viscous gel consistency solution (e.g., the viscous medium) obvious to a person of ordinary skill in the art are all within the scope of this disclosure.

i) Erosion of the Viscous Medium By Convective Mass Transfer

Concomitant with the viscous deformation, the viscous medium and the dissolution fluid may continue to interdiffuse. Thus, because the shear strain rate in the surrounding dissolution fluid is generally far greater than in the viscous medium, for the purpose of estimating the erosion rate by convective diffusion the viscous medium may be considered a "stagnant" body.

In convective diffusion the erosion rate of the viscous medium may be approximated by that of a rotating, solid disk as:

$$E = -\frac{dh}{dt} = 0.62 \left(\frac{c_e^*}{c_{e,v}}\right)\left(\frac{\mu_f}{D_e \rho_f}\right)^{1/3} \left(\frac{D_e^2 \rho_f \Omega}{\mu_f}\right)^{1/2} \tag{21}$$

where h is the thickness of the viscous medium, $\mu_f$ the viscosity of the dissolution fluid, and $\Omega$ the rotation rate.

The time to erode the viscous medium, $$t_{E,v} = \frac{h_0}{E} \tag{22}$$

where $h_0$ is the initial thickness.

For representative parameter values of medium A ($\mu_f$=0.001 Pa·s, $D_e$~10$^{-10}$ m²/s, $\rho_f$=1000 mg/ml, $\Omega$=50 rpm, $c_{e,v}$=144 mg/ml, and $c_e^*$=70 mg/ml) the erosion rate, E~1.5 μm/s. Thus a 200 μm thick film of this medium dissolves in about 2 minutes. For representative parameter values of medium B ($\mu_f$=0.001 Pa·s, $D_e$~10$^{-10}$ m²/s, $\rho_f$=1000 mg/ml, $\Omega$=50 rpm, $c_{e,v}$=96 mg/ml, and $c_e^*$=1.67 mg/ml) E~0.053 μm/s. About 63 minutes would be required to erode a thickness of just 200 μm. Moreover, a 5 mm thick viscous medium of this composition eroding from two sides would dissolve in 63×2.5/0.2=788 minutes (13 hours).

More examples and models of erosion or dissolution of the drug-containing solid or viscous medium obvious to a person of ordinary skill in the art are all within the scope of this disclosure.

j) Drug Release

The drug may be released from the viscous medium into the dissolution fluid by either erosion of the viscous medium (e.g., by erosion or dissolution of the excipient surrounding drug molecules or drug particles in the viscous medium) or by diffusion of drug molecules through the viscous medium into the dissolution fluid. The faster mechanism of these two is typically referred to herein as "dominant drug release mechanism".

j1) Drug Release by Erosion of the Viscous Medium

The time to release the drug by erosion may be approximated as:

$$t_{d,er} = t_{perc} - t_{dif} + t_{def} + t_{E,v} \qquad (23)$$

For the relevant parameter values of dosage form A ($t_{perc}$~1 s, $t_{dif}$~26 s, $t_{def}$~6.6 min $t_{E,v}$~2 min) the drug release time by erosion, $t_{d,er}$≈9.1 min. For dosage form B, however, $t_{d,er}$ would be more than 10 hours.

More models and examples to estimate the drug release time obvious to a person of ordinary skill in the art are all within the scope of this disclosure.

j2) Drug Release by Drug Diffusion Through the Viscous Medium

Figure 12:
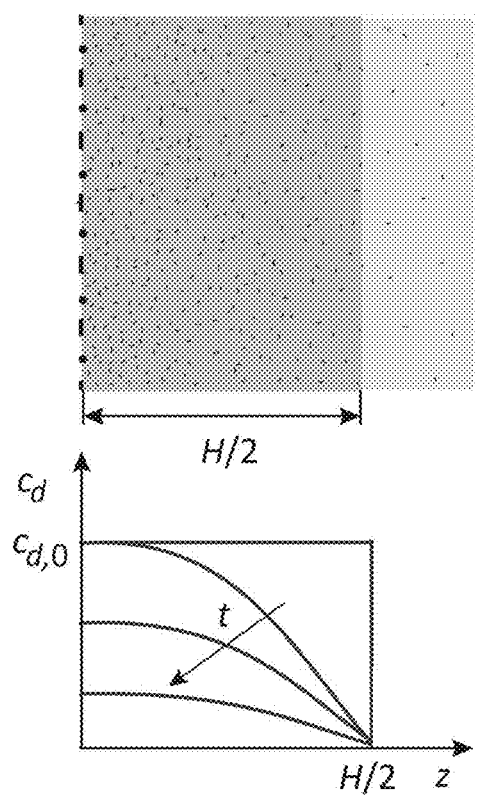
FIG. 12 is a non-limiting schematic illustration of drug release by diffusion of drug molecules through a viscous mass or medium.

Drug release from a viscous mass governed by the diffusion of drug molecules through it is illustrated schematically in FIG. 12. If all drug is dissolved in the viscous mass the diffusion equation may be expressed as:

$$\frac{\partial c_d}{\partial t} = D_d \frac{\partial^2 c_d}{\partial z^2} \; -H/2 \leq z \leq H/2 \qquad (24a)$$

subject to the initial and boundary conditions:

$$c_d = c_{d,0} \; t=0, \; -H/2 < z < H/2 \qquad (24b)$$

$$c_d = 0 \; t \geq 0, \; z = H/2 \qquad (24c)$$

$$c_d = 0 \; t \geq 0, \; z = -H/2 \qquad (24d)$$

where $c_d$ is the concentration of drug molecules in the viscous mass, $D_d$ the diffusivity of drug molecules in the viscous mass, and H the thickness of the viscous mass.

From the solution to Eqs. (24a)-(24d) given by Crank, for small times the fraction of drug released may be approximated as:

$$\frac{m_d(t)}{M_0} \cong \frac{4}{\pi^{1/2}} \left( \frac{D_d t}{H^2} \right)^{1/2} \qquad (25)$$

Eq. (25) suggests that the fraction of drug released by the viscous mass is proportional to the square-root of time and inversely proportional to its thickness. For $D_d$~5×10$^{-10}$ m$^2$/s, H=5 mm eighty percent of the drug content is released in 105 minutes. This is too long for immediate-release applications.

For more examples and models of drug release by diffusion of drug molecules through a viscous medium, see, e.g., J. Siepmann, N. A. Peppas "Modeling of drug release from delivery systems based on hydroxypropyl methylcellulose (HPMC)" Advanced Drug Delivery Reviews 48 (2001) pp. 139-157. More examples and models of drug release by diffusion of drug molecules through a viscous medium obvious to a person of ordinary skill in the art are all within the spirit and scope of this disclosure.

k) Summary of Models

The above models suggest that upon immersion of the disclosed dosage form in a dissolution fluid, the fluid percolates uniformly and rapidly into the interior of the structure provided the surface of the fibers (e.g., the surface of the elements) is hydrophilic, the free spaces are interconnected, and the free spacing (e.g., the effective free spacing) is at the micro- or meso- or macro-scale.

After percolation, the fluid diffuses from the surface of the fiber inward. As a result, the fiber absorbs water and transitions to a viscous or gel-like substance or medium. Moreover, upon water absorption the fibers expand. Thus, if constraints that hold up expansion of the dosage form structure, such as non-uniform wetting and so on are eliminated, the fibrous structure may expand roughly in proportion to the expansion rate of a single fiber. Two non-limiting types of single fiber and dosage form expansion may be differentiated.

In the first, the single fibers expand isotropically. The fibrous structure then expands at roughly the same rate as the single fiber, geometric similarity of the structure is preserved during expansion, and the pore network remains open. Thus, dissolution fluid continues to flow into the structure during expansion, and the absorptive polymeric excipient in the viscous medium (or structural framework, or viscous framework) is ever diluted. As a result, the viscosity of the viscous medium is ever decreasing, until it is so small that the medium readily deforms and dissolves. Dosage forms with this type of fibers generally dissolve rapidly, even if the fibers are tightly packed and loaded with large amounts of a water-soluble or water-absorptive polymeric excipient.

In the second, the single fibers expand anisotropically. If the fibers expand faster radially than longitudinally, they may coalesce as the dosage form expands. The free spaces and open pores may close out after fiber coalescence, and the dissolution fluid flow into the interior may be stopped or greatly reduced. As a result, an expanded, viscous mass of far greater polymeric excipient concentration and viscosity may be formed. The viscous mass may not or very slowly deform or dissolve in the dissolution fluid. Drug may be released by the slow diffusion of drug molecules through the thick viscous mass. This is not optimal for immediate-release applications.

Embodiments of the Invention

In view of the theoretical models and considerations above, which are suggestive and approximate rather than exact, the design and embodiments of the dosage forms disclosed herein may further comprise the following.

a) Drug-Containing Solid and Three Dimensional Structural Framework of Elements

In some embodiments, the average length, average width, and/or average thickness of the drug-containing solid (e.g., the three dimensional structural framework of one or more elements) is/are greater than 1 mm. This includes, but is not limited to an average length, and/or average width, and/or average thickness of the drug-containing solid greater than 1.5 mm or greater than 2 mm or in the ranges 1 mm-30 mm 1.5 mm-30 mm or 2 mm-30 mm. In the invention herein, the length is usually referred to a measure of distance in direction of the longest distance, the thickness is usually referred to a measure of distance in direction of the shortest distance, and the width is smaller than the length but greater than the thickness.

In some embodiments, the open pore network is contiguous so that no walls (e.g., walls comprising the three dimensional structural framework of elements) must be ruptured to obtain an interconnected cluster of free space (e.g., an open channel of free space) from the outer surface of the drug-containing solid to a point (or to any point) in the free space within the internal structure.

In some embodiments, however, at least one free space is enclosed by walls to form a closed cell. In this case, less than five walls may be ruptured to obtain an interconnected cluster of free space from the outer surface of the drug-containing solid to any point in the internal structure.

In some embodiments, the three-dimensional structural framework of elements comprises a continuous structure. Moreover, in some embodiments herein the three dimensional structural framework may comprise inter-element contacts (e.g., contacts between one element and another element, such as inter-fiber contacts, etc.). Such inter-element contacts include, but are not limited to point contacts or line contacts (for further information related to point contacts and line contacts, see, e.g., K. L. Johnson, "Contact mechanics", Cambridge University Press, 1985, or U.S. application Ser. No. 15/482,776 titled "Fibrous dosage form").

The inter-element contacts may provide mechanical support to the framework (e.g., a three dimensional structural network of one or more fibers). They may, however, also hold up disintegration and dissolution of the framework upon immersion in a dissolution medium. Thus, in some embodiments the number of inter-element (e.g., the number of inter-fiber) contacts in a dosage form, and/or at least one position of an inter-element (e.g., inter-fiber) contact in a dosage form, and/or a contact width of at least one inter-element (e.g., inter-fiber) contact in a dosage form is/are precisely controlled in the three dimensional structural framework. This includes, but is not limited to embodiments wherein the position of a fraction of the inter-fiber contacts is precisely controlled, said fraction being greater than 0.3 or greater than 0.5. This further includes, but is not limited to embodiments wherein the contact width of a fraction of the inter-fiber contacts is precisely controlled, said fraction being greater than 0.3 or greater than 0.5. Moreover, it may be noted that bonded point contacts generally enable both: a continuous structural framework (e.g., with densely-packed elements) of acceptable mechanical strength and interconnected void or pore space, so that upon immersion dissolution fluid can flow through the void or pore space and around the elements to wet the elements uniformly. Point contacts between elements or segments, and more specifically point contacts with a contact width no greater than 2.5 mm (e.g., no greater than 2 mm or no greater than 1.5 mm or no greater than 1.25 mm or no greater than 1 mm) are therefore preferred herein.

In some embodiments, one or more elements or one or more segments of an element are bonded to one or more other elements or one or more segments of other elements by diffusion of molecules from the one or more elements or the one or more segments to the other elements or the other segments. In that case, the one or more elements or segments are referred to herein as "diffusion-bonded" to the other elements or segments. In some embodiments, bonding is at an inter-element contact (e.g., at an inter-fiber contact). In other words, in some embodiments, two elements or two segments are bonded at an inter-element contact.

Moreover, an element or a segment in the three dimensional structural framework of one or more elements may, for example, be defined by its position (e.g., the position of its center of mass, or the position of its central axis, or the pathway of the line formed by its central axis, or the central plane, etc.) relative to a reference point or frame. In the invention herein, a reference frame may be understood as a reference coordinate system. The reference point or the origin and orientation of the reference frame may be specified on the outer surface or within the internal structure of the drug containing solid.

In some embodiments, the position of at least one element or at least one segment in the three dimensional structural framework of one or more elements is precisely controlled. Such embodiments include, but are not limited to three dimensional structural frameworks of one or more elements wherein the position of a fraction of the elements or segments is precisely controlled. The volume fraction of elements or segments (with respect to the total volume of elements or segments that make up the three dimensional structural framework of one or more elements) of which the position is precisely controlled can be greater than 0.1, or greater than 0.3, or greater than 0.5, or greater than 0.7, or greater than 0.9.

In the context of the invention herein, a variable or a parameter (e.g., the position of an element, or a spacing between elements, or an element thickness, etc.) is precisely controlled if it is deterministic and not stochastic (or random). A variable or parameter may be deterministic if, upon multiple repetitions of a step that includes said variable (e.g., if multiple dosage forms are produced under identical or almost identical conditions), the standard deviation of the values of said variable is smaller than the average value. This includes, but is not limited to a standard deviation of the values of said variable smaller than half the average value, or smaller than one third of the average value, or smaller than a quarter of the average value, or smaller than one fifth or the average value, or smaller than one sixth of the average value of said variable.

In some embodiments, furthermore, at least one spacing between elements or segments, $\lambda$, and/or at least one element thickness, h, is/are precisely (or deterministically) controlled. Thus, in some embodiments herein, if an element is produced multiple times under identical or almost identical conditions, the standard deviation of the thickness of said elements is less than the average value of said elements' thickness. Similarly, in certain embodiments if a spacing between elements or segments is produced multiple times under identical or almost identical conditions, the standard deviation of said spacing between elements or segments is less than the average value. We may note that the spacing between elements or segments may change along the length or width of said elements or segments. Similarly, the thickness of an element or a segment may change along the length of said element or segment.

A non-limiting example of a three dimensional structural framework of one or more elements wherein the position of a large fraction of (or all) the elements, the spacing between the elements, and the element thickness, are controlled (or precisely controlled) is an ordered structure.

By way of example but not by way of limitation, such regular or ordered structures may comprise multiple layers of fibers or fiber segments that are stacked. Moreover, the fibers or fiber segments in a layer can be oriented parallel (or almost parallel) to each other. The distance between neighboring fiber segments across the free space, also referred to herein as "$\lambda$" or "$\lambda_o$", may further be constant or essentially constant in a layer.

Figure 7:
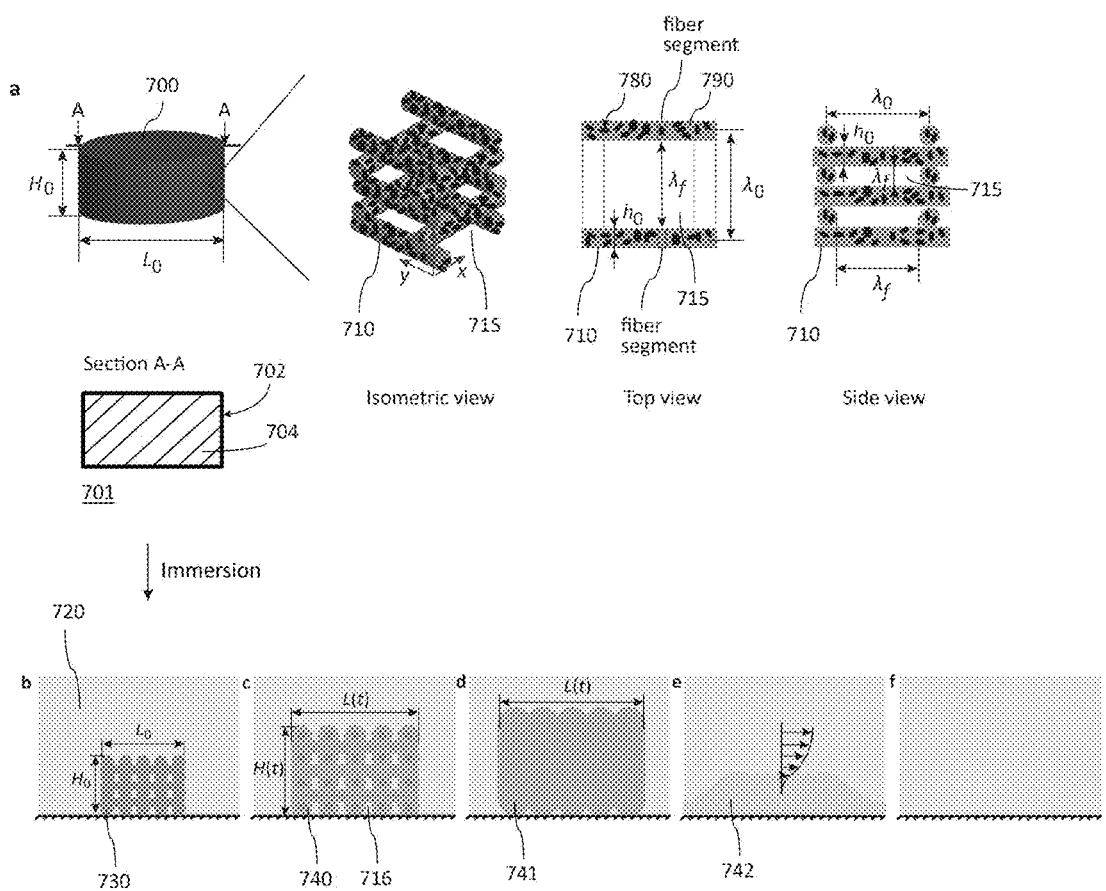
FIG. 7 illustrates another non-limiting pharmaceutical dosage form according to the invention herein and the expansion, disintegration, and drug release processes after immersion in a dissolution fluid.

It should be mentioned, furthermore, that a preferred embodiment of an ordered structure herein comprises plies (e.g., layers) of fibers or fiber segments that are stacked in a cross-ply arrangement (e.g., criss-crossed stacked layers of fibrous structural elements). In cross-ply arrangements, fibers (or fiber segments) in a layer (or ply) are oriented transversely or at an angle (e.g., at an angle greater than 0 degrees, or at an angle greater than 0 degrees but no greater than 90 degrees) to the fibers in the ply above or below. Non-limiting examples of cross-ply structures or arrangements are shown in FIGS. 7 and 8.

In a cross-ply structure, if the fiber radius is uniform (e.g., constant) and the distance between neighboring fiber segments across the free space, $\lambda$, is further constant (e.g., uniform or equidistant) or about constant, the free spaces form an interconnected, open pore network that is highly ordered and highly uniform across the drug-containing solid. It is expected, for example, that such highly uniform and ordered structures enable uniform wetting of the three dimensional structural framework eliminating constraints to expansion and ensuring repeatable, optimal properties.

Thus, the general advantage of ordered structures, and cross-ply structures in particular, over disordered or random structures is that relevant properties, such as the expansion rate of the dosage form, and/or the drug release rate, can be better controlled.

Further non-limiting embodiments of the dosage form structure are presented in U.S. application Ser. No. 15/482,776 titled "Fibrous dosage form", U.S. application Ser. No. 15/964,058 titled "Method and apparatus for the manufacture of fibrous dosage forms", and U.S. application Ser. No. 15/964,063 and titled "Dosage form comprising two-dimensional structural elements".

b) Thickness of Elements and Spacing Between Segments

For achieving a specific surface area (i.e., surface area-to-volume ratio) large enough to guarantee rapid expansion of dosage forms, in some embodiments the one or more elements (e.g., fibers, etc.) have an average thickness, $h_o$, no greater than 2.5 mm. This includes, but is not limited to $h_o$ no greater than 2 mm or no greater than 1.5 mm or no greater than 1.25 mm, or no greater than 1 mm or no greater than 750 om.

It may be noted, however, that if the elements are very thin and tightly packed, the spacing and free spacing between the elements can be so small that the rate at which dissolution fluid percolates or flows into the free space is limited. Furthermore, dosage forms with very thin elements may be difficult to manufacture by, for example, 3D-micropatterning. Thus, in some embodiments the one or more elements have an average thickness, $h_o$, in the ranges of 0.1 μm-2.5 mm 0.5 μm-2.5 mm 1 μm-2.5 mm 5 μm-2.5 mm 10 μm-2.5 mm 2.5 μm-2 mm 5 μm-2 mm 5 μm-1.5 mm 5 μm-1 mm 10 μm-1 mm 10 μm-750 μm, 20 μm-1.5 mm or 20 μm-1 mm.

The element thickness, h, may be considered the smallest dimension of an element (i.e., h≤w and h≤l, where h, w and l are the thickness, width and length of the element, respectively). The average element thickness, $h_o$, is the average of the element thickness along the length or width of the one or more elements. A non-limiting example for deriving the average element thickness is presented in U.S. application Ser. No. 15/482,776 titled "Fibrous dosage form".

Also, to ensure rapid percolation of dissolution fluid into the interior of the dosage form structure, the effective free spacing, $\lambda_{f,e}$, between adjoining segments should typically be on the micro- or meso-scale. Thus, in some embodiments, the effective free spacing, $\lambda_{f,e}$, on average is greater than 0.1 μm. This includes, but is not limited to an average $\lambda_{f,e}$ greater than 0.25 μm, or greater than 0.5 μm, or greater than 1 μm, or greater than 2 μm, or greater than 5 μm, or greater than 7 μm, or greater than 10 μm, or greater than 15 μm, or greater than 20 μm, or greater than 25 μm, or greater than 30 μm, or greater than 40 μm, or greater than 50 μm.

Because the dosage form volume is generally limited, however, the drug and excipient masses that can be loaded in the dosage form may be too small if the effective free spacing is too large. Thus, in some embodiments, the effective free spacing may be in the ranges 0.1 μm-5 mm 0.1 μm-3 mm 0.25 μm-5 mm 0.5 μm-5 mm 1 μm-3 mm 5 μm-2.5 mm, 10 μm-2 mm 10 μm-4 mm 5 μm-4 mm 10 μm-3 mm 15 μm-3 mm 20 μm-3 mm, 30 μm-4 mm 40 μm-4 mm or 50 μm-4 mm.

The effective free spacing between adjoining segments (referred to herein as "effective free spacing") is defined as the maximum diameter of a sphere that fits in the corresponding free space considering the elements or segments as rigid, fixed bodies. Non-limiting examples that illustrate how the effective free spacing may be derived or measured are presented in U.S. application Ser. No. 15/482,776 titled "Fibrous dosage form".

c) Surface Properties of Elements and Segments

Furthermore, for enabling percolation of dissolution fluid into the interior of the structure (e.g., into the free spaces), in some embodiments the surface composition of at least one element is hydrophilic. In this disclosure, a surface or surface composition is hydrophilic, also referred to as "wettable by a physiological fluid", if the contact angle of a droplet of physiological fluid on said surface in air is no more than 90 degrees. This includes, but is not limited to a contact angle of a droplet of said fluid on said solid surface in air no more than 80 degrees, or no more than 70 degrees, or no more than 60 degrees, or no more than 50 degrees, or no more than 40 degrees, or no more than 30 degrees. It may be noted that in some embodiments the contact angle may not be stationary. In this case, a solid surface may be understood "hydrophilic" if the contact angle of a droplet of physiological fluid on said solid surface in air is no more than 90 degrees at least 20-360 seconds after the droplet has been deposited on said surface. A non-limiting illustration of a droplet on a surface is presented in U.S. application Ser. No. 15/482,776 titled "Fibrous dosage form".

Generally, the percolation rate of physiological fluid into the interconnected free spaces is increased if the contact angle between said fluid and the surface of the three dimensional structural framework of one or more elements is decreased. Thus, in some embodiments, at least one element or at least one segment of an element comprises a hydrophilic or highly hydrophilic coating for enhancing the rate of fluid percolation into the dosage form structure. In the context herein, a solid surface (e.g., a solid material or a solid compound or a surface or a coating) is understood "highly hydrophilic" if the contact angle of a droplet of physiological fluid on the surface of said solid in air is no more is no more than 45 degrees. This includes, but is not limited to a contact angle of a droplet of said fluid on said solid surface in air no more than 35 degrees, or no more than 30 degrees, or no more than 25 degrees, or no more than 20 degrees, or no more than 15 degrees.

Non-limiting examples of hydrophilic (or highly hydrophilic) compounds that may serve as coating of elements (or segments of elements) include polyethylene glycol, polyvinyl alcohol, polyvinyl alcohol-polyethylene glycol copolymer, polyvinyl pyrrolidone, silicon dioxide, talc, magnesium stearate, polyols (e.g., mannitol, maltitol, xylitol, maltitol, isomalt, lactitol, sucrose, glucose, erythritol, etc.), and so on.

After all it may be noted that in some embodiments the free spacing between segments and the composition of the surface of the one or more elements are so that the percolation time of physiological/body fluid into one or more interconnected free spaces of the drug-containing solid is no greater than 200 seconds under physiological conditions. This includes, but is not limited to a percolation time of physiological/body fluid into one or more interconnected free spaces of the drug-containing solid no greater than 100, or no greater than 50 seconds, or no greater than 25 seconds, or no greater than 10 seconds under physiological conditions.

d) Composition of Elements and Properties of Excipient

In some embodiments, the weight fraction of drug in at least one element (e.g., a fiber, sheet, bead, etc.) with respect to the total weight of said element (e.g., the total weight of said fiber, sheet, etc.) is no greater than 0.9. This includes, but is not limited to a drug weight fraction in an element with respect to the total weight of said element no greater than 0.85, or no greater than 0.8, or no greater than 0.75, or no greater than 0.7, or no greater than 0.65.

Similarly, in some embodiments the weight fraction of drug in the three dimensional structural framework of one or more elements with respect to the total weight of said frameworkd is no greater than 0.9. This includes, but is not limited to a drug weight fraction in the structural framework with respect to the total weight of said framework no greater than 0.85, or no greater than 0.8, or no greater than 0.75, or no greater than 0.7, or no greater than 0.65.

Furthermore, in some embodiments the weight fraction of absorptive polymeric excipient in at least one element with respect to the total weight of said element is greater than 0.1. This includes, but is not limited to a weight fraction of absorptive polymeric excipient in an element with respect to the total weight of said element greater than 0.15, or greater than 0.2, or greater than 0.25, or greater than 0.3, or greater than 0.35, or greater than 0.4.

Similarly, in some embodiments the weight fraction of absorptive polymeric excipient in the three dimensional structural framework of one or more elements with respect to the total weight of said framework is greater than 0.1. This includes, but is not limited to a weight fraction of absorptive, polymeric excipient in the structural framework with respect to the total weight of said framework greater than 0.15, or greater than 0.2, or greater than 0.25, or greater than 0.3, or greater than 0.35, or greater than 0.4.

In some embodiments, the effective diffusivity of physiological/body fluid in an absorptive excipient (and/or an element or a segment) is greater than $0.1 \times 10^{-11}$ m$^2$/s under physiological conditions. This includes, but is not limited to an effective diffusivity of physiological/body fluid in an absorptive excipient (and/or an element or a segment) greater than $0.2 \times 10^{-11}$ m$^2$/s, or greater than $0.5 \times 10^{-11}$ m$^2$/s, or greater than $0.75 \times 10^{-11}$ m$^2$/s, or greater than $1 \times 10^{-11}$ m$^2$/s, or greater than $2 \times 10^{-11}$ m$^2$/s, or greater than $3 \times 10^{-11}$ m$^2$/s, or greater than $4 \times 10^{-11}$ m$^2$/s under physiological conditions.

Alternatively, for absorptive excipients where diffusion of physiological/body fluid to the interior is not Fickian, a rate of penetration may be specified. In some embodiments, the rate of penetration of a physiological/body fluid into a solid, absorptive excipient (and/or an element or a segment) is greater than an average thickness of the one or more drug-containing elements divided by 3600 seconds (i.e., $h_0/3600$ µm/s). In other examples without limitation, rate of penetration may be greater than $h_0/1800$ µm/s, greater than $h_0/1200$ µm/s, greater than $h_0/800$ µm/s, greater than $h_0/600$ µm/s, or greater than $h_0/500$ µm/s.

For determining the effective diffusivity (and/or the rate of penetration) of dissolution medium in a solid, absorptive excipient (and/or an element or a segment) the following procedure may be applied. An element (e.g an element or segment of the dosage form structure or an element or segment that just consists of the absorptive excipient) may be fixed at both ends and placed in a still dissolution medium at 37° C. The time $t_1$ for the element to break apart or deform substantially may be recorded. (By way of example but not by way of limitation, a deformation of an element may generally be considered substantial if either the length, width, or thickness of the element differs by more than 10 to 20 percent from its initial value. In elements with weight fraction, $w_e$, or volume fraction, $\varphi_e$, of absorptive/swellable excipient smaller than 0.4, a deformation of an element or segment may be considered substantial if either the length, width, or thickness of the element or segment differs by more than $25 \times \varphi_e$ percent or $25 \times w_e$ percent from its initial value.) The effective diffusivity, $D_{eff}$, may then be determined according to $D_{eff} = h_{init}^2/4t_1$ where $h_{init}$ is the initial element or segment thickness (e.g., the thickness of the dry element or segment). Similarly, the rate of penetration of a physiological/body fluid into the element or segment is equal to $h_{init}/2t_1$. Further non-limiting examples for deriving the effective diffusivity or rate of penetration are presented in U.S. application Ser. No. 15/482,776 titled "Fibrous dosage form".

Moreover, in some embodiments the solubility of at least one absorptive, polymeric excipient is greater than about 0.1 g/l in physiological/body fluids under physiological conditions. This includes, but is not limited to a solubility greater than 0.5 g/l, or greater than 1 g/l, or greater than 5 g/l, or greater than 10 g/l, or greater than 20 g/l, or greater than 30 g/l, or greater than 50 g/l, or greater than 70 g/l, or greater than 100 g/l in a physiological/body fluid under physiological conditions.

The solubility of a material or compound in a fluid is generally referred to herein as ratio of the maximum mass of said material that can be dissolved in a given volume of said fluid at equilibrium divided by said fluid volume. The solubility may, for example, be determined by optical methods.

Furthermore, for polymers that form viscous solutions when combined with a dissolution medium, the 'solubility' in the context of this invention is the polymer concentration in physiological/body fluid at which the average shear viscosity of the polymer-physiological/body fluid solution is 5 Pa·s in the shear rate range 1-100 l/s under physiological conditions. The pH value of the physiological/body fluid may thereby be adjusted to the specific physiological condition of interest.

In some embodiments, to ensure that the dosage form dissolves or disintegrates eventually in a physiological fluid (e.g., to avoid that the expanded dosage form or viscous medium clogs the gastrointestinal system, etc.), at least one absorptive polymeric excipient comprises a plurality of individual chains or molecules that dissolve or disentangle upon immersion in a physiological fluid.

Moreover, in some embodiments the molecular weight of at least one absorptive polymeric excipient is greater than 2 kg/mol (e.g., greater than 5 kg/mol, or greater than 10 kg/mol, or greater than 20 kg/mol, or greater than 50 kg/mol). Furthermore, in some embodiments the molecular weight of at least one absorptive polymeric excipient is between 2 kg/mol and 1000 kg/mol (e.g., in the ranges 5-750 kg/mol, 5-500 kg/mol, 10-500 kg/mol, 2-200 kg/mol, 5-200 kg/mol, 2-50 kg/mol, or 2-100 kg/mol).

Non-limiting examples of excipients that satisfy some or all the requirements of the polymeric excipient include but are not limited to hydroxypropyl methylcellulose, hydroxyethyl cellulose, polyvinyl alcohol, polyvinylpyrrolidone, hydroxypropyl methylcellulose acetate succinate, sodium alginate, hydroxypropyl cellulose, hydroxyethyl cellulose, methyl cellulose, hydroxypropyl methyl ether cellulose, starch, chitosan, pectin, polymethacrylates (e.g., poly(methacrylic acid, ethyl acrylate) 1:1, or butylmethacrylat-(2-dimethylaminoethyl)methacrylat-methylmathacrylat-copolymer), vinylpyrrolidone-vinyl acetate copolymer, among others.

e) Microstructure of Elements and Three Dimensional Structural Framework

Non-limiting examples of the microstructure of elements and the three dimensional structural framework of one or more elements are presented in U.S. application Ser. No. 15/482,776 titled "Fibrous dosage form", U.S. application Ser. No. 15/964,058 titled "Method and apparatus for the manufacture of fibrous dosage forms", and U.S. application Ser. No. 15/964,063 and titled "Dosage form comprising two-dimensional structural elements".

In some preferred embodiments, however, drug is embedded in an element as either particles or molecules in a matrix of absorptive, polymeric excipient.

Similarly, in some preferred embodiments drug is embedded in the three dimensional structural framework of one or more elements as either particles or molecules in a matrix of absorptive, polymeric excipient.

In some embodiments, an element expands by dilution of polymeric excipient with physiological or body fluid.

Similarly, in some embodiments, the three dimensional structural framework of one or more elements expands by dilution of polymeric excipient with physiological or body fluid.

f) Properties of Drug-Containing Solid and Dosage Form

Figure 13:
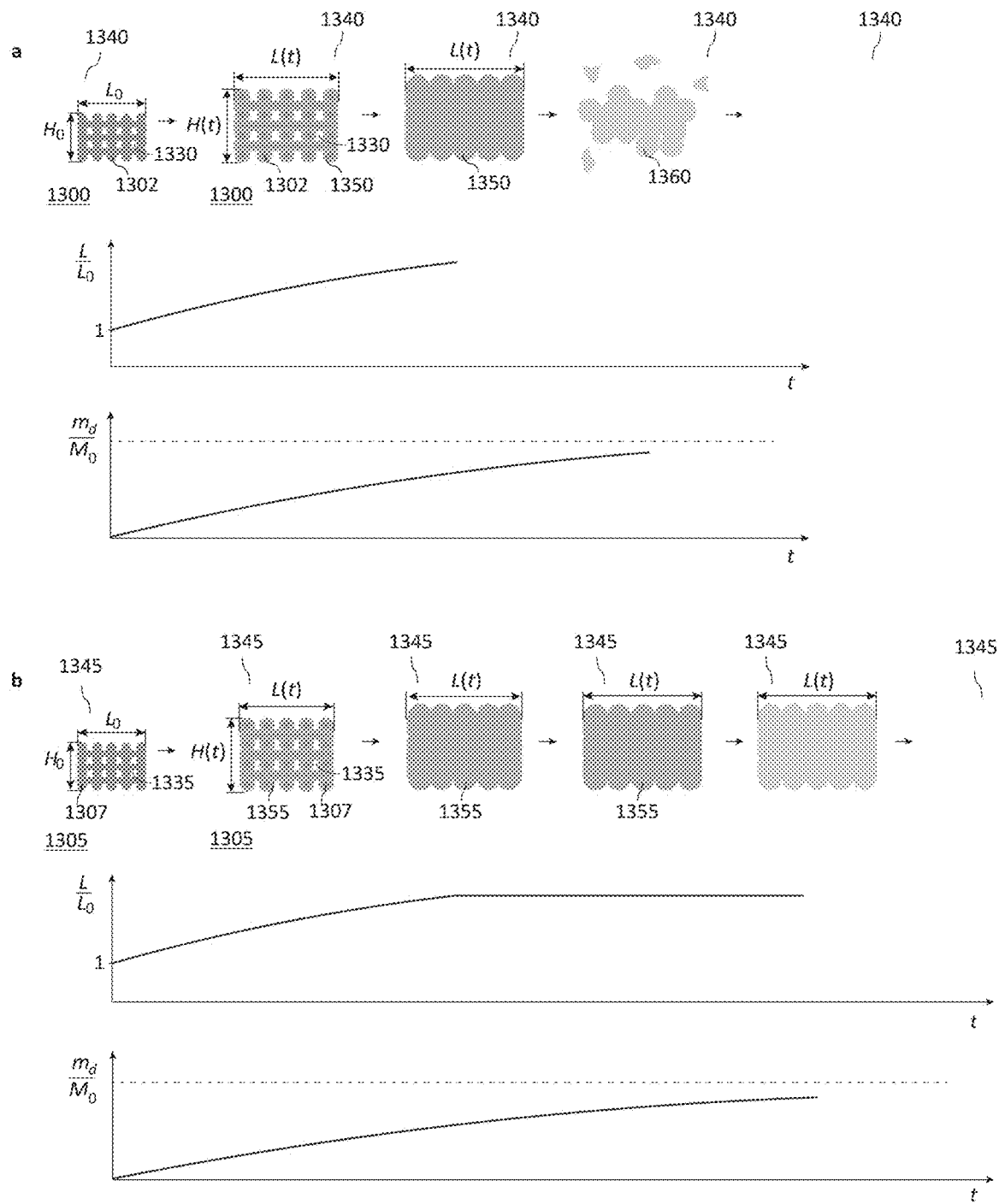
FIG. 13 presents non-limiting examples of the deformation process of viscous media: (a) uniform medium with uniform shear stress and strain, and (b) non-uniform medium with non-uniform stresses and strains.

In some embodiments, the drug-containing solid (or the three dimensional structural framework) expands isotropically (e.g., uniformly in all directions) while transitioning to a fluidic or viscous medium. In the invention herein, a solid or viscous mass or viscous medium is understood to expand isotropically if the normalized expansion (e.g., the ratio of a length difference and the initial length, such as $(L(t)-L_0)/L_0$, $(H(t)-H_0)/H_0$, etc.) deviates by less than 50 percent of its maximum value by changing direction or orientation. Thus, in an isotropically expanding solid, viscous mass, viscous medium, or framework the normalized expansion is roughly the same in all directions. FIG. 13a is a non-limiting schematic illustration of a drug-containing solid that expands isotropically.

Furthermore, in some embodiments geometric similarity of the three dimensional structural framework is preserved while transitioning to a fluidic or viscous medium. In the invention herein, a microstructure or three dimensional structural framework is geometrically similar to the initial structure or framework if the expanded microstructure or expanded framework can be obtained roughly by scaling or enlarging the initial structure or framework (e.g., by scaling or enlarging the initial structure or framework uniformly in all directions). Thus, in an expanding framework where geometric similarity is preserved, interconnected free spaces remain open and interconnected as the structure expands. This allows the framework to absorb more water (e.g., physiological fluid) while expanding, and hence to expand by a greater extent.

Geometric similarity of an expanding framework may be preserved if the elements (or segments) are wetted uniformly by the dissolution fluid and/or the individual elements (or individual segments) expand substantially isotropically upon contact with said dissolution fluid. It is understood that expanding frameworks exist where geometric similarity may be "preserved" or "almost preserved" only initially. All such frameworks where geometric similarity is partially or somewhat or initially preserved are referred to herein as "frameworks where geometric similarity is preserved during expansion". FIGS. 6b and 6c present a non-limiting example of two three dimensional structural frameworks that are geometrically similar.

FIG. 13a presents a non-limiting example of a drug-containing solid comprising a geometrically similar expanding three dimensional structural framework 1302 and interconnected free spaces 1330 forming an open pore network. Upon immersion in a dissolution fluid 1340, the framework 1302 is wetted uniformly by the said fluid 1340. Consequently, the framework 1302 absorbs water 1340, transitions to viscous, and expands. Moreover, because geometric similarity is preserved during expansion, the free spaces 1330 remain open and dissolution fluid 1340 continues to flow into the structure as the framework 1302 expands. As a result, as the framework (or the drug-containing solid) transitions to a viscous medium 1350 the viscosity ever decreases (e.g., the viscosity or "average viscosity" of the drug-containing solid ever decreases while transitioning to a viscous medium; it may be repeated that the drug-containing solid can be a "solid", a combination of a "solid" and a "viscous medium", a "viscous medium", a combination of a "solid" and a dilute solution or dispersion, or a combination of a "viscous medium" and a dilute solution or dispersion while transitioning to a viscous medium). Eventually, therefore, the viscosity of the viscous medium 1350 may be so low that it 1350 deforms and thins down due to the forces applied by the dissolution fluid (e.g., shear traction, pressure imbalances, buoyancy, gravity, etc.). This increases the specific surface area of the viscous medium 1350 and hence the erosion rate into the dissolution fluid 1340. It should be noted again that in some cases the drug-containing solid or viscous medium 1350 may expand and be diluted to such extent that a "dilute solution" or a "dilute dispersion" is formed. Moreover, it should be repeated that "deforming due to external forces" and "thinning down" is not considered "expanding" herein.

Thus, for immediate release and delivery of drug by the dosage form, the viscosity of the expanded, dilute solution 1360 may be so small that it deforms and erodes rapidly into the dissolution fluid 1340. Expansion of the drug-containing solid 1300 lowers the viscosity of the viscous medium 1350 or dilute solution 1360 formed and accelerates the erosion and drug release rates.

Thus, in some embodiments eighty percent of the drug content in the drug-containing solid is released in less than 45 minutes after immersion in a physiological or body fluid under physiological conditions. This includes, but is not limited to a drug-containing solid that releases eighty percent of the drug content in less than 40 minutes, or in less than 35 minutes, or in less than 30 minutes, or in less than 25 minutes, or in less than 20 minutes, or in less than 15 minutes, or in less than 10 minutes, or in 1-45 minutes, 1-30 minutes, 2-45 minutes, or 2-30 minutes after immersion in a physiological fluid under physiological conditions.

In some embodiments, however, geometric similarity of an expanding framework may not or not quite or almost not be preserved if the individual elements 230, 240 (or individual segments) expand substantially anisotropically upon contact with a dissolution fluid 220.

FIG. 13*b* is a non-limiting example of a drug-containing solid 1305 comprising a three dimensional structural framework 1307 of elements that expand faster along their thickness than along their length, and interconnected free spaces 1335 defining an open pore network. Upon immersion in a dissolution fluid 1345, the framework 1307 is wetted uniformly by the said fluid 1345. Consequently, the framework 1307 absorbs water 1345, transitions to viscous, and expands. Because the elements expand anisotropically, they coalesce as the framework 1307 expands and the free spaces 1335 and open pores close out. The flow of dissolution fluid 1345 into the interior may then be stopped or greatly reduced. As a result, an expanded, viscous mass 1355 of polymeric excipient concentration far greater than the disentanglement concentration and viscosity far greater than the viscosity of the dissolution fluid 1345 may be formed. The viscous mass 1355 may not or very slowly deform or dissolve in the dissolution fluid 1345. Drug may be released by the slow diffusion of drug molecules through the thick viscous mass 1355.

Thus, in some embodiments eighty percent of the drug content in the drug-containing solid is released in more than 30 minutes after immersion in a physiological or body fluid under physiological conditions. This includes, but is not limited to a drug-containing solid that releases eighty percent of the drug content in more than 40 minutes, or in more than 50 minutes, or in more than 60 minutes, or in more than 100 minutes, or in 30 minutes-48 hours, 30 minutes-36 hours, 30 minutes-24 hours, or 45 minutes-24 hours after immersion in a physiological fluid under physiological conditions.

Finally, in some embodiments the tensile strength of a drug-containing solid or a three dimensional structural framework of one or more elements is between 0.01 MPa and 100 MPa (this includes, but is not limited to tensile strength of at least one element is greater than 0.02 MPa, or greater than 0.05 MPa, or greater than 0.1 MPa, or greater than 0.2 MPa, or greater than 0.5 MPa, or greater than 1 MPa, or greater than 1.5 MPa, or greater than 2 MPa, or greater than 3 MPa, or greater than 5 MPa).

Method and Apparatus to Manufacture the Dosage Form (a) Method

Figure 14:
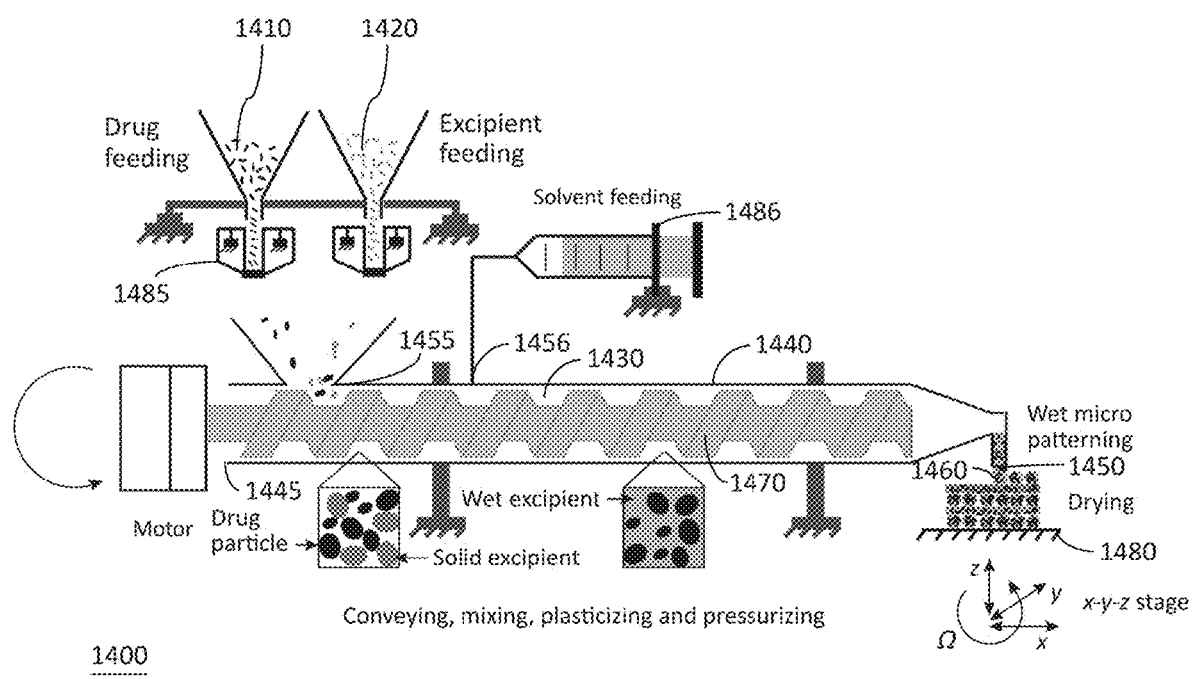
FIG. 14 is a schematic of a method and an apparatus to manufacture the dosage forms according to this invention.

FIG. 14 presents a non-limiting example of a method of manufacturing pharmaceutical solid dosage forms according to this invention. One or more drugs 1410 and/or one or more absorptive polymeric excipients 1420 (the one or more drugs 1410 and/or one or more excipients 1420 combined are also referred to herein as "one or more solid constituents") are injected into an extrusion channel 1430 having a cross section extending along its length inside a housing 1440. Also, at least one solvent that solvates at least one injected solid constituent is injected into the extrusion channel 1430. The rate at which solvent is injected and the volume fraction of the at least one solvated solid constituent with respect to the total volume of the one or more injected solid constituents are so that the one or more injected solid constituents form a plasticized matrix upon contact and mixing with the solvent. The plasticized matrix is (subsequently or concurrently as it is formed) conveyed towards an exit port 1450 of the extrusion channel 1430 by applying mechanical work on the plasticized matrix (e.g., by applying a shear force on the plasticized matrix along a fraction of the extrusion channel 1430, or by applying a pressure gradient in the direction of the extrusion channel 1430, etc.). The plasticized matrix is then extruded through an exit port 1450 to form at least one plasticized fiber 1460. Subsequently, said at least one plasticized fiber 1460 (e.g., one or more plasticized fibers) is/are structured to a three dimensional structural network of one or more fibers. In some embodiments, the three dimensional structural network of one or more fibers is then solidified by evaporating the solvent to form a fibrous dosage form with sufficient rigidity. Furthermore, upon immersion in a physiological fluid the three dimensional structural framework is uniformly wetted and transitions to a viscous medium, thereby expanding in all dimensions.

Figure 15:
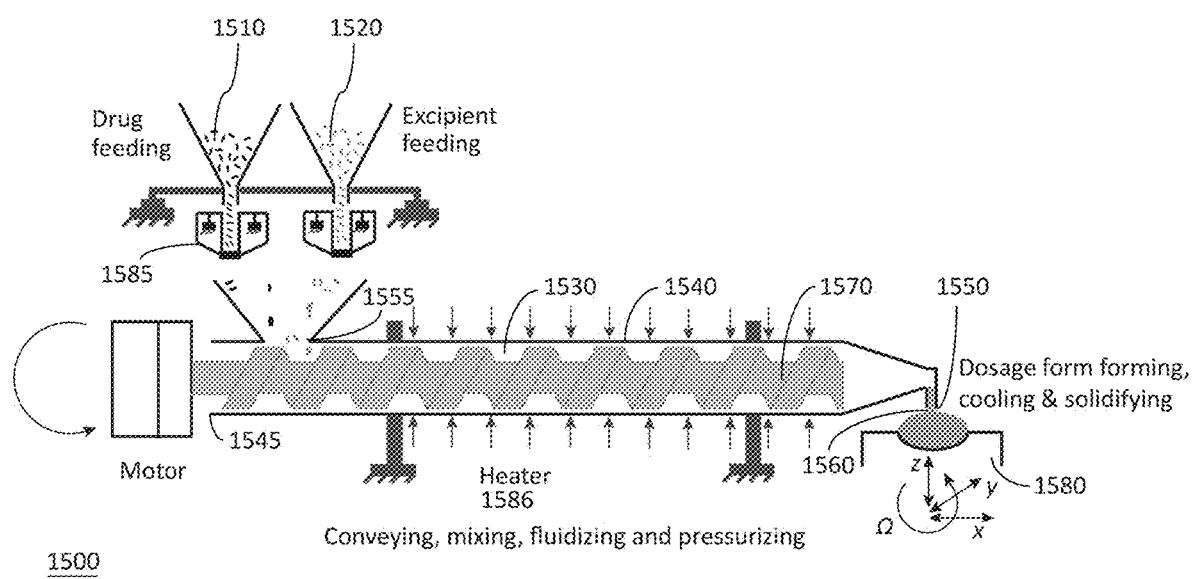
FIG. 15 is another schematic of a method and an apparatus to manufacture the dosage forms according to this invention.

Another non-limiting example of a method of manufacturing pharmaceutical solid dosage forms according to this invention is shown in FIG. 15. One or more drugs 1510 and/or one or more solid excipients 1520 (e.g., one or more solid constituents) are fed or injected into an extrusion channel 1530 having a cross section extending along its length inside a housing 1540. The injected one or more solid constituents are then heated to a temperature greater than the melting temperature of at least one injected solid constituent. Thus at least one injected solid constituent is fluidized (e.g., it transitions from solid or solid-like to fluidic or fluid-like) upon heating. The volume fraction of the fluidized solid constituent (or the fluidized solid constituents) with respect to the volume of the one or more injected solid constituents is so that the one or more injected solid constituents form a plasticized matrix upon heating (and mixing). The plasticized matrix is (subsequently or concurrently as it is formed) conveyed towards an exit port 1550 of the extrusion channel 1530 by applying mechanical work on the plasticized matrix (e.g., by applying a shear force on the plasticized matrix along a fraction of the extrusion channel 1530, or by applying a pressure gradient in the direction of the extrusion channel 430, etc.). The plasticized matrix is then extruded through an exit port 1550 to form at least one plasticized fiber 1560. Subsequently, said at least one plasticized fiber 1560 (e.g., one or more plasticized fibers) is/are structured to a three dimensional structural network of one or more fibers. In some embodiments, the three dimensional structural network of one or more fibers is then solidified by cooling it to a temperature below the solidification temperature. Furthermore, upon immersion in a physiological fluid the three dimensional structural framework is uniformly wetted and transitions to a viscous medium, thereby expanding in all dimensions.

In some embodiments, the structuring of at least one plasticized fiber to a three dimensional structural network of one or more drug-containing fibers is performed by 3D-patterning said at least one plasticized fiber on a substrate.

In some embodiments, the three dimensional structural framework of one or more drug-containing fibers comprises a plurality of criss-crossed stacked layers of fibrous structural elements.

It may be noted that in any example presented herein, the extrusion channel 1430, 1530 may comprise one or multiple exit ports through which plasticized material can be extruded. Also, a three dimensional network of one or more fibers may be combined with other elements of a dosage form, such as one or more drug-containing solids, one or more solids that do not contain a drug, one or more coating shells, liquids, gases, etc. Furthermore, in the invention herein, the terms "plasticized fiber" and "fibrous extrudate" are used interchangeably. Moreover, any sequence of steps described in the invention herein may be performed concurrently (e.g., at least one step is performed at the same time as another step) or in sequence (e.g., one step is performed at a time and a subsequent step starts after completion of a previous step). In addition, any process step described with respect to one aspect of the invention can be applied with respect to another aspect. By way of example but not by way of limitation, a solid constituent may be plasticized by a combination of solvation and melting.

Further non-limiting examples of methods to manufacture the dosage forms disclosed herein are presented in the co-pending U.S. application Ser. No. 15/482,776 titled "Fibrous dosage form", U.S. application Ser. No. 15/964,058 titled "Method and apparatus for the manufacture of fibrous dosage forms", and U.S. application Ser. No. 15/964,063 titled "Dosage form comprising two-dimensional structural elements". Any more examples of the process steps to manufacture the dosage forms disclosed would be obvious to a person of ordinary skill in the art. All of them are within the scope of this invention.

(b) Apparatus

FIG. 14 also presents a non-limiting example of an apparatus 1400 for the manufacture of pharmaceutical solid dosage forms according to this invention. The apparatus 1400 comprises an internally hollow housing 1440 having an internal surface encapsulating and defining an extrusion channel 1430 having a first end 1445 and a second end 1450 and a cross section extending axially along its length from said first end 1445 to said second end 1450 and terminating into an exit port 1450 at the second end 1450. The housing 1440 further has at least a first feeding port 1455 between the first end 1445 and second end 1450 for feeding or injecting at least one solid constituent into the extrusion channel 1430. Moreover, the housing 1440 has at least a second feeding port 1456 between the first feeding port 1455 and the exit port 1450 for injecting at least one liquid into the extrusion channel 1430 to form a plasticized matrix by solvating at least one injected solid constituent. The apparatus 1400 further comprises at least one conveying element 1470 for extruding the plasticized matrix in the extrusion channel through an exit port 1450 to form at least one plasticized fiber 1460. The apparatus 1400 further comprises a fiber structuring unit 1480 to structure said at least one plasticized fiber 1460 (e.g., one or more plasticized fibers) to a three dimensional structural network of one or more fibers. In some embodiments, the apparatus 1400 further comprises a solid constituent feeding unit 1485 for injecting at least one solid constituent through the first feeding port 1455 into the extrusion channel 1430. Furthermore, in some embodiments the apparatus further comprises a solvent feeding unit 1486 attached to the second feeding port 1456 for injecting at least one solvent into the extrusion channel 1430. Furthermore, upon immersion in a physiological fluid the three dimensional structural framework is uniformly wetted and transitions to a viscous medium, thereby expanding in all dimensions.

Another non-limiting schematic of an apparatus 1500 for the manufacture of pharmaceutical solid dosage forms according to this invention is shown in FIG. 15. The apparatus 1500 comprises an internally hollow housing 1540 having an internal surface encapsulating and defining an extrusion channel 1530 having a first end 1545 and a second end 1550 and a cross section extending axially along its length from said first end 1545 to said second end 1550 and terminating into an exit port 1550 at the second end 1550. The housing 1540 further has at least a first feeding port 1555 between the first end 1545 and second end 1550 for feeding or injecting at least one solid constituent into the extrusion channel 1530. The apparatus 1500 further comprises at least one heating element 1586 for fluidizing at least one injected solid constituent so that the injected one or more solid constituents form a plasticized matrix in the extrusion channel 1530. The apparatus 1500 further has at least one conveying element 1570 for extruding the plasticized matrix in the extrusion channel 1530 through an exit port 1550 to form at least one plasticized fiber 1560. The apparatus 1500 further has a fiber structuring unit 1580 to structure said at least one plasticized fiber 1560 (e.g., one or more plasticized fibers) to a three dimensional structural network of one or more fibers. In some embodiments, the apparatus 1500 further comprises a solid constituent feeding unit 1585 for injecting at least one solid constituent through the first feeding port 1555 into the extrusion channel 1530. Furthermore, upon immersion in a physiological fluid the three dimensional structural framework is uniformly wetted and transitions to a viscous medium, thereby expanding in all dimensions.

In some embodiments, the fiber structuring unit comprises a translating or rotating stage.

In some embodiments, the one or more plasticized fibers are structured to a three dimensional structural network of one or more drug-containing fibers by 3D-patterning said one or more plasticized fibers on a substrate defined by or attached to a translating or rotating stage.

In some embodiments, the three dimensional structural framework of one or more drug-containing fibers comprises a plurarity of criss-crossed stacked layers of fibrous structural elements.

In any example presented herein, the extrusion channel 1430, 1530 may comprise one or multiple exit ports through which a plasticized fiber may be extruded. Moreover, any feature described with respect to one aspect of the invention can be applied with respect to another aspect. By way of example but not by way of limitation, an apparatus may comprise at least a feeding port for injecting solvent into the extrusion channel to form a plasticized matrix and at least a heating element for fluidizing at least one injected solid constituent to form a plasticized matrix.

Further non-limiting examples of apparatuses to manufacture the dosage forms disclosed herein are presented in the co-pending U.S. application Ser. No. 15/482,776 titled "Fibrous dosage form", U.S. Application Ser. No. 15/964,058 titled "Method and apparatus for the manufacture of fibrous dosage forms", and U.S. application Ser. No. 15/964,063 titled "Dosage form comprising two-dimensional structural elements". Any more examples of apparatuses to manufacture fibrous dosage forms would be obvious to a person of ordinary skill in the art. All of them are within the scope of this invention.

EXPERIMENTAL EXAMPLES

The following examples present ways by which the fibrous dosage forms may be prepared and analyzed, and will enable one of skill in the art to more readily understand the principle thereof. The following examples are presented by way of illustration and are not meant to be limiting in any way.

Example 1: Preparation of Dosage Form and Fiber A

The drug used in dosage form and fiber A was ibuprofen, which was received as solid particles (particle size about 20

µm) from BASF, Ludwigshafen, Germany. The excipient was a mixture of 67 wt % hydroxypropyl methyl cellulose (HPMC) with a molecular weight of 10 kg/mol, and 33 wt % polyoxyl stearate (Tradename: Gelucire 48/16, Gattefosse). The common solvent used was dimethylsulfoxide (DMSO).

Dosage form A was prepared as follows. The as-received ibuprofen drug particles were first dissolved in DMSO at a concentration of 123 mg drug/ml DMSO. The solution was then combined with the excipient at a concentration of 1.11 g excipient/ml DMSO. Subsequently, the mixture was extruded through a desktop extruder to form a uniform, viscous paste.

Figure 16:
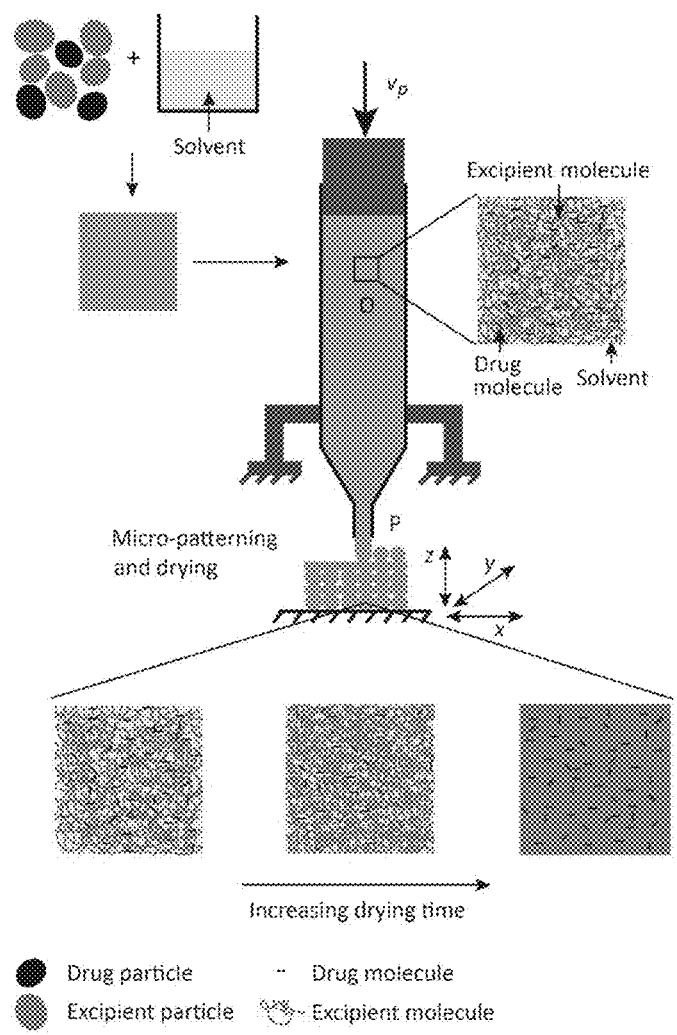
FIG. 16 schematically shows the apparatus and method applied for producing experimental dosage forms according to the invention herein.

As shown schematically in FIG. 16, the paste was then filled in a syringe at point O, and was extruded through a hypodermic needle to form and pattern a wet fibrous dosage form at P. The dosage form comprised a cross-ply arrangement of fibers with uniform inter-fiber distance in a ply (or layer). The nominal radius of the wet fiber (the inner radius of the hypodermic needle), $R_n$, was 130 µm; the nominal inter-fiber distance, $\lambda_n$, was 500 µm, as listed in Table 1. After patterning, warm air at a temperature of about 50° C. and a velocity of 2.3 m/s was blown on the dosage form to evaporate the solvent and solidify the structure. The drying time, $t_{dry}$, was about 35 minutes, after which the fibers were a homogeneous, solid-solution of drug and excipient molecules.

After drying, the structure was trimmed to a square disk shaped dosage form of nominal volume 8 mm×8 mm×3.6 mm. The weight fraction of drug in the dosage form was 0.1, the weight fraction of HPMC was 0.6, and the weight fraction of polyoxyl stearate was 0.3.

Single fiber A was prepared as described above (e.g., as dosage form A), but without structuring the fibrous extrudate to a dosage form.

Example 2: Preparation of Dosage Forms and Fibers B and C

Dosage forms B and C were prepared as follows. 20 wt % acetaminophen drug particles were first mixed with the excipient, 80 wt % HPMC of molecular weight 120 kg/mol. The mixture was then combined with a solvent, either DMSO (for preparing dosage form B) or water (for dosage form C). The volume of solvent per mass of excipient was 5.5 ml/g and 3.33 ml/g, respectively, for preparing dosage forms B and C. The drug-excipient-solvent mixture was then extruded through a laboratory extruder to form a uniform viscous paste. The viscous paste was put in a syringe equipped with a hypodermic needle of inner radius, $R_n$=130 µm (for preparing dosage form B) or $R_n$ 500 µm (for preparing dosage form C). The paste was then extruded through the needle and patterned as a fibrous dosage form with cross-ply arrangement of fibers. The nominal inter-fiber distance in a ply was uniform and equal to 730 µm (for preparing dosage form B) or 2800 µm (for preparing dosage form C). During and after patterning, warm air at a temperature of 60° C. and a velocity of about 2.3 m/s was blown over the fibrous dosage forms for a time, $t_{dry}$~40 minutes, to evaporate the solvent and freeze the structure. The process parameters to prepare the dosage forms are summarized in Table 1. After drying, the structure was trimmed to a square disk shaped dosage form of side length, $L_0$~8 mm. The thickness, $H_0$, of the dosage forms B and C was about 3 mm.

Single fibers B and C were prepared as dosage forms B and C, but without structuring the fibrous extrudate to a dosage form.

TABLE 1

Process parameters to prepare the single fibers and fibrous dosage forms.

| solvent | $v'_s$ (ml/g) | $R_n$ (µm) | $\lambda_n$ (µm) | $R_n/\lambda_n$ | $t_{dry}$ (min) |
|---|---|---|---|---|---|
| A | DMSO | 0.90 | 130 | 730 | 0.18 | 35 |
| B | DMSO | 5.50 | 130 | 730 | 0.18 | 40 |
| C | water | 3.33 | 500 | 2800 | 0.18 | 40 |

$v'_s$: volume of solvent/ mass of excipient,
$R_n$: inner radius of needle,
$\lambda_n$: nominal inter-fiber spacing,
$t_d$: drying time.
The microstructural parameters of dry dosage forms differ from the nominal parameters because the dosage form shrinks during drying (Table 2, later). In all formulations the drug weight fraction in the drug-excipient mixture was 0.2.

Example 3: Coating the Fibers in the Dosage Form Structures

To ensure that dissolution fluid percolates uniformly and rapidly into the dosage form structure after immersion, the fibers of all dosage form structures were coated with a thin, hydrophilic coating. The coating was applied by dripping a few droplets of a hydrophilic coating solution on the dosage form structure and drying immediately after. Drying was performed by blowing warm air at a temperature of 50° C. and a velocity of 2.3 m/s on the dosage form structure.

For coating the fibers of dosage form A, the hydrophilic coating solution consisted of polyvinyl pyrrolidone (PVP) with a molecular weight of 10 kg/mol (received from BASF, Ludwigshafen, Germany), mannitol, and ethanol. The concentration of PVP was 10 mg and that of mannitol 20 mg per ml of ethanol.

For coating the fibers of dosage forms B and C, the hydrophilic coating solution consisted of polyvinyl pyrrolidone (PVP) with a molecular weight of 10 kg/mol (as received from BASF, Ludwigshafen, Germany), silicone dioxide (as received from Evonik, Essen, Germany), and acetone. The concentrations of both PVP and silicone dioxide were 10 mg per ml of acetone.

Example 4: Scanning Electron Micrographs of Dosage Form and Fiber A

Dosage form and single fiber A were imaged with a Zeiss Merlin High Resolution SEM with a GEMINI column. Top views were imaged without any preparation of the sample. For imaging cross-sections, however, the sample was cut with a thin blade (MX35 Ultra, Thermo Scientific, Waltham, MA) in the imaging plane. Imaging was done with an in-lens secondary electron detector. The accelerating voltage was 5 kV and the probe current was 95 pA.

Figure 17:
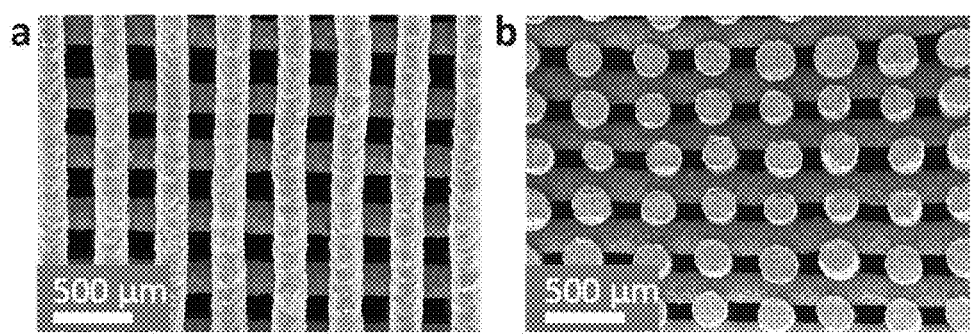
FIG. 17 shows scanning electron micrographs of the microstructure of the experimental dosage form A according to this invention: (a) top view and (b) side view.

Scanning electron micrographs of the microstructures of dosage form A are shown in FIG. 17. FIG. 17a is the top view and FIG. 17b the front view (e.g., the cross section). From FIGS. 17a and 17b, the fiber radius in the dosage form microstructure, $R_0$=104 µm, and the inter-fiber distance, $\lambda_0$=385 µm. The fiber radius is about 80 and the inter-fiber distance about 77 percent of the nominal value (Tables 1 and 2).

The microstructural parameters of the dry dosage form are smaller than the nominal values because the wet dosage form shrinks as solvent is removed during drying. For isotropic contraction, the ratios $$\frac{R_0}{R_n} = \frac{\lambda_0}{\lambda_n} = \left(1 - \frac{c_{solv}}{\rho_{solv}}\right)^{1/3} \quad (26)$$

where $c_{solv}$ is the concentration of solvent in the wet fiber and $\rho_{solv}$ the density of the solvent.

Dosage form A was prepared using a solvent concentration, $c_{solv}$=550 kg/m³, and the density of the solvent, $\rho_{solv}$=1100 kg/m³. Thus, the calculated $R/R_n = \lambda/\lambda_n = 0.79$, about the same as the measured values.

Moreover, because of gravity the wet fibers deform at the contact points, decreasing the distance between the fibers in the vertical direction. As a result, the solid volume fraction of the dried fibers with flattened contacts is greater than that of the nominal cross-ply structure with cylindrical fibers. Thus, for all dosage forms the volume fraction of the solid fibers may be expressed as:

$$\phi_s = \xi \frac{\pi R}{2\lambda} \quad (27)$$

where $\zeta$ is the ratio of the fiber diameter to the vertical distance between the fibers (i.e., the ratio of the fiber diameter to the average thickness of a micro-patterned layer or ply). From FIG. 17b $\zeta \approx 1.25$.

Figure 18:
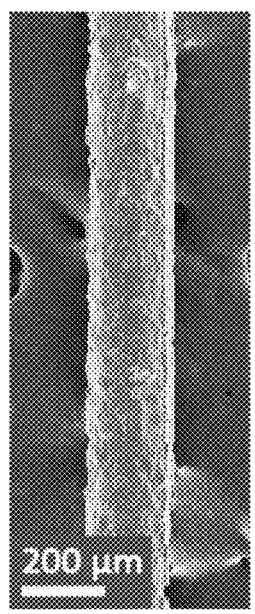
FIG. 18 is a scanning electron micrograph of the experimental single fiber A.

Finally, FIG. 18 is a scanning electron micrograph of a representative single fiber A. The fiber radius was 102 μm as listed in Table 2.

Example 5: Expansion and Disintegration of Dosage Form and Fiber A

For imaging the expansion and disintegration processes of dosage form and fiber A, the sample was first immersed in a beaker filled with 500 ml of dissolution fluid (0.1 M HCl in deionized water at 37° C.). The fluid was stirred with a paddle rotating at 50 rpm. The sample was then imaged continuously with a Nikon DX camera until it was dissolved.

Figure 19:
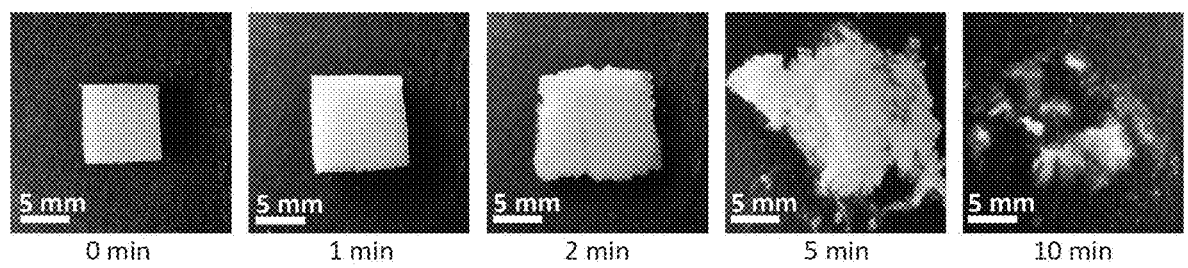
FIG. 19 presents a series of images to depict the expansion and disintegration processes of experimental dosage form A.
Figure 20:
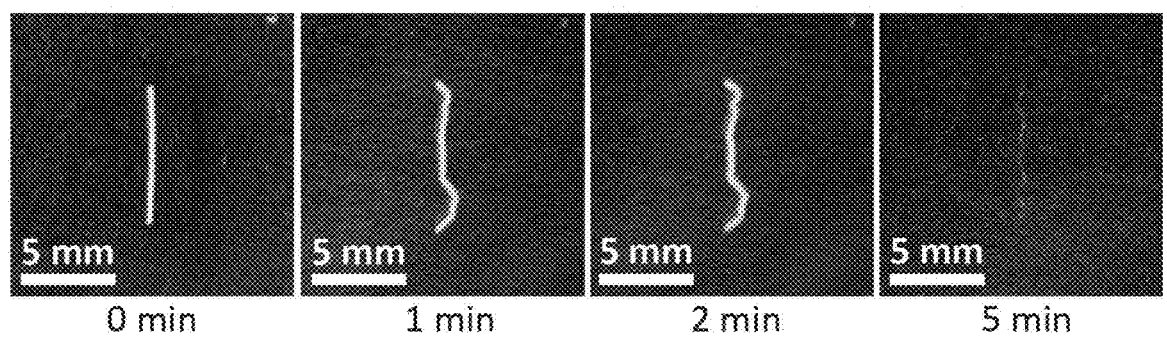
FIG. 20 is a series of images presenting the expansion and disintegration processes of single fiber A.

Images of the expanding and disintegrating dosage form A are shown in FIG. 19. Upon immersion of the dosage form, the dissolution fluid percolated into the void space almost immediately. The solid dosage form then transitioned to a viscous medium and expanded uniformly in all directions. The normalized expansion of the dosage form was 0.43 at two minutes of immersion, about the same as the radial and longitudinal expansion of the single fiber at that time (FIG. 20).

At about 2-3 minutes of immersion the dosage form started to deform viscously due to gravity and fluid shear. Material eroded from the surface, and the structure collapsed. A viscous drug-excipient-dissolution fluid solution was then formed along the flat surface. The viscous solution eroded continuously into the dissolution fluid; it was dissolved after about 10-15 minutes of immersion.

Example 6: Drug Release From Dosage Form and Fiber A

Drug release by dosage form and single fiber A was determined under the same conditions as the expansion and disintegration experiments (experimental example 5). The drug concentration in the dissolution fluid versus time was measured by UV absorption using a Perkin Elmer Lambda 1050 Spectrophotometer.

Figure 21:
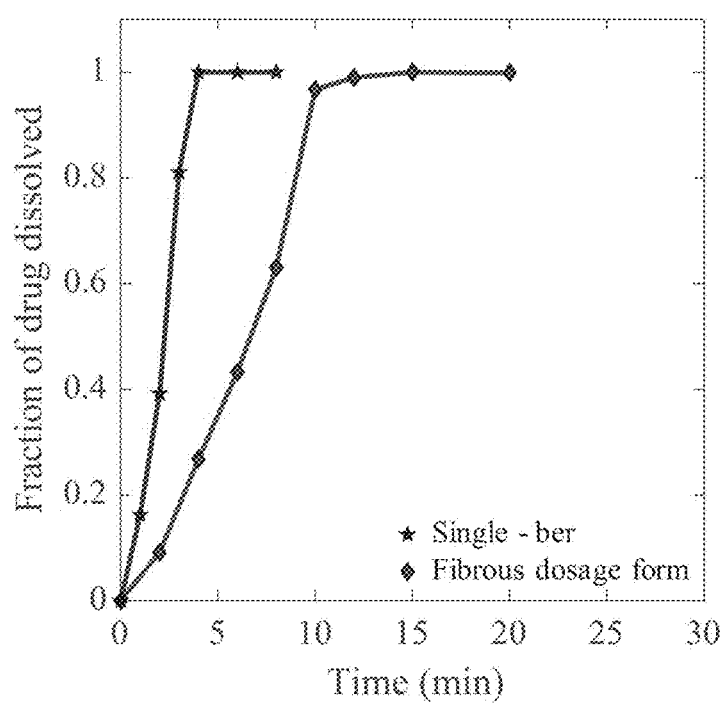
FIG. 21 shows the fraction of drug dissolved from the experimental dosage form and single fiber A versus time after immersion in a dissolution fluid.

The drug concentration in the medium versus time is shown in FIG. 21. As apparent, the fibrous dosage form and the single fiber released drug continuously until they were dissolved. The time to dissolve 80 percent of the drug content, $t_{0.8}$, was 3 minutes for the single fiber and 9 minutes for the dosage form, Table 2. Thus the drug release time by the dosage form was of the order of that of a single fiber.

Example 7: Scanning Electron Micrographs of Fibers B and C

Figure 22:
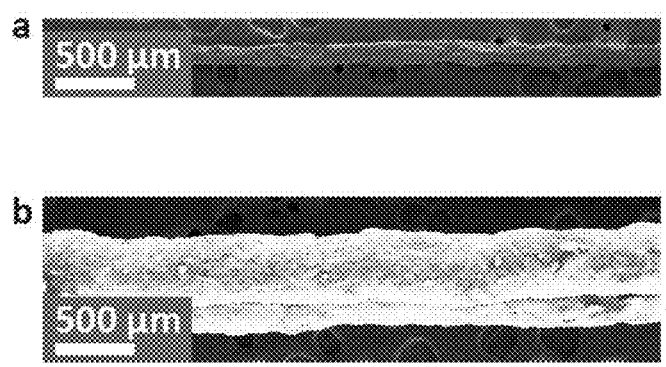
FIG. 22 presents scanning electron micrographs of the experimental single fibers B and C.

Scanning electron micrographs of single fibers B and C were taken under the conditions described above in the experimental example 4. From FIGS. 22a and 22b the fiber radii were 73 μm (fiber B) and 309 μm (fiber B), as listed in Table 2. It may be noted that the inner needle radii for preparing fibers B and C were 130 μm and 500 μm, respectively (Table 1).

Example 8: Expansion and Dintegration of Fibers B and C

Figure 23:
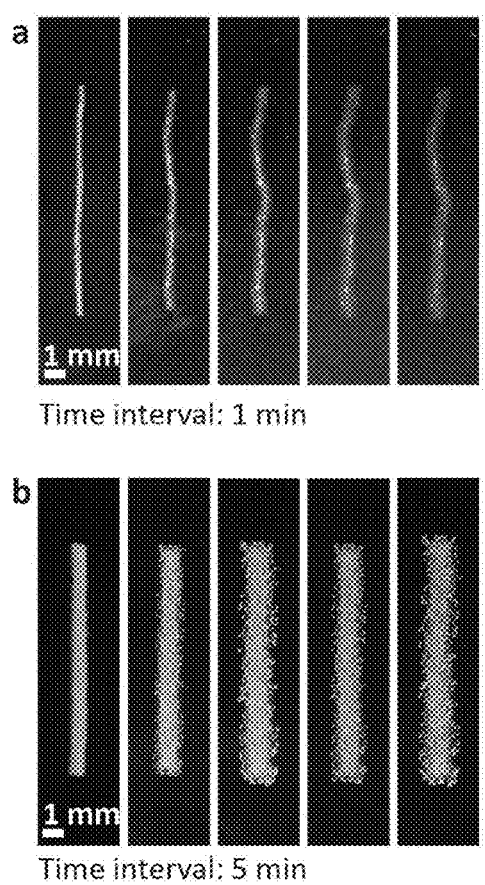
FIG. 23 presents series of images to depict the expansion and disintegration processes of (a) experimental fiber B and (b) experimental fiber C.

Images of the disintegrating single fibers B and C were taken under the conditions described in experimental example 4. From FIG. 23, upon immersion of the fibers in the dissolution fluid a viscous layer developed at the fiber-fluid interface. The layer grew inwards and outwards with time, and made the fibers expand. Fiber expansion was anisotropic; the fibers expanded radially, but the axial expansion was essentially negligible.

Figure 24:
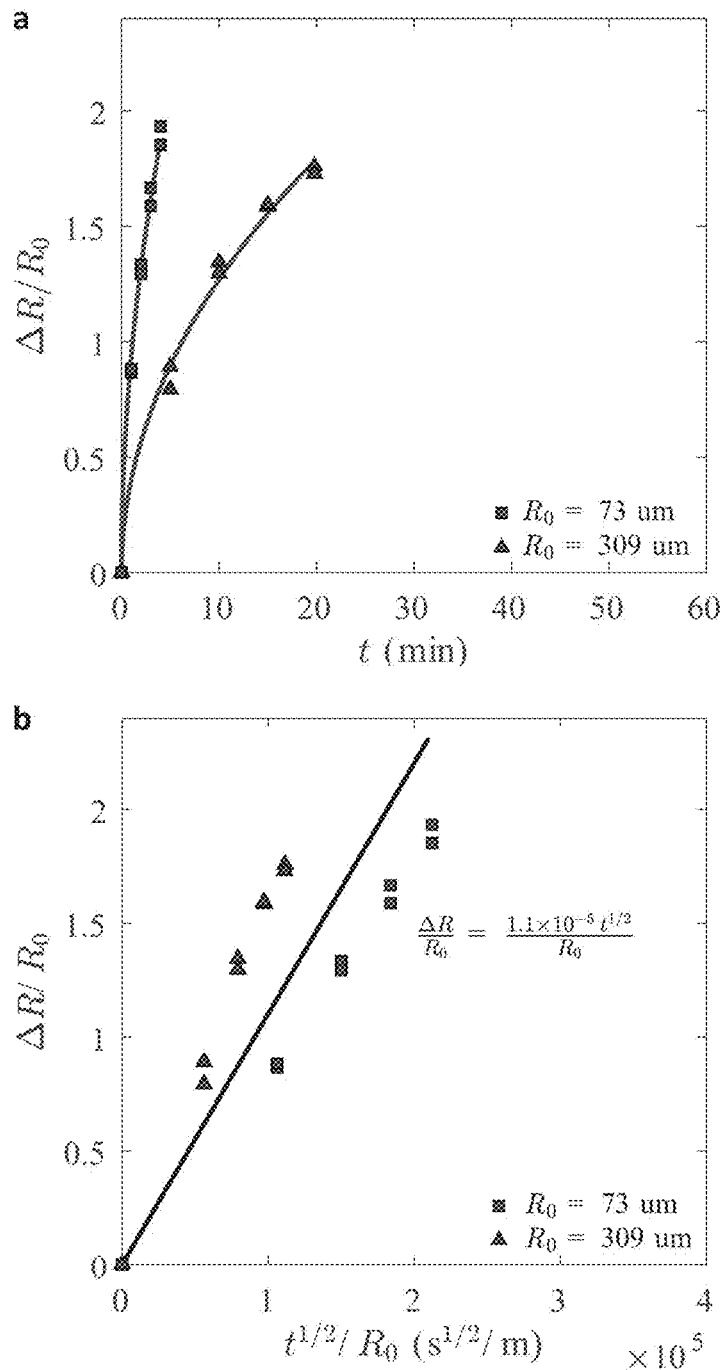
FIG. 24 presents results of the expansion of single fibers B and C: (a) normalized radial expansion, $\Delta R/R_0$, versus time, t, and (b) $\Delta R/R_0$ versus $t^{1/2}/R_0$.

FIG. 24a is a plot of the normalized radial expansion, $\Delta R/R_0$, versus time, t. $\Delta R/R_0$ increased steadily with time at degressive rate. Furthermore, it increased with decreasing initial fiber radius, $R_0$. The 73 μm initial radius fiber (fiber B) expanded to 2.62 times its initial radius after 3 minutes. The same normalized expansion was achieved by the 309 μm initial radius fiber (fiber C) after about 15-20 minutes.

FIG. 24b is a plot of $\Delta R/R_0$ versus $t^{1/2}/R_0$. The data was not entirely independent of fiber radius. Nonetheless, for all fibers a rough correlation of $\Delta R/R_0$ versus $t^{1/2}/R_0$ could be written as:

$$\frac{\Delta R}{R_0} \cong k_{ex} \frac{t^{1/2}}{R_0} \quad (28)$$

where $k_{ex}$ is an expansion rate constant. From FIG. 24b $k_{ex} \sim 1.1 \times 10^{-5}$ m/s$^{1/2}$.

Combining Eq. (28) with the model of Eq. (11a), the diffusivity of dissolution fluid in the fibers may be derived as:

$$D_w = \frac{\pi}{4} \left(\frac{k_{ex} \rho_w}{c_b}\right)^2 \quad (29)$$

Using $c_b \sim 998$ kg/m³, $\rho_w \approx 1000$ kg/m³, the diffusivity by which water or dissolution fluid enters the fiber, $D_w \sim 1 \times 10^{-10}$ m²/s. This is about an order of magnitude smaller than the self-diffusivity of water.

Thus, the thin fibers expand rapidly by the diffusion of water into the interior. The excipient does not hold up water diffusion substantially.

Example 9: Drug Release by Fibers B and C

Drug release by single fibers B and C was determined under the conditions and with the instrumentation described in experimental examples 5 and 6.

Figure 25:
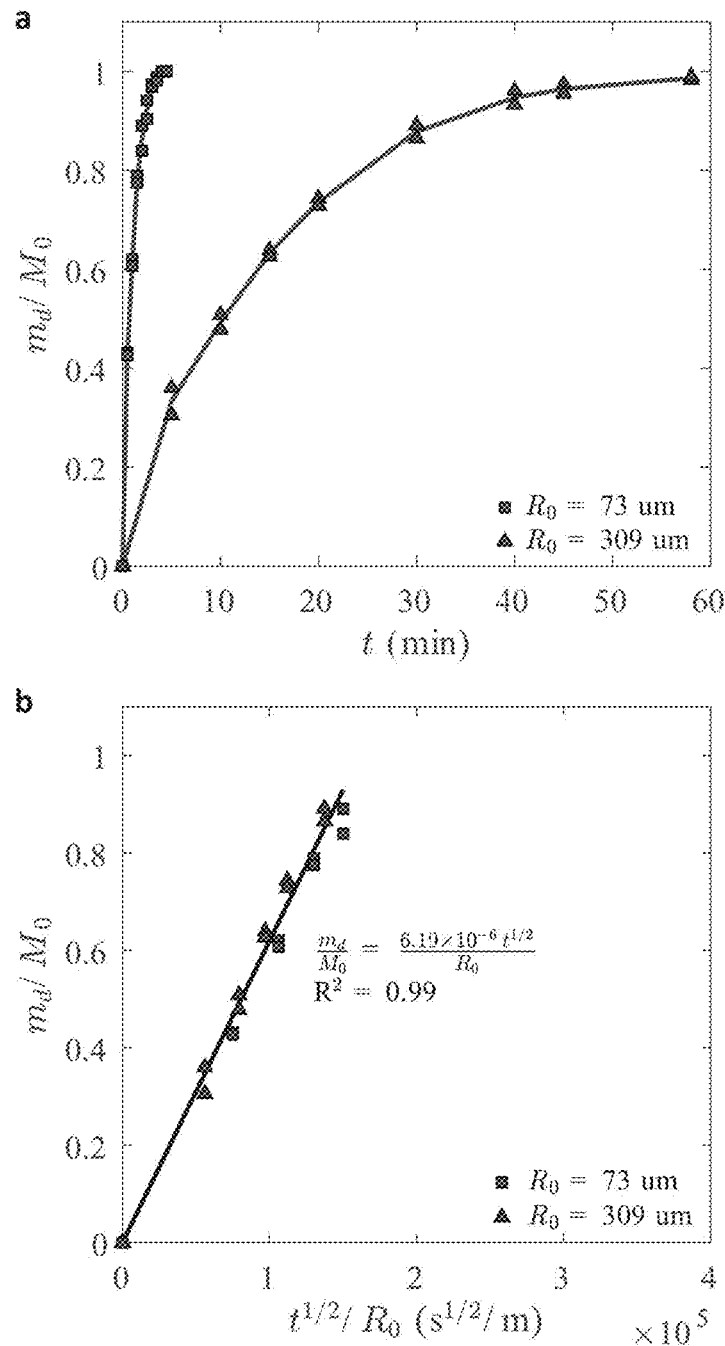
FIG. 25 shows results of drug release by the experimental fibers B and C: (a) fraction of drug dissolved, $m_d/M_0$, versus time, t, and (b) $m_d/M_0$, versus time, $t^{1/2}/R_0$.

FIG. 25a is a plot of the fraction of drug released into the dissolution medium, $m_d/M_0$, versus time, t. For all fibers, the drug was released steadily at degressive rate. The time to release 80 percent of the initial drug content, $t_{0.8}$, increased with increasing fiber radius, from 2.7 minutes for $R_0$=73 μm to 24.5 minutes for $R_0$=309 μm (Table 2).

Furthermore, as shown in FIG. 25b, the fraction of drug released by the fibers was proportional to the square root of time and the reciprocal of fiber radius. Thus, $$\frac{m_d}{M_0} \cong k_d \frac{t^{1/2}}{R_0} \qquad (30)$$

where $k_d$ is a drug release rate constant. From FIG. 25b $k_d$~6.19×10$^{-6}$ m/s$^{1/2}$.

Combining Eqs. (25) and (30), the diffusivity of drug in the fiber may be estimated, roughly, as:

$$D_d = \frac{\pi}{4}\left(\frac{k_d R}{R_0}\right)^2 \qquad (31)$$

For R~2$R_0$ and $k_d$ from FIG. 25b, $D_d$~1×10$^{-10}$ m$^2$/s. This is about an order of magnitude smaller than the diffusivity of the small drug molecule in water.

Thus, as water enters into the thin fibers, the drug diffuses out of the gelated fibers into the dissolution fluid. Because the fibers are thin, drug is released rapidly.

Example 10: Scanning Electron Micrographs of Dosage Forms B and C

Figure 26:
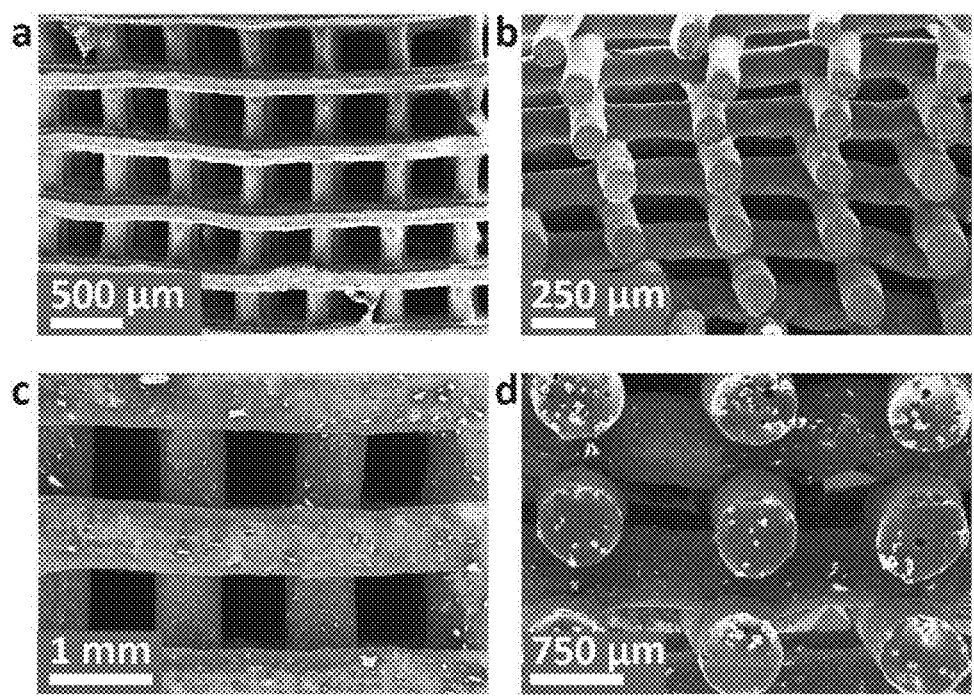
FIG. 26 presents scanning electron micrographs of the microstructures of experimental dosage forms: (a) top-view of dosage form B, (b) side view of dosage form B, (c) top view of dosage form C, and (d) side view of dosage form C.

Scanning electron micrographs of dosage forms B and C were taken with the equipment and under the conditions described in experimental example 4. From FIGS. 26a and 26b the fiber radius, $R_0$, and the inter-fiber distance, $\lambda_0$, in the microstructure of dosage form B were 71 μm and 456 μm, respectively. Moreover, from FIGS. 26c and 26d, in the microstructure of dosage form C the fiber radius, $R_0$=315 μm, and the inter-fiber distance, $\lambda_0$=1466 μm, as listed in Table 2. The measured microstructural parameters in the solid dosage forms were about 0.52-0.72 times the nominal values (Tables 1 and 2).

Example 11: Expansion and Disintegration of Dosage Forms B and C

Images of the disintegrating dosage forms B and C were taken using the equipment and under the conditions described in experimental example 5.

Figure 27:
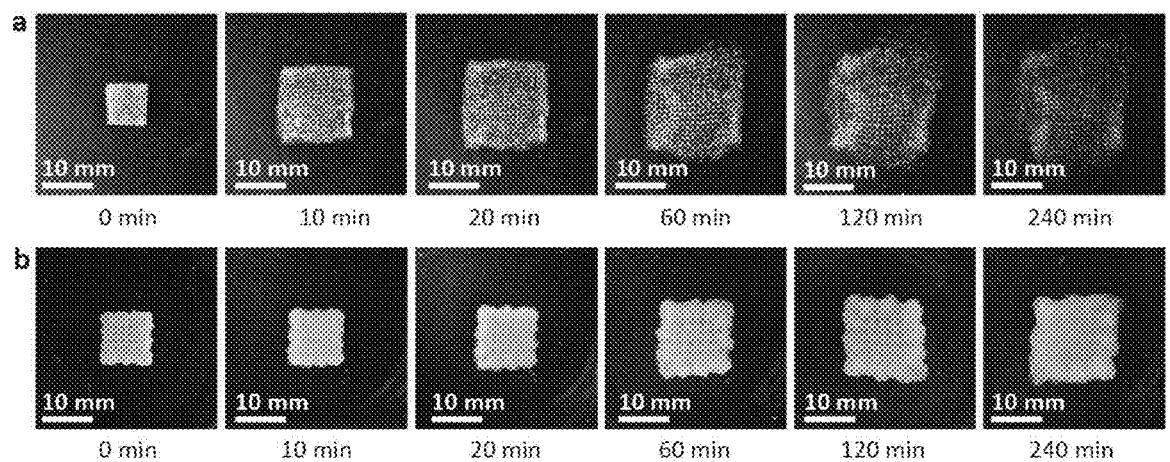
FIG. 27 depicts the expansion and disintegration processes of (a) experimental dosage form B and (b) experimental dosage form C.

FIGS. 27a and 27b present top-view images of dosage forms B and C after immersion in the dissolution fluid. Again, the fluid percolated into the void space almost immediately after immersion. The solid dosage forms then transitioned to a viscous mass and concurrently expanded uniformly in all directions. The viscous mass eroded slowly into the dissolution fluid, thus its geometry was roughly preserved for more than an hour. Eventually, however, the viscous mass disappeared and the dosage form was dissolved.

Figure 28:
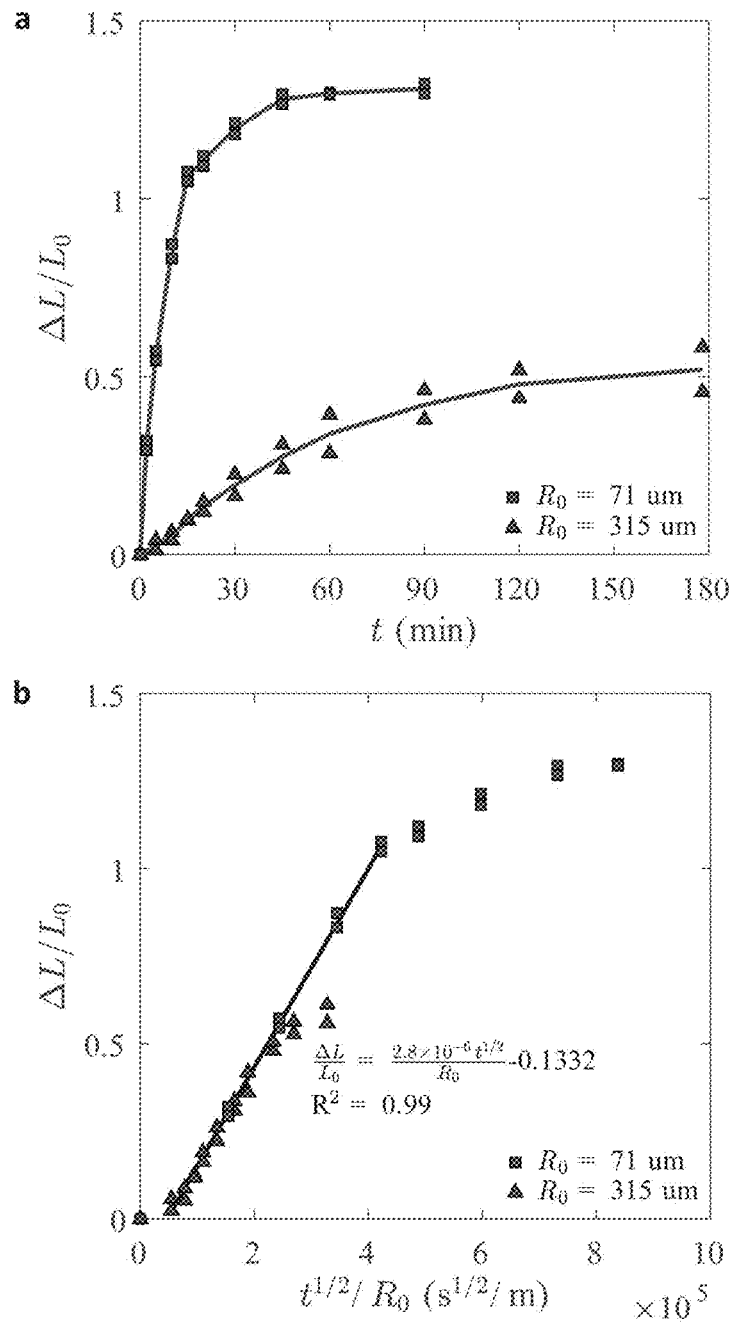
FIG. 28 shows results of dosage form B and C expansion: (a) normalized longitudinal expansion, $\Delta L/L_0$, versus time, t, and (b) $\Delta L/L_0$ versus $t^{1/2/R}{}_0$.
Figure 29:
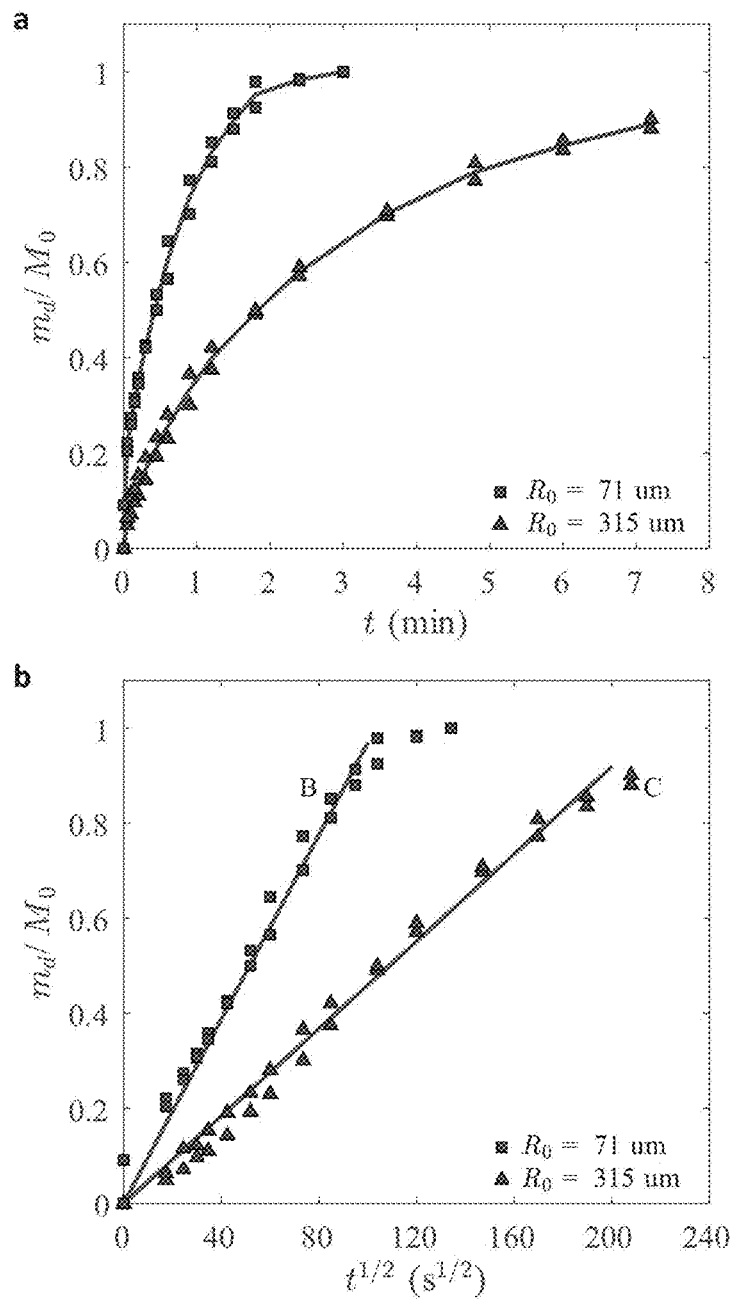
FIG. 29 presents the drug release results by dosage forms B and C: (a) fraction of drug dissolved, $m_d/M_0$, versus time, t, and (b) $m_d/M_0$, versus $t^{1/2}$.

FIG. 28a is a plot of the normalized longitudinal expansion, $\Delta L/L_0$, versus time, t. For all the dosage forms, $\Delta L/L_0$ increased with time at degressive rate. The ratios of the dosage form length at 15 minutes and the initial length, $L_{15}/L_0$, are listed in Table 2. $L_{15}/L_0$ increased with decreasing fiber radius, from 1.12 for $R_0$=315 μm (dosage form C) to 2.06 for $R_0$=71 μm (dosage form B).

Thus, at the expansion rate of the 71 μm initial fiber radius dosage form (dosage form B), the diameter of a 9.7 mm diameter disk increases to 20 mm in just 15 minutes after immersion. This expansion rate should be fast enough to ensure convenient swallowing of the dosage form and prevent premature passage of the viscous medium into the intestines.

FIG. 28b is a plot of $\Delta L/L_0$ versus $t^{1/2}/R_0$. $\Delta L/L_0$ was proportional to $t^{1/2}/R_0$ initially and could be approximated by a curve of the form:

$$\frac{\Delta L}{L_0} \propto k_{RL} \frac{\Delta R}{R_0} \qquad (32)$$

where $k_{RL}$ is an expansion rate constant. From FIG. 28b $k_{RL}$=2.8×10$^{-6}$ m/s$^{1/2}$. The expansion rate constant of the fibrous dosage forms was about 4 times smaller than that of the single fibers.

Past the linear regime, the curve of $\Delta L/L_0$ versus $t^{1/2}/R_0$ plateaued to a value that was roughly constant. The curve plateaued as soon as the dosage form was converted to uniform viscous mass. The "final" $\Delta L/L_0$ value was between 0.52 and 1.3 for the dosage forms presented (dosage forms B and C). The curve plateaued because water diffusion into the thick viscous mass is much slower than into the thin fibers of the fibrous dosage form, and thus the expansion rate of the viscous mass is reduced greatly (e.g., the expansion rate of the drug containing solid while transitioning to a viscous mass is much greater than the expansion rate of a uniform or almost uniform viscous mass).

TABLE 2

Disintegration and drug release properties of fibrous dosage forms after immersion into 500 ml dissolution fluid.

|  | $R_0$ (μm) | $\lambda_0$ (μm) | $R_0/\lambda_0$ | φs | $\Delta R_2/R_0$ | $L_2/L_0$ | $L_{15}/L_0$ | $t_{0.8}$ (min) |
|---|---|---|---|---|---|---|---|---|
| Fibrous dosage forms | | | | | | | | |
| A | 104 ± 4 | 385 ± 15 | 0.27 | 0.53 | — | 1.43 | — | 9.0 |
| B | 71 ± 10 | 456 ± 37 | 0.16 | 0.33 | — | — | 2.06 | 110.0 |
| C | 315 ± 12 | 1466 ± 52 | 0.21 | 0.41 | — | — | 1.12 | 501.8 |
| Single fibers | | | | | | | | |
| A | 102 ± 3 | — | — | — | 0.52 | 0.34 | — | 3.0 |
| B | 73 ± 4 | — | — | — | — | — | — | 2.7 |
| C | 309 ± 11 | — | — | — | — | — | — | 24.5 |

$\Delta R_2/R_0$ and $\Delta L_2/L_0$ are the normalized radial and longitudinal expansion 2 minutes after immersion.
$t_{0.8}$ is the time to release 80% of the drug mass in the dosage forms and fibers. The data are obtained from the results presented in FIGS. 17-29.

Example 12: Drug Release by Dosage Forms B and C

Drug release by dosage forms B and C was determined under the conditions and with the instrumentation described in experimental examples 5 and 6.

The fraction of drug released by the fibrous dosage forms versus time is shown in FIG. 29a. In all cases, the curves increased steadily with time but at a decreasing slope. The time to release 80 percent of the drug content, $t_{0.8}$, was between 110 ($R_0$=71 µm, dosage form B) and 502 minutes ($R_0$=315 µm, dosage form C) as listed in Table 2. This is about 20-41 times longer than the values of the corresponding single fibers.

FIG. 29b is a plot of the fraction of drug released versus square root of time. The curves were essentially linear and could be approximated by a function of the form:

$$\frac{m_d}{M_0} \cong k_d t^{1/2} \quad (33)$$

where $k_d$ is a drug release rate constant. $k_d$ decreased with increasing fiber radius, from $9.7\times10^{-3}$ s$^{-1/2}$ for $R_0$=71 µm to $4.6\times10^{-3}$ s$^{-1/2}$ for $R_0$=315 µm (FIG. 29b).

Combining Eqs. (24) and (33), the diffusivity of drug through the viscous mass, $$D_d = \frac{\pi H^2 k_d^2}{16} \quad (34)$$

Using $H \approx 2H_0$, and the data of $k_d$ from the caption of FIG. 29b, $D_d$=6.6 and $1.5\times10^{-10}$ m$^2$/s, respectively, for dosage forms B and C.

The estimated diffusivities in the viscous mass are of the order of the diffusivity of the small drug molecule in water. Furthermore, the drug diffusivity through the viscous mass is increased if the fiber radius is decreased, due to the faster expansion rate and the greater volume fraction of water in the viscous mass. The drug release and expansion rates are therefore coupled: dosage forms with thin, small-radius fibers expand and release drug faster than the dosage forms with larger radius fibers.

Nonetheless, because the diffusion length of the drug molecules changes from the fiber radius to the thickness of the viscous mass, the rate of drug release by the dosage forms is much slower than that by the single fibers.

Figure 30:
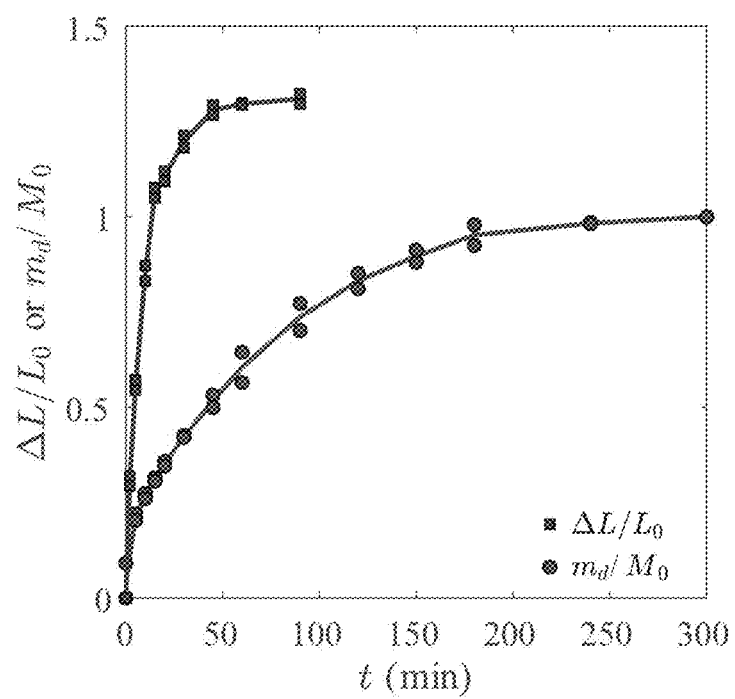
FIG. 30 presents both the normalized longitudinal expansion, $\Delta L/L_0$, and the fraction of drug dissolved, $m_d/M_0$, by dosage form B versus time.

As a result, as shown in FIG. 30, the thin-fiber dosage form B expands rapidly due to the diffusion of dissolution fluid into the thin fibers and transitions to a viscous mass. The drug is then released slowly by diffusion of drug molecules through the thick, expanded viscous mass.

Thus, dosage form B satisfies the twin functional requirements of a gastroretentive sustained release dosage form: fast dosage form expansion and prolonged drug release.

Example 13: Viscosities of Viscous Media and Solutions (a) Water and HPMC of Molecular Weight 10 kg/mol The shear viscosity of water with HPMC of molecular weight 10 kg/mol was determined with a shear rheometer (TA Instruments, ARG2 Rheometer, stress-controlled) equipped with a 60 mm diameter cone with an apex angle of 178°. The concentration of excipient (HPMC with molecular weight 10 kg/mol) in the viscous solutions analyzed was 1, 2, 5, 10, and 20 wt %. The temperature during the experiments was 37° C., and the shear strain-rate range was 1-100/s.

Figure 31:
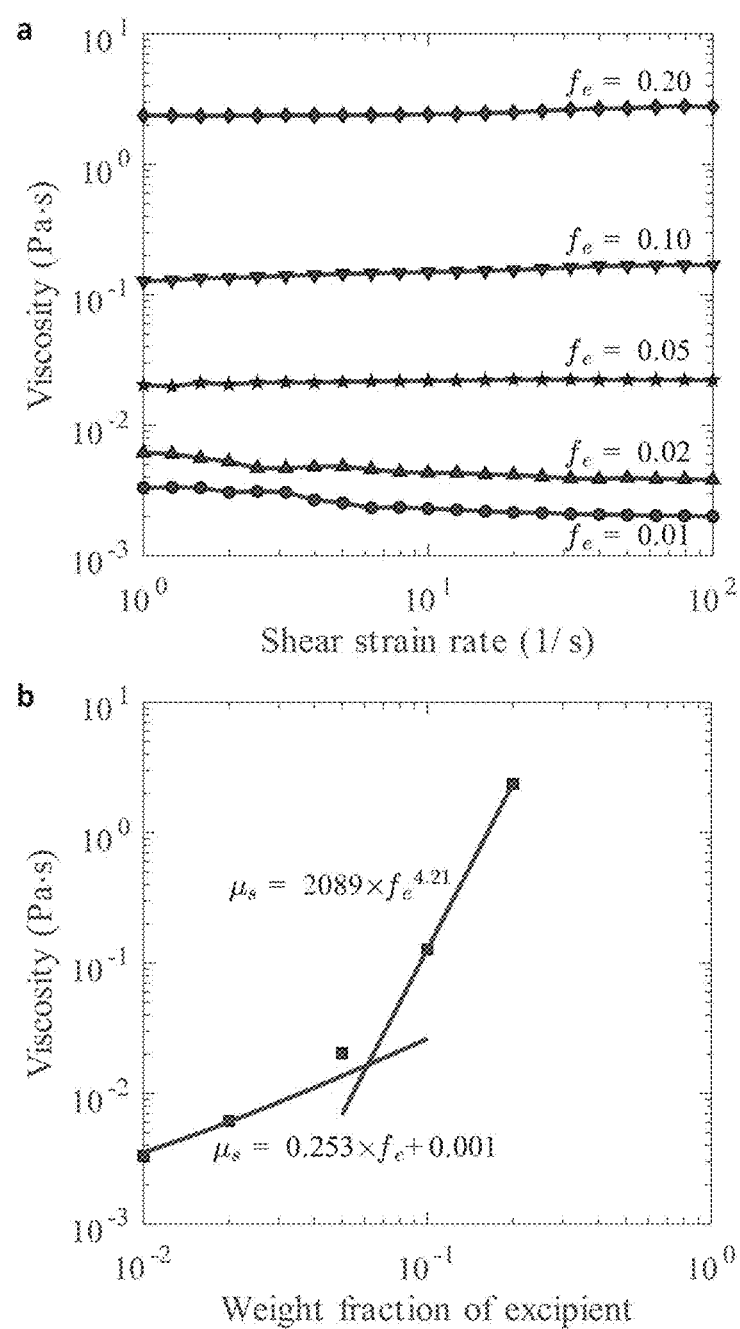
FIG. 31 presents experimental results of the shear viscosity of HPMC10k-water solutions: (a) shear viscosity versus shear strain rate, and (b) shear viscosity at a shear strain rate of 1/s versus weight fraction of HPMC, $f_e$.

FIG. 31 presents the shear viscosity, $\mu_s$, at various weight fractions of the excipient, $f_e$. FIG. 31a is the viscosity versus shear rate in the range 1-100/s and FIG. 31b shows $\mu_s$ versus $f_e$ at a shear rate of 1/s. In the dilute regime, referred to herein as the regime where the excipient weight fraction is smaller than the disentanglement weight fraction, the viscosity followed an equation of the form of the Einstein viscosity relation, $\mu_s$=0.253 $f_e$+0.001 Pa·s. In the semi-dilute regime, $\mu_s$=2089 $f_e^{4.21}$. The dilute and semi-dilute regimes were separated by the disentanglement weight fraction, $f_e^*$=0.062. Thus, the disentanglement concentration of the excipient, $c_e^* \approx 70$ mg/ml.

(b) Water and HPMC of Molecular Weight 120 kg/mol

The shear viscosity of water with HPMC of molecular weight 120 kg/mol was determined with the same shear rheometer. The rheometer was equipped with either a 60 mm diameter cone with an apex angle of 178° (for measuring the viscosity of mixtures with an excipient weight fraction smaller than 0.1) or a 20 mm diameter cone with an apex angle of 176° (for measuring the viscosity of mixtures with an excipient weight fraction greater than 0.1). The solutions tested consisted of water and HPMC excipient (molecular weight=120 kg/mol) at excipient weight fractions, $f_e$, in the range $5\times10^{-4}$–0.5. The temperature was 37° C. during the experiments.

The sample was flowing like a fluid between the rotating cone and the plate if the excipient weight fraction was no greater than 0.3. If the excipient weight fraction was 0.5, however, the solution behaved essentially like a solid block: the rotating cone was turning on the surface of the sample, but the sample was not deformed.

Figure 32:
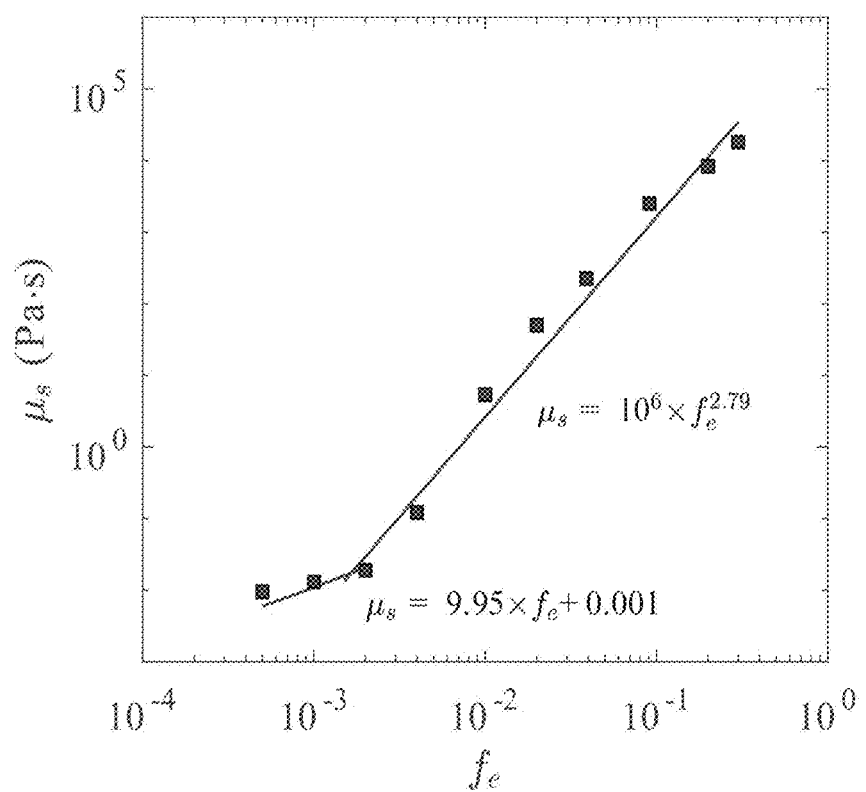
FIG. 32 shows experimental results of the shear viscosity of HPMC120k-water solutions, $\mu_s$, at a shear strain rate of 1/s versus weight fraction of HPMC, $f_e$.

FIG. 32 presents the shear viscosity, $\mu_s$, versus excipient weight fraction, $f_e$, at a shear rate of 1/s in the range $5\times10^{-4} \leq f_e \leq 0.3$. Two regimes could be distinguished: dilute and a semi-dilute. In the dilute regime, the viscosity followed the Einstein viscosity relation: $\mu_s$=0.001+9.95 $f_e$ Pa·s. In the semi-dilute regime, referred to herein as the regime where the excipient weight fraction is greater than the disentanglement weight fraction but smaller than the semi-dilute/solid demarcation, $\mu_s$=10$^6$ $f_e^{2.79}$. The dilute and semi-dilute regimes were demarcated by the disentanglement weight fraction, $f_e^*$=1.67$\times10^{-3}$. Thus, the disentanglement concentration of the excipient, $c_e^*$ 1.67 mg/ml. The water concentration at disentanglement of the excipient, $c_w^* \approx 998$ mg/ml.

Because the sample behaved essentially like a solid block when the excipient weight fraction was 0.5, this weight fraction may be used here as the semi-dilute/solid demarcation. The excipient concentration at the semi-dilute/solid demarcation, $c_e^{} \approx 500$ mg/ml. The water concentration at the semi-dilute/solid demarcation, $c_w^{} \approx 500$ mg/ml.

Application Examples

In some embodiments, the amount of active ingredient contained in a dosage form disclosed in this invention is appropriate for administration in a therapeutic regimen that shows a statistically significant probability of achieving a predetermined therapeutic effect when administered to a relevant population. By way of example but not by way of limitation, active ingredients may be selected from the group consisting of acetaminophen, aspirin, caffeine, ibuprofen, an analgesic, an anti-inflammatory agent, an anthelmintic, anti-arrhythmic, antibiotic, anticoagulant, antidepressant, antidiabetic, antiepileptic, antihistamine, antihypertensive, antimuscarinic, antimycobacterial, antineoplastic, immunosuppressant, antithyroid, antiviral, anxiolytic and sedatives, beta-adrenoceptor blocking agents, cardiac inotropic agent, corticosteroid, cough suppressant, diuretic, dopaminergic, immunological agent, lipid regulating agent, muscle relaxant, parasympathomimetic, parathyroid, calcitonin and biphosphonates, prostaglandin, radiopharmaceutical, anti-allergic agent, sympathomimetic, thyroid agent, PDE IV inhibitor, CSBP/RK/p38 inhibitor, or a vasodilator).

The dosage forms disclosed herein have predictable microstructure and drug release behavior. They enable a greater range and improved control of the drug delivery rate into the blood stream. While useful for improving almost any drug therapy, the disclosed dosage forms are particularly beneficial for increasing the delivery rate of drugs that are sparingly (e.g., poorly) soluble in gastrointestinal fluid. Thus, in some embodiments at least one active pharmaceutical ingredient comprises a solubility no greater than 5 g/l in physiological/body fluid under physiological conditions. This includes, but is not limited to at least one active ingredient having a solubility no greater than 2 g/l, or no greater than 1 g/l, or no greater than 0.5 g/l, or no greater than 0.2 g/l, or no greater than 0.1 g/l in a physiological or body fluid under physiological conditions.

Finally, the disclosed dosage forms can be manufactured by an economical process enabling more personalized medicine.

We claim:

1. A pharmaceutical dosage form comprising:
   a drug-containing solid having an outer surface and an internal three dimensional structural framework of one or more thin structural elements, said framework contiguous with and terminating at said outer surface;
   said thin structural elements having an average thickness in the range of 2.5 µm to 2 mm;
   said thin structural elements further comprising at least an active pharmaceutical ingredient, at least an absorptive polymeric excipient being mutually soluble with a physiological fluid, and at least a hydrophilic surface composition;
   said thin structural elements further having segments spaced apart from adjoining segments, thereby defining free spaces, wherein a plurality of adjacent free spaces combine across the drug-containing solid to define one or more interconnected free spaces forming an open pore network;
   whereby
   upon immersion in a physiological fluid said open pore network enables uniform wetting of the structural framework, and the drug-containing solid transitions to a viscous medium, thereby expanding in all dimensions.

2. The dosage form of claim 1, wherein the drug-containing solid dissolves or disintegrates in the physiological fluid during or after transitioning to a viscous medium.

3. The dosage form of claim 1, wherein the drug-containing solid expands due to the penetration of physiological or body fluid into one or more thin elements of the three dimensional structural framework.

4. The dosage form of claim 1, wherein at least one dimension of the drug-containing solid expands to at least 1.15 times its initial length while transitioning to a viscous medium.

5. The dosage form of claim 1, wherein at least one dimension of the drug-containing solid expands to at least 1.15 times its initial length within no more than 20 minutes of immersing in a physiological or body fluid.

6. The dosage form of claim 1, wherein at least one absorptive polymeric excipient being mutually soluble with a physiological fluid comprises hydroxypropyl methylcellulose.

7. The dosage form of claim 1, wherein the drug-containing solid expands isotropically while transitioning to a viscous medium.

8. The dosage form of claim 1, wherein geometric similarity of the three dimensional structural framework of elements is preserved as it expands and transitions to a fluidic or viscous medium.

9. The dosage form of claim 1, wherein the drug-containing solid transitions to a viscous medium having a viscosity in the range of 0.01 to 10,000 Pa·s.

10. The dosage form of claim 1, wherein eighty percent of the drug content in the drug-containing solid is released in less than 45 minutes after immersion in a physiological or body fluid.

11. The dosage form of claim 1, wherein the one or more elements comprise an average thickness in the range 1 µm-1 mm.

12. The dosage form of claim 1, wherein the effective free spacing between the segments across the one or more free spaces on average is in the range 10 µm-2 mm.

13. The dosage form of claim 1, wherein the three dimensional structural framework of one or more elements comprises an ordered structure.

14. The dosage form of claim 1, wherein the effective free spacing and element thickness are precisely controlled.

15. The dosage form of claim 1, wherein the three dimensional structural framework of one or more thin structural elements comprises a plurality of stacked layers of elements or segments.

16. The dosage form of claim 1, wherein the elements comprise segments bonded to other segments at point contacts, the number of point contacts in the three dimensional structural framework being precisely controlled.

17. The dosage form of claim 16, wherein one or more segments are diffusion-bonded to one or more other segments.

18. The dosage form of claim 1, wherein at least one element is a fiber.

19. The dosage form of claim 1, wherein the three dimensional structural framework of one or more thin structural elements comprises a plurality of criss-crossed stacked layers of fibrous structural elements.

20. The dosage form of claim 19, wherein the spacing between adjoining fibers or adjoining fiber segments in a layer is uniform or equidistant.

21. The dosage form of claim 1, wherein at least one element is a sheet.

22. The dosage form of claim 1, wherein at least one element is a bead.

23. The dosage form of claim 1, wherein the surface of at least one element or the surface of at least one segment comprises a coating.

24. The dosage form of claim 1, wherein the coating comprises a highly hydrophilic surface composition for enhancing the rate of wetting of the structural framework or the rate of fluid percolation into the open pore network.

25. The dosage form of claim 1, wherein the at least one highly hydrophilic coating composition is selected from the group comprising polyethylene glycol, polyvinyl alcohol, polyvinyl alcohol-polyethylene glycol copolymer, polyvinyl pyrrolidone, silicon dioxide, talc, magnesium stearate, mannitol, xylitol, maltitol, erythritol, sucrose, glucose, isomalt, maltodextrin, or lactitol.

26. The dosage form of claim 1, wherein the free spacing between segments and the composition of the surface of the one or more elements are so that the percolation time of physiological/body fluid into one or more interconnected free spaces of the drug-containing solid is no greater than 200 seconds under physiological conditions.

27. The dosage form of claim 1, wherein rate of penetration of the physiological/body fluid into an element or an absorptive excipient under physiological conditions is greater than the average thickness of said element divided by 3600 seconds.

28. The dosage form of claim 1, wherein at least one absorptive polymeric excipient is selected from the group comprising hydroxypropyl methylcellulose, hydroxyethyl cellulose, polyvinyl alcohol, polyvinylpyrrolidone, hydroxypropyl methylcellulose acetate succinate, sodium alginate, hydroxypropyl cellulose, methyl cellulose, hydroxypropyl methyl ether cellulose, starch, chitosan, pectin, polymethacrylate, polyacrylic acid, or vinylpyrrolidone-vinyl acetate copolymer.

29. The dosage form of claim 1, wherein at least one absorptive polymeric excipient comprises a plurality of individual chains that disentangle upon immersion in a physiological fluid.

30. The dosage form of claim 1, wherein the molecular weight of at least one absorptive polymeric excipient is between 2 kg/mol and 500 kg/mol.

31. The dosage form of claim 1, wherein the weight fraction of absorptive polymeric excipient in the three dimensional structural framework of one or more elements is greater than 0.15.

32. The dosage form of claim 1, wherein the absorptive polymeric excipient is predominantly in an amorphous phase.

33. The dosage form of claim 1, wherein drug molecules or drug particles are embedded in a matrix comprising absorptive polymeric excipient.

34. The dosage form of claim 1, wherein drug and excipient in the structural elements form a solid solution.

35. The dosage form of claim 1, wherein at least one active pharmaceutical ingredient comprises a solubility no greater than 1 g/l in a physiological or body fluid under physiological conditions.

36. A pharmaceutical dosage form comprising:
a drug-containing solid having an outer surface and an internal three dimensional structural framework of one or more thin structural elements with average element thickness in the range of 2.5 µm to 2 mm, said framework contiguous with and terminating at said outer surface;
said thin structural elements comprising at least an active pharmaceutical ingredient, at least 15 weight percent of one or more absorptive polymeric excipients being mutually soluble with a physiological fluid and having a molecular weight in the range between 2 kg/mol and 500 kg/mol, and at least a hydrophilic surface composition;
said thin structural elements further having segments spaced apart from adjoining segments, thereby defining free spaces, wherein a plurality of adjacent free spaces combine across the drug-containing solid to define one or more interconnected free spaces forming an open pore network;
wherein
upon immersion in a physiological fluid said open pore network enables uniform wetting of the structural framework, and the physiological fluid penetrates into the thin fibers, so that the drug-containing solid expands in all dimensions and transitions to a viscous medium.

37. A pharmaceutical dosage form comprising:
a drug-containing solid having an outer surface and an internal three dimensional structural framework comprising a plurality of criss-crossed stacked layers of fibrous structural elements with average fiber thickness in the range of 2.5 µm to 2 mm, said framework contiguous with and terminating at said outer surface;
said fibrous structural elements comprising at least an active pharmaceutical ingredient, at least an absorptive polymeric excipient being mutually soluble with a physiological fluid, and at least a hydrophilic surface composition;
said fibrous structural elements further having segments spaced apart from like segments of adjoining fibrous elements, thereby defining free spaces, wherein a plurality of adjacent free spaces of successive layers combine to define one or more interconnected free spaces forming an open pore network;
wherein
upon immersion in a physiological fluid said open pore network enables uniform wetting of the structural framework, and the physiological fluid penetrates into the thin fibers, so that the drug-containing solid expands in all dimensions and transitions to a viscous medium.

* * * * *